(12) United States Patent
Wang et al.

(10) Patent No.: US 12,290,359 B2
(45) Date of Patent: May 6, 2025

(54) SENSOR ARRAY SYSTEMS AND METHODS FOR DETECTING MULTIPLE ANALYTES

(71) Applicant: ABBOTT DIABETES CARE INC., Alameda, CA (US)

(72) Inventors: Yi Wang, Danville, CA (US); Hyun Cho, Berkeley, CA (US); Benjamin J. Feldman, Berkeley, CA (US); Kuan-Chou Chen, Fremont, CA (US); Lam N. Tran, Danville, CA (US); Stephen Oja, Reno, NV (US); Tianmei Ouyang, Saratoga, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 404 days.

(21) Appl. No.: 17/138,477

(22) Filed: Dec. 30, 2020

(65) Prior Publication Data
US 2021/0219885 A1 Jul. 22, 2021

Related U.S. Application Data

(60) Provisional application No. 62/956,943, filed on Jan. 3, 2020.

(51) Int. Cl.
*A61B 5/1486* (2006.01)
*A61B 5/145* (2006.01)

(52) U.S. Cl.
CPC ...... *A61B 5/14865* (2013.01); *A61B 5/14532* (2013.01); *A61B 2562/125* (2013.01); *A61B 2562/16* (2013.01)

(58) Field of Classification Search
CPC ............ A61B 5/14865; A61B 5/14532; A61B 2562/125; A61B 2562/16; A61B 5/6833; A61B 5/6848
See application file for complete search history.

(56) References Cited

U.S. PATENT DOCUMENTS

| 4,721,677 A | 1/1988 | Clark |
| 5,322,063 A | 6/1994 | Allen et al. |

(Continued)

FOREIGN PATENT DOCUMENTS

| EP | 4084689 A1 | 11/2022 |
| GB | 2067764 A | 7/1981 |

(Continued)

OTHER PUBLICATIONS

ISR-WO dated May 5, 2021 for related matter PCT/US20/67540 (applicant notes that US20190320947 cited in the ISR was already submitted in an IDS dated Jan. 4, 2021).

(Continued)

*Primary Examiner* — David J. McCrosky
*Assistant Examiner* — Meghan R Kumar
(74) *Attorney, Agent, or Firm* — STERNE, KESSLER, GOLDSTEIN & FOX P.L.L.C.

(57) ABSTRACT

Multiple analytes may be dysregulated singularly or concurrently in certain physiological conditions and may be advantageously assayed together using analyte sensors capable of detecting multiple analytes. Certain analyte sensors capable of the detection of multiple analytes may include first and second working electrodes, analyte-responsive active areas disposed on each of the working electrodes, and reference and counter electrodes. Analyte sensors that include multiple working electrodes but do not include reference and counter electrodes can also be used in conjunction with another sensor that contains reference and counter electrodes, such that these electrodes are shared.

11 Claims, 25 Drawing Sheets

(56) References Cited

U.S. PATENT DOCUMENTS

| | | |
|---|---|---|
| 5,696,314 A | 12/1997 | McCaffrey et al. |
| 5,792,621 A | 8/1998 | Verostko et al. |
| 6,134,461 A | 10/2000 | Say et al. |
| 6,241,863 B1 | 6/2001 | Monbouquette |
| 6,605,200 B1 | 8/2003 | Mao et al. |
| 6,605,201 B1 | 8/2003 | Mao et al. |
| 6,736,957 B1 | 5/2004 | Forrow et al. |
| 6,946,299 B2 | 9/2005 | Neel et al. |
| 7,501,053 B2 | 3/2009 | Karinka et al. |
| 7,563,588 B2 | 7/2009 | Gao et al. |
| 7,754,093 B2 | 7/2010 | Forrow et al. |
| 8,268,143 B2 | 9/2012 | Liu et al. |
| 8,444,834 B2 | 5/2013 | Liu et al. |
| 8,545,693 B2 * | 10/2013 | McColl ............... G01N 27/3271 204/403.01 |
| 9,290,839 B2 | 3/2016 | Wang et al. |
| 9,914,952 B2 | 3/2018 | Ouyang et al. |
| 9,927,386 B2 | 3/2018 | Wang et al. |
| 9,983,161 B2 | 5/2018 | Feldman et al. |
| 10,022,076 B2 | 7/2018 | Hoss et al. |
| 10,201,301 B2 | 2/2019 | Heller et al. |
| 10,702,193 B2 | 7/2020 | Simpson et al. |
| 2001/0003045 A1 | 6/2001 | Davis et al. |
| 2003/0042137 A1 | 3/2003 | Mao et al. |
| 2003/0050547 A1 | 3/2003 | Lebel et al. |
| 2004/0061232 A1 | 4/2004 | Shah et al. |
| 2005/0148832 A1 * | 7/2005 | Reghabi ............... A61B 5/4839 600/561 |
| 2005/0215871 A1 | 9/2005 | Feldman et al. |
| 2006/0004272 A1 | 1/2006 | Shah et al. |
| 2006/0257996 A1 | 11/2006 | Simpson et al. |
| 2007/0270672 A1 | 11/2007 | Hayter et al. |
| 2010/0213057 A1 | 8/2010 | Feldman et al. |
| 2010/0267161 A1 | 10/2010 | Wu et al. |
| 2011/0046467 A1 | 2/2011 | Simpson et al. |
| 2011/0213225 A1 | 9/2011 | Bernstein et al. |
| 2012/0132525 A1 * | 5/2012 | Liu ..................... C07F 15/0026 525/327.1 |
| 2012/0181189 A1 | 7/2012 | Merchant |
| 2013/0131478 A1 | 5/2013 | Simpson et al. |
| 2013/0211219 A1 | 8/2013 | Coppeta et al. |
| 2014/0054171 A1 * | 2/2014 | Feldman ............ G01N 27/3272 204/403.14 |
| 2014/0176338 A1 | 4/2014 | He et al. |
| 2014/0127728 A1 | 5/2014 | Wilsey |
| 2016/0345882 A1 | 12/2016 | Wu et al. |
| 2017/0156652 A1 | 6/2017 | Qiang et al. |
| 2017/0315077 A1 | 11/2017 | Rao et al. |
| 2017/0319111 A1 | 11/2017 | Simpson et al. |
| 2019/0004005 A1 | 1/2019 | Oja et al. |
| 2019/0125230 A1 | 5/2019 | Feldman |
| 2019/0320947 A1 | 10/2019 | Chen et al. |
| 2020/0237275 A1 | 7/2020 | Feldman et al. |
| 2020/0237276 A1 | 7/2020 | Oja et al. |
| 2020/0237277 A1 | 7/2020 | Ouyang et al. |
| 2020/0241015 A1 | 7/2020 | Ouyang et al. |

FOREIGN PATENT DOCUMENTS

| | | | |
|---|---|---|---|
| JP | 2015198960 A * | 11/2015 | ......... A61B 5/14532 |
| WO | WO-2003056319 A2 | 7/2003 | |

OTHER PUBLICATIONS

WO, PCT/US2020/015365 ISR and Written Opinion, May 28, 2020.

Cardosi, M., et al., "Amperometric Glucose Sensors for Whole Blood Measurement on Dehydrogenase Enzymes", InTech, 2012, pp. 319-354.

Guiseppi-Elie, A., et al., "Design of a Subcutaneous Implantable Biochip for Monitoring of Glucose and Lactate", IEEE Sensors Journal, 2005, vol. 5, No. 3, pp. 345-355.

Pundir, C.S., et al., "Biosensing Methods for Determination of Creatinine: A Review", Biosensors and Bioelectronics Journal, 2019, vol. 126, pp. 707-724.

Pickup, J.C., "Glucose Sensors: Present and Future," in International Textbook of Diabetes Mellitus, Third Edition, vol. Two, Defronzo, R.A., eds., pp. 1686-1694, John Wiley & Sons Inc., United States (2004).

* cited by examiner

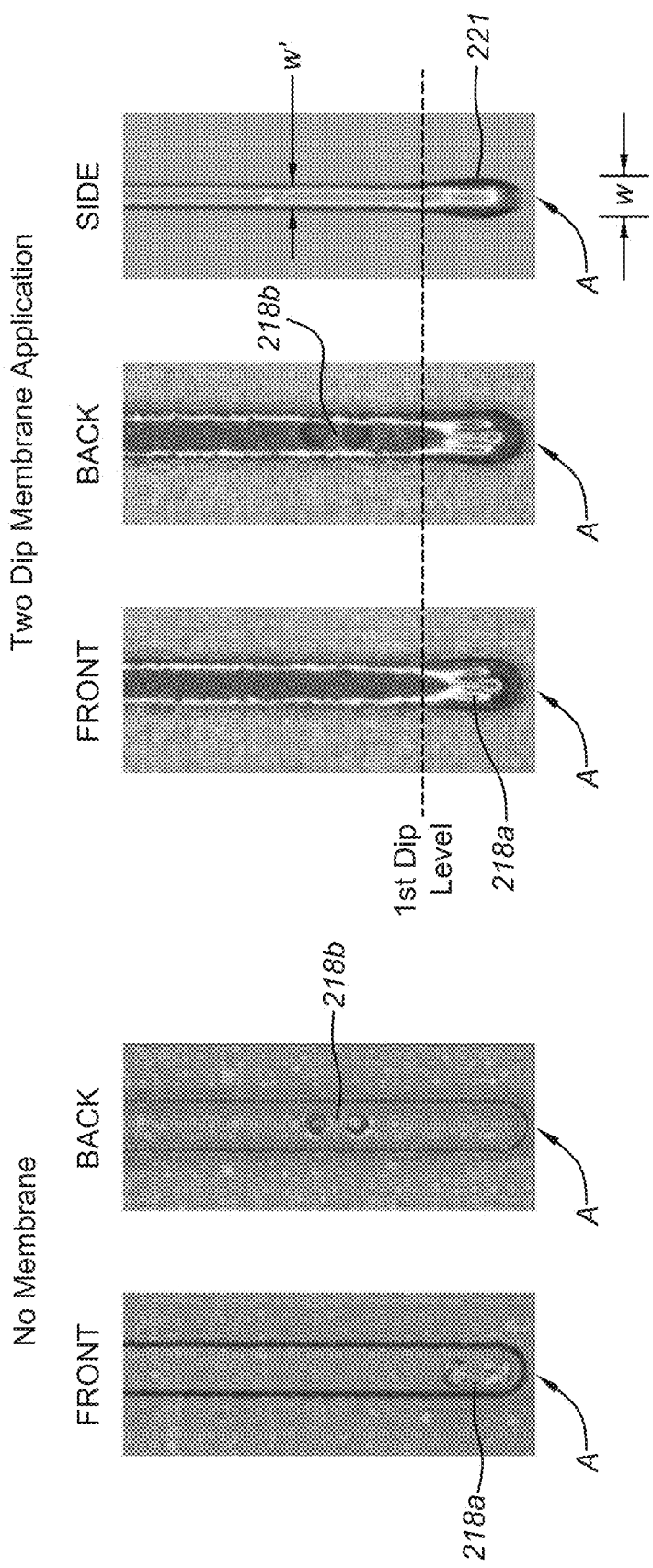

Ketone Electrode
PVP Membrane + 10Q5 Membrane

Glucose Electrode
10Q5 Membrane

PVP Stripe Coat

SENSOR ARRAY SYSTEMS AND METHODS FOR DETECTING MULTIPLE ANALYTES

CROSS-REFERENCE TO RELATED APPLICATIONS

This application claims priority to, and the benefit of, U.S. Provisional Application No. 62/956,943, filed Jan. 3, 2020, which is hereby expressly incorporated by reference in its entirety for all purposes.

STATEMENT REGARDING FEDERALLY SPONSORED RESEARCH OR DEVELOPMENT

Not applicable.

BACKGROUND

The detection of various analytes within an individual can sometimes be vital for monitoring the condition of their health and well-being. Deviation from normal analyte levels can often be indicative of an underlying physiological condition, such as a metabolic condition or illness, or exposure to particular environmental conditions. While a single analyte may be singularly dysregulated for a given physiological condition, it is sometimes the case that multiple analytes are concurrently dysregulated, either due to the same physiological condition or resulting from a comorbid (related) physiological condition. When multiple analytes are concurrently dysregulated, the extent of dysregulation may vary for each analyte. As such, each analyte may need to be monitored to obtain a satisfactory evaluation of an individual's health.

Periodic, ex vivo analyte monitoring using a withdrawn bodily fluid can be sufficient to observe a given physiological condition for many individuals. However, ex vivo analyte monitoring may be inconvenient or painful for some persons, particularly if bodily fluid withdrawal or collection needs to occur fairly frequently (e.g., several times per day). Continuous analyte monitoring using an implanted in vivo analyte sensor may be a more desirable approach for individuals having severe analyte dysregulation and/or rapidly fluctuating analyte levels, although it can also be beneficial for other individuals as well due to the convenience offered. Continuous analyte monitoring may allow an individual or physician to proactively address abnormal analyte levels before they have an opportunity to lead to more significant health consequences, such as organ damage or failure. Subcutaneous, interstitial, or dermal analyte sensors can provide sufficient measurement accuracy for this purpose in many cases while affording minimal user discomfort.

Many analytes represent intriguing targets for physiological analyses, provided that a suitable detection chemistry can be identified. To this end, amperometric sensors configured for assaying glucose in vivo have been developed and refined over recent years to aid in monitoring the health of diabetic individuals. Other analytes commonly subject to concurrent dysregulation with glucose in diabetic individuals include, for example, lactate, oxygen, pH, A1c, ketones, and the like. Sensors configured for detecting analytes commonly dysregulated in combination with glucose are known but are considerably less refined at present.

In vivo analyte sensors typically are configured to analyze for a single analyte in order to provide specific analyses, oftentimes employing an enzyme to provide high specificity for a given analyte. Because of such analytical specificity, current in vivo analyte sensors configured for assaying glucose are generally ineffective for assaying other analytes that are frequently dysregulated in combination with glucose or resulting from dysregulated glucose levels. At best, current analyte monitoring approaches require a diabetic individual to wear two different in vivo analyte sensors, one configured for assaying glucose and the other configured for assaying another analyte of interest. Analyte monitoring approaches employing multiple in vivo analyte sensors may be highly inconvenient for a user. Moreover, when multiple in vivo analyte sensors are used for analyte monitoring, there is an added cost burden for equipment and an increased statistical likelihood for failure of at least one of the individual in vivo analyte sensors.

Diabetic individuals are often particularly susceptible to comorbid conditions, which may result from mismanagement of their insulin levels or even as a consequence of having well-managed diabetes over a long period of time. By way of example, diabetic neuropathy may result from high blood glucose levels and lead to eventual kidney failure. Diabetic neuropathy is the leading cause of kidney failure in the United States and is experienced by a significant number of diabetic individuals within the first 10-20 years of their disease. Diagnostic tests for evaluating kidney function are currently based upon measurement of elevated creatinine levels in blood and/or urine samples. Although it is desirable to detect potential kidney failure as soon as possible, current diagnostic testing approaches are usually conducted over an extended period of time (months to years) to verify that creatinine levels are persistently increased or are trending upward over time. The infrequency of conventional creatinine monitoring may increase the risk of kidney failure occurring if abnormal kidney function is not detected early enough.

Ethanol can also play an important role in diabetes management. As used herein, the term "ethanol" refers to the chemical compound $C_2H_6O$, and is an ingredient in alcoholic beverages; the terms "alcohol" and "ethanol" are used interchangeably herein, unless specified otherwise. Glucose homeostasis, the balance of insulin and glucagon to maintain blood glucose, is critical to the functioning of the central nervous system and various cellular systems that rely on such homeostasis for proper metabolism. Fluctuations in glucose homeostasis (i.e., hyperglycemia, an excess of blood glucose and hypoglycemia, a deficiency of blood glucose) can interfere with organ and cellular operation, at least by specifically interfering with insulin and glucose production, regulation, and action. For example, alcohol may inhibit the production of glucose in the liver, and thus its release therefrom, increasing the risk of moderate or severe hypoglycemia. Alcohol may also reduce the effectiveness of insulin, thereby increasing the risk of moderate or severe hyperglycemia. Thus, the relationship between alcohol and glucose may not directly correlate with each other, is individualistic in many respects (e.g., genetic predispositions), and dependent at least upon exposure time and concentration. Moreover, alcohol may impair an individual's ability to recognize or appreciate symptoms associated with hyperglycemia and hypoglycemia, thereby exacerbating the health risk to the individual. Knowledge of alcohol-induced alterations in the glycemic control of a diabetic individual, whose glucose levels are naturally dysregulated or otherwise lack homeostasis without intervention, can be of extreme benefit.

Ketones are another class of analytes that are commonly dysregulated in diabetic individuals. Because glucose and ketones concentrations may not directly correlate with each other in a diabetic individual also exhibiting ketoacidosis (ketone dysregulation), it may be advantageous to monitor both analytes concurrently, potentially leading to improved health outcomes. In addition to providing health benefits for diabetic individuals, the analyte sensors may be beneficial for other individuals who wish to monitor their ketones levels, such as individuals practicing a ketogenic diet. Ketogenic diets may be beneficial for promoting weight loss as well as helping epileptic individuals manage their condition. Concurrent glucose monitoring during ketogenic diet monitoring may offer related advantages.

Lactate is another analyte whose in vivo levels may vary in response to numerous environmental or physiological factors including, for example, eating, stress, exercise, sepsis or septic shock, infection, hypoxia, presence of cancerous tissue, and the like. In the case of chronic lactate-altering conditions (e.g., disease), lactate levels may change slowly, such that they may be readily quantified using conventional blood draws and laboratory measurements. Other lactate-altering conditions may be episodic in nature, in which case lactate levels may fluctuate very rapidly and irregularly. Conventional laboratory measurements may be ill suited to determine lactate levels in such instances. Namely, lactate levels may have changed several times between successive measurements, and an abnormal lactate level may be completely missed in such instances, thereby leading to potentially incorrect diagnoses. In the case of rapidly fluctuating lactate levels, it can be desirable to measure an individual's lactate levels continuously, such as through using an implanted in vivo lactate sensor. Continuous lactate monitoring can also be advantageous in individuals with chronic, slowly changing lactate levels as well. For example, continuous lactate monitoring can avoid the pain and expense associated with conducting multiple blood draws for assaying lactate levels.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 5E and 5F are pictures of electrodes before and after application of two membranes.

DETAILED DESCRIPTION

Figure 1:
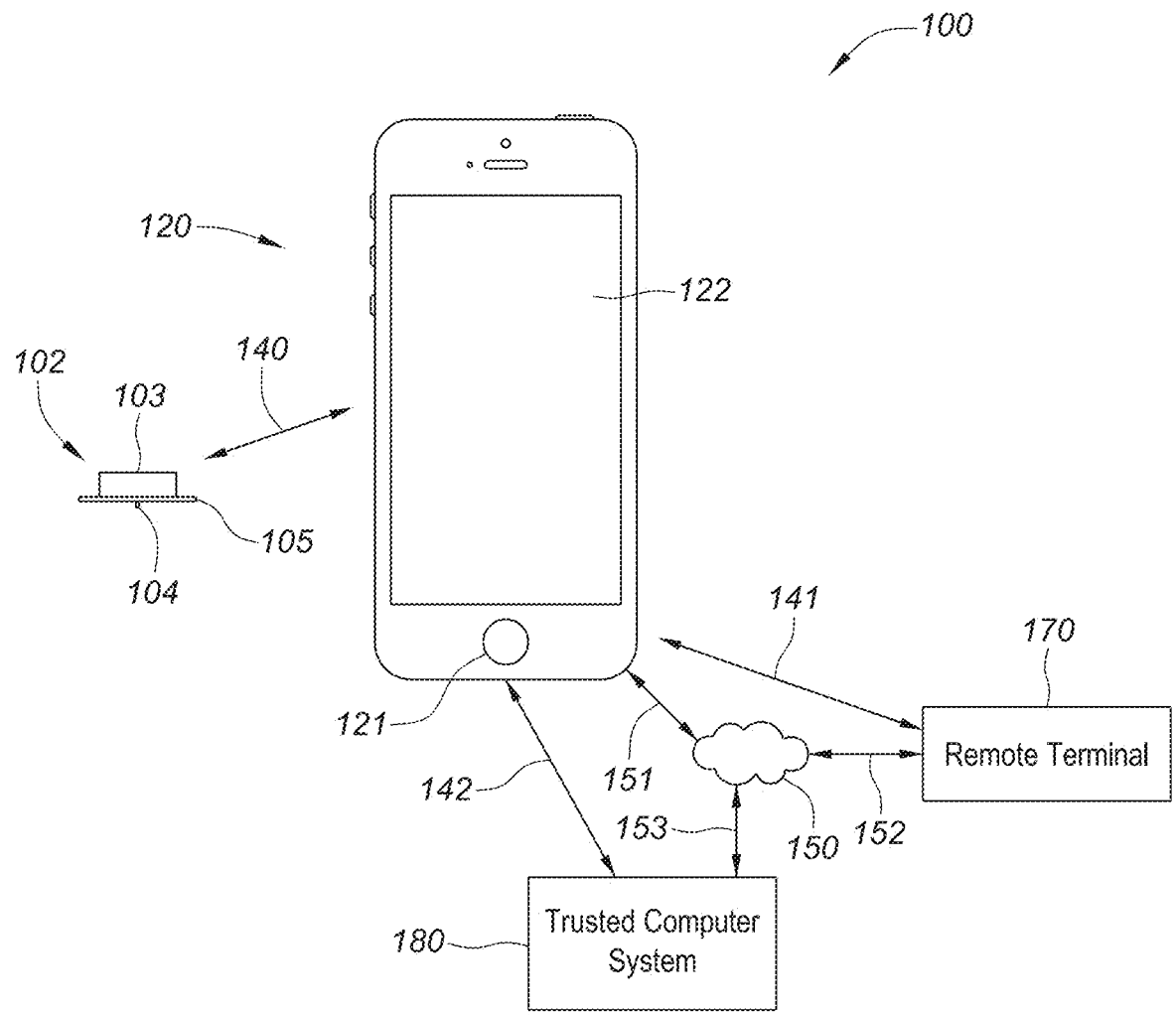
FIG. 1 shows a diagram of an illustrative sensing system that may incorporate an analyte sensor of the present disclosure.

The present disclosure generally describes analyte sensors employing multiple enzymes for detection of multiple analytes and, more specifically, analyte sensors employing multiple working electrodes for detecting multiple analytes, e.g., glucose, β-hydroxybutyrate, uric acid, ketone, creatinine, ethanol, and lactate. Multiple sensors may also be employed to analyze multiple analytes. In one embodiment, a sensor includes at least two working electrodes and counter/reference electrodes. In another embodiment, the analyte detection system may contain multiple sensors. The system may contain a primary sensor with at least one, optionally at least two, working electrodes, a counter electrode, and a reference electrode. The system may also contain a sub-sensor that contains at least one, optionally at least two, optionally at least three, optionally at least four working electrodes, and does not contain a counter or reference electrode. The sub-sensor is placed implanted into the user in close proximity to the primary sensor, such that the sub-sensor is able to share the counter and reference electrodes in the primary sensor. The sub-sensor may be contained in the same sensor housing as the primary sensor. Optionally the sub-sensor may be placed in a separate sensor housing that is in close proximity to the sensor housing of the primary sensor, such that the primary sensor and sub-sensor share the same counter and reference electrodes. In an alternative embodiment, multiple sub-sensors may share the counter and reference electrodes of the primary sensor.

As discussed above, analyte sensors employing an enzyme are commonly used to monitor a single analyte, such as glucose, due to the enzyme's frequent specificity for a particular substrate or class of substrate. Other analytes may be monitored as well, provided that suitable sensor configurations and suitable detection chemistry can be identified. The monitoring of multiple analytes is complicated by the need to employ a corresponding number of analyte sensors to detect each analyte separately. This approach may be problematic or undesirable, especially when monitoring multiple analytes in vivo, due to issues such as, for example, the cost of multiple analyte sensors, user discomfort when wearing multiple analyte sensors, and an increased statistical likelihood for failure of an individual analyte sensor.

Glucose-responsive analyte sensors are a well-studied and still developing field to aid diabetic individuals in better managing their health. Despite the prevalence of comorbid conditions in diabetic individuals, sensor chemistries suitable for in vivo monitoring of other analytes commonly dysregulated in combination with glucose have significantly lagged behind the more well-developed glucose detection chemistry. For example, in addition to glucose, creatinine, lactate, ketones, and ethanol may all be of particular interest for monitoring in diabetic individuals.

The present disclosure provides analyte sensors and sensor systems that are responsive to at least two analytes. Specifically, the present disclosure provides analyte sensors that are capable of being worn on-body for in vivo monitoring the levels of at least two analytes continuously or near-continuously. Analysis of the levels of the at least two analytes with the analyte sensors disclosed herein may provide an individual or health care provider a more accurate representation of various conditions over an extended period of time than is possible with periodic, ex vivo laboratory measurements. For instance, by analyzing creatinine levels according to the present disclosure, earlier health care intervention may be possible to limit potential kidney damage and improve overall health outcomes for an individual.

The present disclosure provides for monitoring at least two analytes, e.g., both glucose and another analyte, using one or more in vivo analyte sensors responsive to each analyte, and in particularly advantageous configurations, a single analyte sensor that is responsive to both analytes in vivo may be used. Advantageously and surprisingly, analyte sensors incorporating sensing functionality for both glucose and another upon a single sensor tail may be fabricated by employing the disclosure herein.

Before describing the analyte sensors of the present disclosure in further detail, a brief overview of suitable in vivo analyte sensor configurations and sensor systems employing the analyte sensors will be provided first so that the embodiments of the present disclosure may be better understood. FIG. 1 shows a diagram of an illustrative sensing system that may incorporate an analyte sensor of the present disclosure, specifically an analyte sensor capable of monitoring multiple analytes. As shown, sensing system 100 includes sensor control device 102 and reader device 120 that are configured to communicate with one another over a local communication path or link, which may be wired or wireless, uni- or bi-directional, and encrypted or non-encrypted. Reader device 120 may constitute an output medium for viewing analyte concentrations and alerts or notifications determined by sensor 104 or a processor associated therewith, as well as allowing for one or more user inputs, according to some embodiments. Reader device 120 may be a multi-purpose smartphone or a dedicated electronic reader instrument. While only one reader device 120 is shown, multiple reader devices 120 may be present in certain instances. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also or alternately be in communication with network 150 (e.g., a mobile telephone network, the internet, or a cloud server) via communication path/link 151. Network 150 may be further communicatively coupled to remote terminal 170 via communication path/link 152 and/or trusted computer system 180 via communication path/link 153. Alternately, sensor 104 may communicate directly with remote terminal 170 and/or trusted computer system 180 without an intervening reader device 120 being present. For example, sensor 104 may communicate with remote terminal 170 and/or trusted computer system 180 through a direct communication link to network 150, according to some embodiments, as described in U.S. Patent Application Publication 2011/0213225 and incorporated herein by reference in its entirety. Any suitable electronic communication protocol may be used for each of the communication paths or links, such as near field communication (NFC), radio frequency identification (RFID), BLUETOOTH® or BLUETOOTH® Low Energy protocols, WiFi, or the like. Remote terminal 170 and/or trusted computer system 180 may be accessible, according to some embodiments, by individuals other than a primary user who have an interest in the user's analyte levels. Reader device 120 may comprise display 122 and optional input component 121. Display 122 may comprise a touch-screen interface, according to some embodiments.

Sensor control device 102 includes sensor housing 103, which may house circuitry and a power source for operating sensor 104. Optionally, the power source and/or active circuitry may be omitted. A processor (not shown) may be communicatively coupled to sensor 104, with the processor being physically located within sensor housing 103 or reader device 120. Sensor 104 protrudes from the underside of sensor housing 103 and extends through adhesive layer 105, which is adapted for adhering sensor housing 103 to a tissue surface, such as skin, according to some embodiments.

Sensor 104 is adapted to be at least partially inserted into a tissue of interest, such as within the dermal or subcutaneous layer of the skin. Sensor 104 may comprise a sensor tail of sufficient length for insertion to a desired depth in a given tissue. The sensor tail may comprise at least one working electrode and a first analyte-responsive active area disposed thereon. Optionally, a second analyte-responsive active area, further optionally in combination with a second working electrode, may be located upon the sensor tail to facilitate detection of this analyte. A counter electrode may be present in combination with the at least one working electrode. Particular electrode configurations upon the sensor tail are described in more detail below in reference to FIGS. 2-5 and 11.

Referring still to FIG. 1, sensor 104 may automatically forward data to reader device 120. For example, analyte concentration data may be communicated automatically and periodically, such as at a certain frequency as data is obtained or after a certain time period has passed, with the data being stored in a memory until transmittal (e.g., every minute, five minutes, or other predetermined time period). In other embodiments, sensor 104 may communicate with reader device 120 in a non-automatic manner and not according to a set schedule. For example, data may be communicated from sensor 104 using RFID technology when the sensor electronics are brought into communication range of reader device 120. Until communicated to reader device 120, data may remain stored in a memory of sensor 104. Thus, a user does not have to maintain close proximity to reader device 120 at all times, and can instead upload data at a convenient time. In yet other embodiments, a combination of automatic and non-automatic data transfer may be implemented. For example, data transfer may continue on an automatic basis until reader device 120 is no longer in communication range of sensor 104.

An introducer may be present transiently to promote introduction of sensor 104 into a tissue. In illustrative embodiments, the introducer may comprise a needle or similar sharp. It is to be recognized that other types of introducers, such as sheaths or blades, may be present in alternative embodiments. More specifically, the needle or other introducer may transiently reside in proximity to sensor 104 prior to tissue insertion and then be withdrawn afterward. While present, the needle or other introducer may facilitate insertion of sensor 104 into a tissue by opening an access pathway for sensor 104 to follow. For example, the needle may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, suitable needles may be solid or hollow, beveled or non-beveled, and/or circular or non-circular in cross-section. In more particular embodiments, suitable needles may be comparable in cross-sectional diameter and/or tip design to an acupuncture needle, which may have a cross-sectional diameter of about 250 microns. It is to be recognized, however, that suitable needles may have a larger or smaller cross-sectional diameter if needed for particular applications.

In some embodiments, a tip of the needle (while present) may be angled over the terminus of sensor 104, such that the needle penetrates a tissue first and opens an access pathway for sensor 104. In other illustrative embodiments, sensor 104 may reside within a lumen or groove of the needle, with the needle similarly opening an access pathway for sensor 104. In either case, the needle is subsequently withdrawn after facilitating sensor insertion.

Figure 2A:
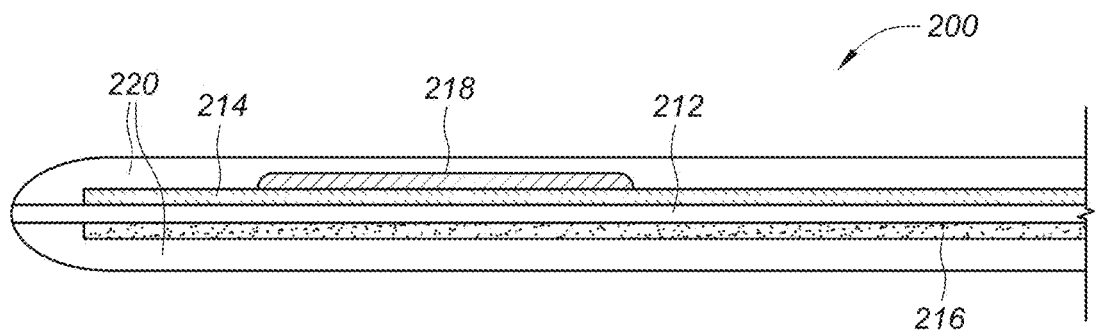
FIGS. 2A-2B show cross-sectional diagrams of illustrative two-electrode analyte sensor configuration having a single working electrode.
Figure 2B:
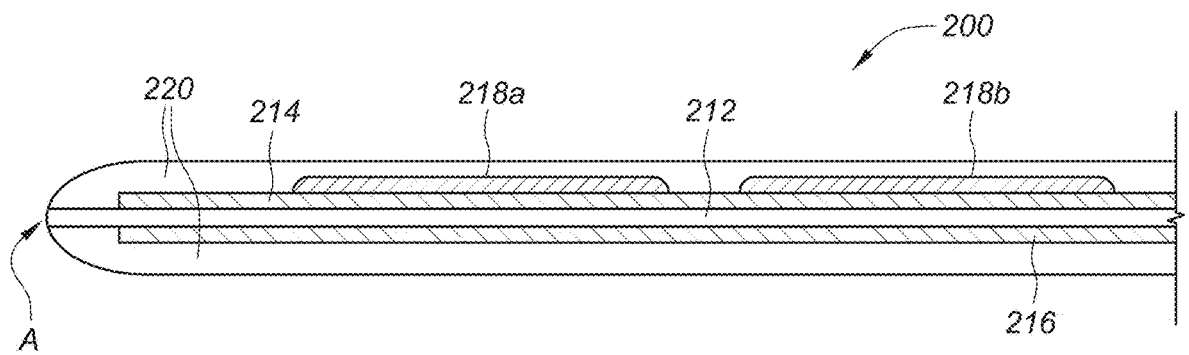

The analyte sensors disclosed herein may feature active areas of different types (e.g, a glucose-responsive active area and a ketones-, lactate-, creatinine-, or ethanol-responsive active area) upon a single working electrode or upon two or more separate working electrodes. Single working electrode sensor configurations may employ two-electrode or three-electrode detection motifs, according to various embodiments of the present disclosure and as described further herein. FIG. 2A-2B shows a cross-sectional diagram of an illustrative two-electrode analyte sensor configuration having a single working electrode, which is compatible for use in some embodiments of the disclosure herein. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). FIG. 2A shows a single active area 218. Multiple active areas 218a and 218b (i.e., a glucose-responsive active area and a ketones-responsive active area) are laterally spaced apart from one another upon the surface of working electrode 214. In the various sensor configurations shown herein, active areas 218a and 218b may comprise multiple spots or a single spot configured for detection of each analyte. Analyte sensor 200 may be operable for assaying glucose and ketones by any of coulometric, amperometric, voltammetric, or potentiometric electrochemical detection techniques.

When a single working electrode is present in an analyte sensor, three-electrode sensor configurations may comprise a working electrode, a counter electrode, and a reference electrode. (See FIGS. 2A and 2B). Related two-electrode sensor configurations may comprise a working electrode and a second electrode, in which the second electrode may function as both a counter electrode and a reference electrode (i.e., a counter/reference electrode). In both two-electrode and three-electrode sensor configurations, both the first analyte-responsive active area and the second analyte-responsive active area may be disposed upon the single working electrode. In some embodiments, the various electrodes may be at least partially stacked (layered) upon one another and/or laterally spaced apart from one another upon the sensor tail. Suitable sensor configurations may be substantially flat in shape or substantially cylindrical in shape, with the first analyte-responsive active area and the second analyte-responsive active area being laterally spaced apart upon the working electrode. In all of the sensor configurations disclosed herein, the various electrodes may be electrically isolated from one another by a dielectric material or similar insulator.

Analyte sensors featuring multiple working electrodes may similarly comprise at least one additional electrode. When one additional electrode is present, the one additional electrode may function as a counter/reference electrode for each of the multiple working electrodes. When two additional electrodes are present, one of the additional electrodes may function as a counter electrode for each of the multiple working electrodes and the other of the additional electrodes may function as a reference electrode for each of the multiple working electrodes.

Analyte sensor configurations having a single working electrode will now be described in further detail. FIG. 2A shows a cross-sectional diagram of an illustrative two-electrode analyte sensor configuration having a single working electrode, which is compatible for use in some embodiments of the disclosure herein. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Active area 218 is disposed on working electrode 214. As seen in FIG. 2B, where multiple active areas are present on a single working electrode 214, active areas 218a and 218b (e.g., a glucose-responsive active area and a ketones-responsive active area) are laterally spaced apart from one another upon the surface of working electrode 214. In the various sensor configurations shown herein, active areas 218a and 218b may comprise multiple spots or a single spot configured for detection of each analyte. Analyte sensor 200 may be operable for assaying glucose and ketones by any of coulometric, amperometric, voltammetric, or potentiometric electrochemical detection techniques.

Figure 3A:
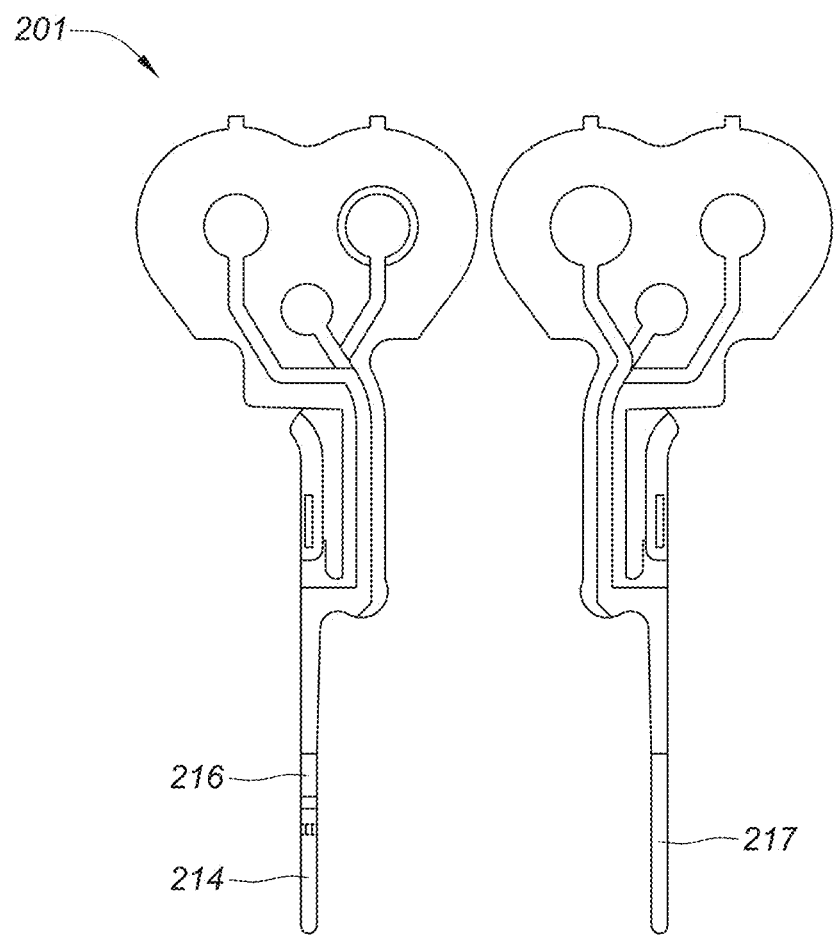
FIG. 3A shows plan views of both sides of an illustrative analyte sensor having a single working electrode.
Figure 3B:
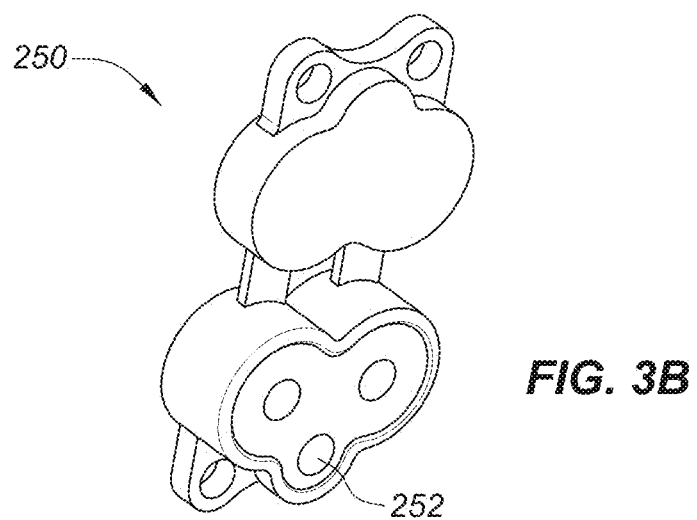
FIG. 3B shows a perspective view of an illustrative connector.
Figure 3C:
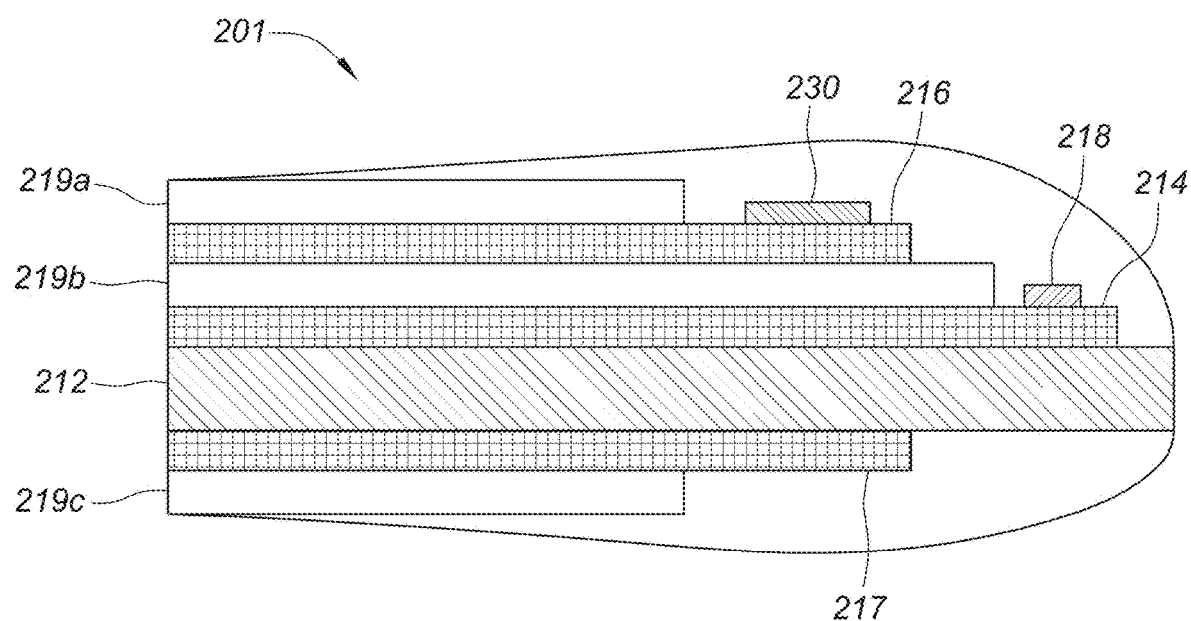
FIG. 3C shows a cross-sectional diagram of an illustrative three-electrode analyte sensor configuration having a single working electrode.

A sensor that monitors a single analyte with a single working electrode is depicted in FIG. 3A. Three electrodes are screen printed on both sides of a substrate (e.g., PET substrate) with an insulation layer in between. As seen in FIG. 3C, analyte sensor 201 comprises substrate 212 disposed between working electrode 214 and counter electrode 217. Alternately, working electrode 214 may be located on the same side of substrate 212 as counter electrode 217 with a dielectric material interposed in between (configuration not shown). Reference electrode 216 is electrically isolated from working electrode 214 by dielectric layer 219b. Outer dielectric layers 219a and 219c are positioned on reference electrode 216 and counter electrode 217. Analyte-specific responsive active area 218, e.g., a glucose-responsive, creatine-response, or lactate-responsive active area), may be disposed as at least one layer upon at least a portion of working electrode 214. The analyte-responsive active area (s) may comprise multiple spots/area or a single spot/area configured for detection of the analyte, as discussed further herein. Reference material layer 230 (e.g., Ag/AgCl) may be present upon reference electrode 216, with the location of reference material layer 230 not being limited to that depicted in FIG. 3C. As seen in FIG. 3B, connector 250 contains three openings 252 to allow connections between the working, counter, and reference electrodes with the printed circuit board (not shown).

Figure 4A:
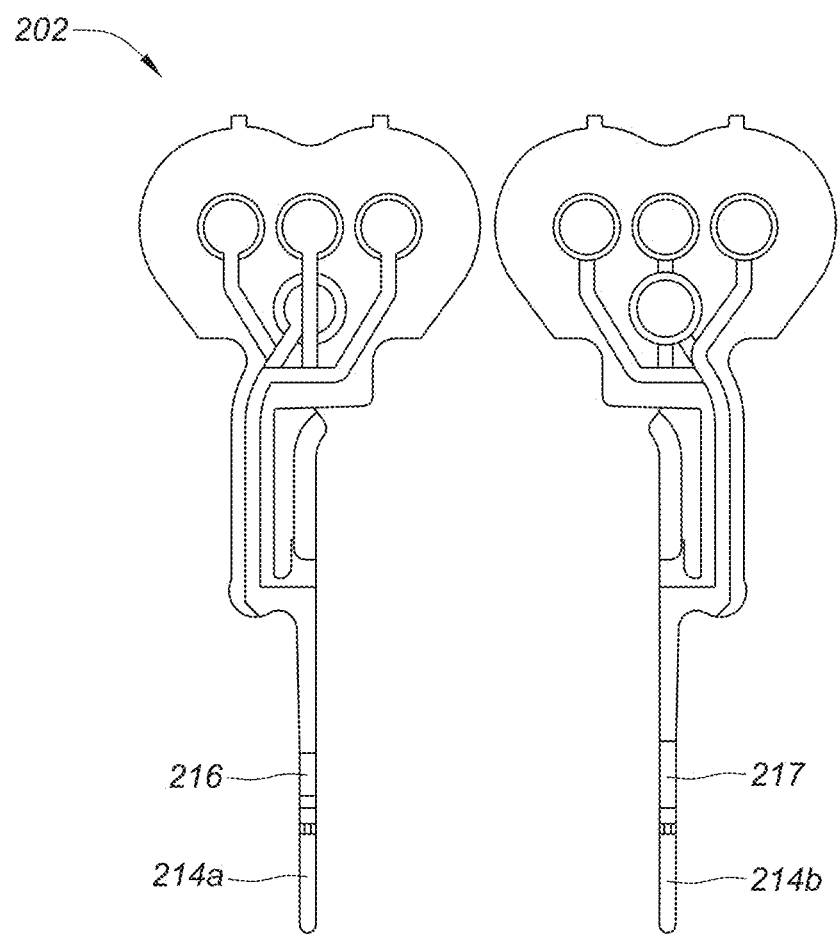
FIG. 4A shows plan views of both sides of an illustrative analyte sensor configuration having two working electrodes.
Figure 4B:
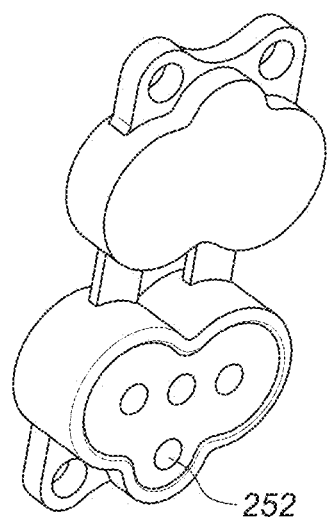
FIG. 4B shows a perspective view of an illustrative connector.

A sensor monitoring two analytes with two working electrodes is depicted in FIG. 4A. In this embodiment, four electrodes are screen printed on both sides of a substrate (e.g., PET substrate) with insulation layers to electrically isolate the electrodes. As seen in FIG. 4A, working electrode 214a and reference electrode 216 are printed on one side and working electrode 214b and counter electrode 217 are printed on the other side. As seen in FIG. 4B, connector 250 contains four openings 252 to allow connections between the two working, counter, and reference electrodes with the printed circuit board (not shown).

Figure 5A:
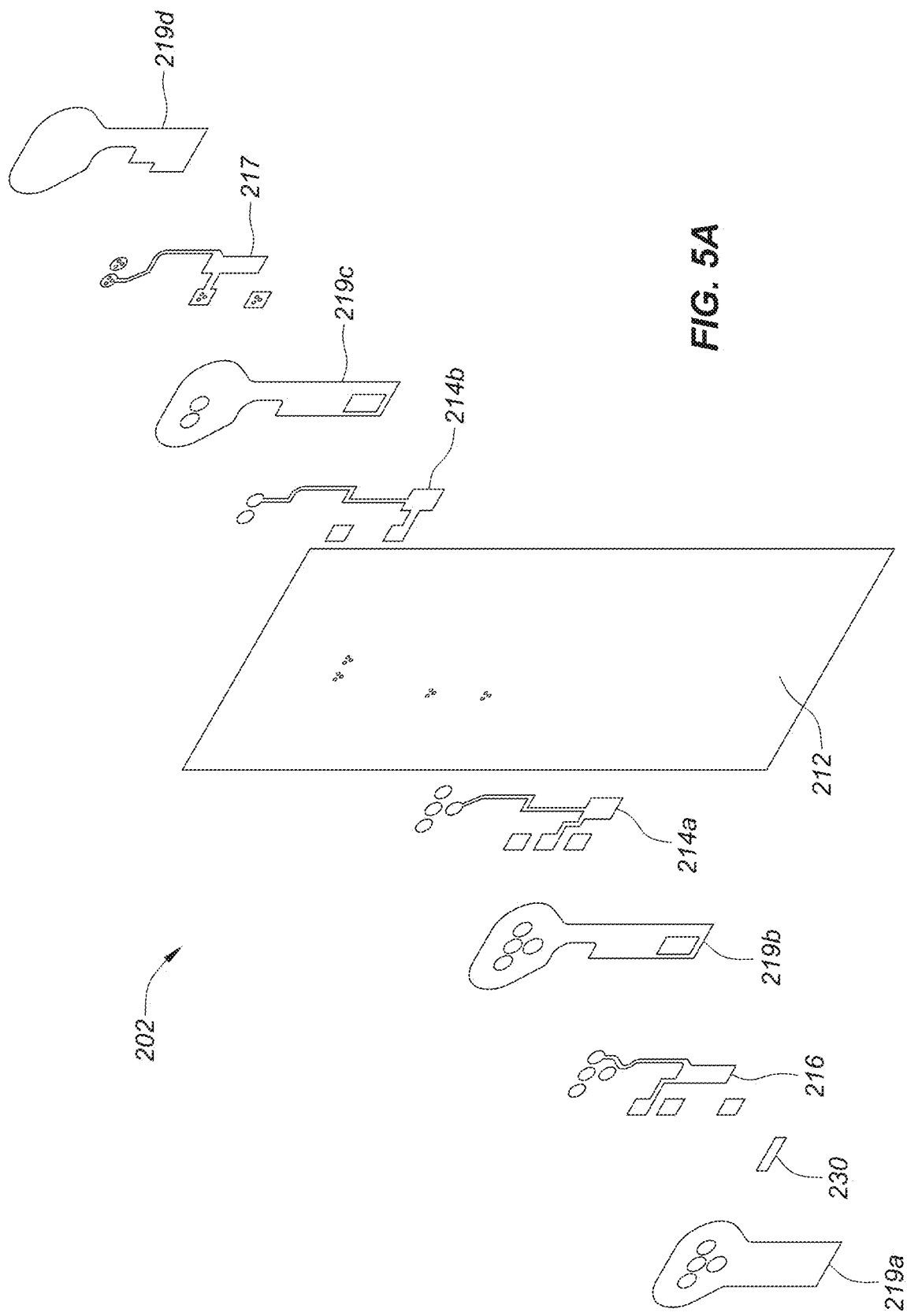
FIG. 5A shows an exploded view of an illustrative analyte sensor configuration having two working, a counter, and a reference electrode.
Figure 5B:
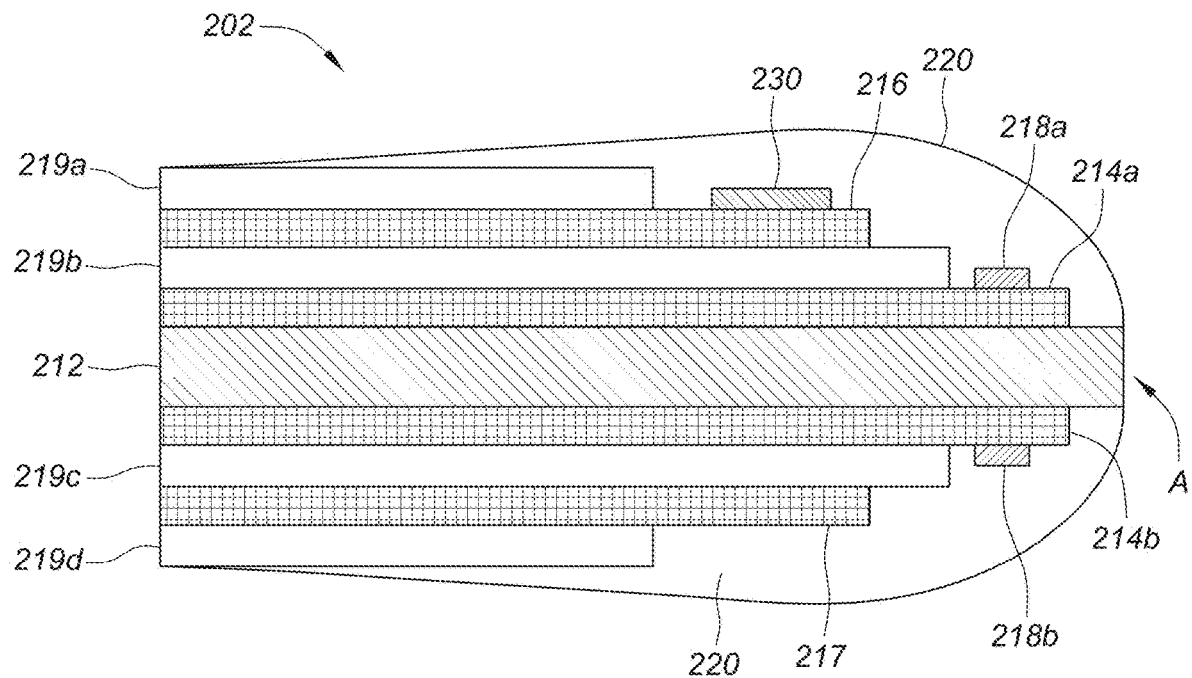
FIG. 5B shows a cross-sectional diagram of an illustrative analyte sensor configuration having two working, a counter, and a reference electrode.

FIGS. 5A and 5B show diagrams of an illustrative four-electrode analyte sensor configuration, which is compatible for use in the disclosure herein. As shown, analyte sensor 201 comprises substrate 212 disposed between working electrodes 214a and 214b. Alternately, working electrodes 214a and 214b may be located on the same side of substrate 212 with a dielectric material interposed in between (configuration not shown). Analyte-specific responsive active areas 218a and/or 218b, e.g., a glucose-responsive, creatine-response, or lactate-responsive active area), may be disposed as at least one layer upon at least a portion of working electrodes 214a and/or 214b. The analyte-responsive active area(s) may comprise multiple spots/area or a single spot/area configured for detection of the analyte, as discussed further herein. A reference electrode may be disposed upon either working electrodes 214a or 214b, with a separating layer of dielectric material in between. A counter electrode may be disposed on the other of working electrodes 214a or 214b, with a separating layer of dielectric material in between. For example, as depicted in FIG. 5B, dielectric layers 219b and 219c separate electrodes 214a, 214b, 216 and 217 from one another and provide electrical isolation. Outer dielectric layers 219a and 219d are positioned on reference electrode 216 and counter electrode 217.

Alternately, at least one of electrodes 214a, 214b, 216 and 217 may be located upon opposite faces of substrate 212. Thus, in some embodiments, electrode 214a (working electrode) and electrode 216 (counter electrode) may be located upon opposite faces of substrate 212 as electrode 217 (reference electrode), with working electrode 214b being located on the opposite face of the substrate. Reference material layer 230 (e.g., Ag/AgCl) may be present upon reference electrode 216, with the location of reference material layer 230 not being limited to that depicted in FIG. 5A. As with sensor 202 shown in FIG. 5B, analyte-responsive active area 218 in analyte sensor 202 may comprise multiple spots or a single spot. Additionally, analyte sensor 202 may be operable for assaying the analyte by any of coulometric, amperometric, voltammetric, or potentiometric electrochemical detection techniques. Although FIG. 5B has depicted all of electrodes 214a, 214b, 216 and 217 as being overcoated with membrane 220, it is to be recognized that only working electrodes 214a and 214b may be overcoated in some embodiments. Moreover, the thickness of membrane 220 at each of electrodes 214a, 214b, 216 and 217 may be the same or different. As in two-electrode analyte sensor configurations (e.g., FIGS. 2A and 2B), one or both faces of analyte sensor 202 may be overcoated with membrane 220 in the sensor configurations of FIG. 5A, or the entirety of analyte sensors 202 may be overcoated. Accordingly, the multiple-electrode sensor configuration shown in FIGS. 5A and 5B should be understood as being non-limiting of the embodiments disclosed herein, with alternative electrode and/or layer configurations remaining within the scope of the present disclosure.

Referring still to FIG. 5B, membrane 220 optionally overcoats at least analyte-responsive active areas 218a and 218b and overcoats some or all of working electrodes 214a and/or 214b and/or reference electrode 216 and/or counter electrode 217, or the entirety of analyte sensor 202 according to some embodiments. One or both faces of analyte sensor 202 may be overcoated with membrane 220. Membrane 220 may comprise one or more polymeric membrane materials having capabilities of limiting analyte flux to active area 218 (i.e., membrane 220 is a mass transport limiting membrane having some permeability for the analyte (s) being measured). The composition and thickness of membrane 220 may vary to promote a desired analyte flux to analyte-responsive active areas 218a, 218b, thereby providing a desired signal intensity and stability. Analyte sensor 200 may be operable for assaying the analyte(s) by any of coulometric, amperometric, voltammetric, or potentiometric electrochemical detection techniques.

Figure 5C:
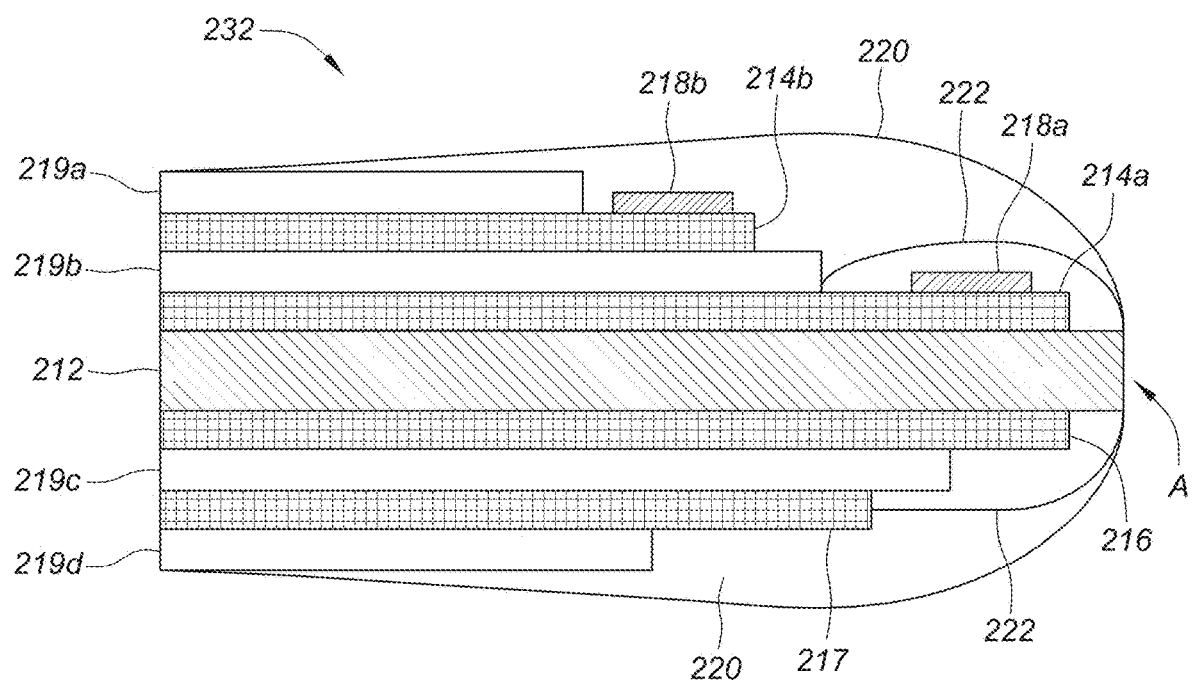
FIG. 5C shows a cross-sectional diagram of an illustrative analyte sensor configuration having two working, a counter, and a reference electrode.

FIG. 5C shows a diagram of an illustrative four-electrode analyte sensor configuration, which is compatible for use in the disclosure herein. As shown, analyte sensor 232 comprises substrate 212 disposed between working electrode 214a and counter electrode 216. Working electrodes 214a and 214b are located on the same side of substrate 212 with a dielectric material 219b interposed in between). Counter electrode 216 and reference electrode 217 are located on the opposite side of substrate 212 with a dielectric material 219c interposed in between. Analyte-specific responsive active area 218a (e.g., ketone responsive active area) may be disposed as at least one layer upon at least a portion of working electrode 214a. Analyte-specific responsive active area 218b (e.g., a glucose-responsive) may be disposed as at least one layer upon at least a portion of working electrode 214b. Active area 218a (e.g., ketone responsive active area) may be located closer to end A than analyte-specific responsive active area 218b (e.g., a glucose-responsive). The analyte-responsive active area(s) may comprise multiple spots/area or a single spot/area configured for detection of the analyte, as discussed further herein. As depicted in FIG. 5C, dielectric layers 219b and 219c separate electrodes 214a, 214b, 216 and 217 from one another and provide electrical isolation. Outer dielectric layers 219a and 219d are positioned on working electrode 214b and counter electrode 217. Reference material layer 230 (e.g., Ag/AgCl) (not shown) may be present upon reference electrode 216, or another suitable location on the sensor. As with sensors 202, 232 shown in FIGS. 5B and 5C, analyte-responsive active area 218 in analyte sensors 202, 232 may comprise multiple spots or a single spot. Additionally, analyte sensors 202, 232 may be operable for assaying the analyte by any of coulometric, amperometric, voltammetric, or potentiometric electrochemical detection techniques.

Figure 5D:
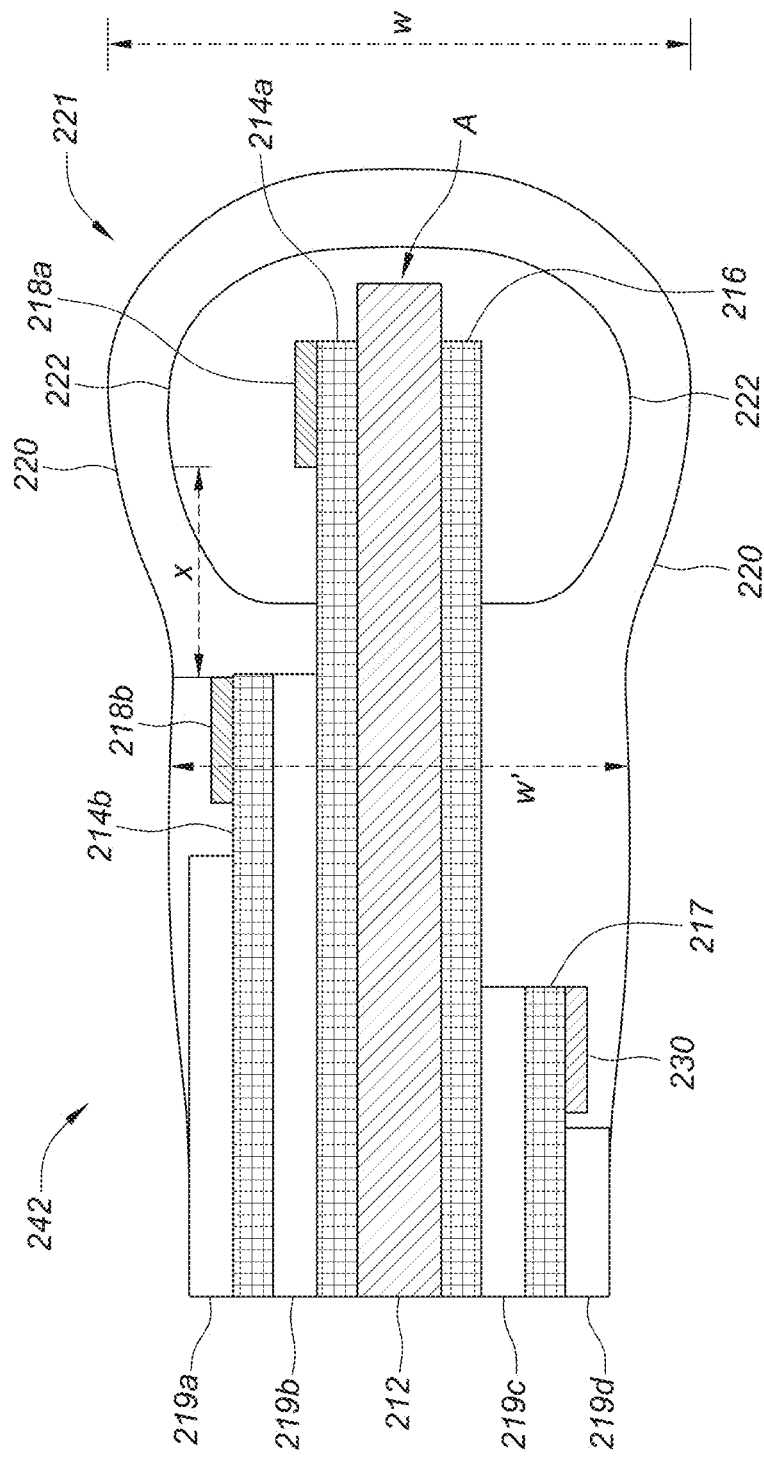
FIG. 5D shows a cross-sectional diagram of an illustrative analyte sensor configuration having two working, a counter, and a reference electrode.

FIG. 5D shows a diagram of an illustrative four-electrode analyte sensor configuration, which is compatible for use in the disclosure herein. As shown, analyte sensor 242 comprises substrate 212 disposed between working electrode 214a and counter electrode 216. Working electrodes 214a and 214b are located on the same side of substrate 212 with a dielectric material 219b interposed in between). Counter electrode 216 and reference electrode 217 are located on the opposite side of substrate 212 with a dielectric material 219c interposed in between. Analyte-specific responsive active area 218a (e.g., ketone responsive active area) may be disposed as at least one layer upon at least a portion of working electrode 214a. Analyte-specific responsive active area 218b (e.g., a glucose-responsive) may be disposed as at least one layer upon at least a portion of working electrode 214b. Active area 218a (e.g., ketone responsive active area) may be located closer to end A than analyte-specific responsive active area 218b (e.g., a glucose-responsive). The analyte-responsive active area(s) may comprise multiple spots/area or a single spot/area configured for detection of the analyte, as discussed further herein. As depicted in FIG. 5C, dielectric layers 219b and 219c separate electrodes 214a, 214b, 216 and 217 from one another and provide electrical isolation. Outer dielectric layers 219a and 219d are positioned on working electrode 214b and counter electrode 217. Reference material layer 230 (e.g., Ag/AgCl) may be present upon reference electrode 216, or another suitable location on the sensor. As with sensors 202, 232, 242 shown in FIGS. 5B-5D, analyte-responsive active areas 218a, 218b in analyte sensors 202, 232, 242 may comprise multiple spots or a single spot. Additionally, analyte sensors 202, 232, 242 may be operable for assaying the analyte by any of coulometric, amperometric, voltammetric, or potentiometric electrochemical detection techniques.

Active area 218a may be closer to end A (distal end of sensor that is inserted into a subject) than active area 218b. Active area 218a may have a length of between about 0.7 mm to about 1.3 mm, alternatively between about 0.8 mm to about 1.2 mm, alternatively between about 0.9 mm to about 1.1 mm, alternatively about 0.8 mm, alternatively about 0.9 mm, alternatively about 1.0 mm, alternatively about 1.1 mm, alternatively about 1.2 mm. Active area 218b may have a length that is longer than a length of active area 218a. Active area 218b may have a length of between about 0.7 mm to about 1.5 mm, alternatively between about 0.8 mm to about 1.4 mm, alternatively between about 0.9 mm to about 1.3 mm, alternatively about 0.8 mm, alternatively about 0.9 mm, alternatively about 1.0 mm, alternatively about 1.1 mm, alternatively about 1.2 mm, alternatively about 1.3 mm, alternatively about 1.4 mm. Active areas 218a and 218b may be separated by a distance x (e.g., a proximal end of active area 218a may be separated from a distal end of active area 218b) by between about 0.4 mm to about 1.1 mm, alternatively about 0.5 to about 1.0 mm, alternatively between about 0.6 to about 0.9 mm, between about 0.7 to about 0.9 mm, alternatively by about 0.4 mm, alternatively by about 0.5 mm, alternatively by about 0.6 mm, alternatively by about 0.7 mm, alternatively by about 0.8 mm, alternatively by about 0.9 mm, alternatively by about 1.0 mm, alternatively at least about 0.2 mm, alternatively at least about 0.4 mm, alternatively at least about 0.6 mm, alternatively at least about 0.8 mm.

Sensors 232, 242 may contain two membranes 220, 222. As seen in FIGS. 5C and 5D, membrane 222 may only cover a portion of working electrode 214a, which includes active area 218a (e.g., ketone responsive active area). Membrane 220 may cover both active area 218a (e.g., ketone responsive active area) and active area 218b (e.g., a glucose-responsive). Membrane 220 may also cover counter electrode 216 and reference electrode 217 on the opposite side of substrate 212. Thus, active area 218a (e.g., ketone responsive active area) may have a bilayer membrane that includes membranes 222 and 220, while active area 218b may only have a single layer membrane 220. Although FIGS. 5C and 5D have depicted all of electrodes 214a, 214b, 216 and 217 as being overcoated with membrane 220, it is to be recognized that only working electrodes 214a and 214b may be overcoated in some embodiments. Moreover, the thickness of membranes 220, 222 at each of electrodes 214a, 214b, 216 and 217 may be the same or different. As in two-electrode analyte sensor configurations (e.g., FIGS. 2A and 2B), one or both faces of analyte sensor 202 may be overcoated with membrane 220 in the sensor configurations of FIG. 5A, or the entirety of analyte sensors 202 may be overcoated. Accordingly, the multiple-electrode sensor configuration shown in FIGS. 5A and 5B should be understood as being non-limiting of the embodiments disclosed herein, with alternative electrode and/or layer configurations remaining within the scope of the present disclosure.

Referring still to FIGS. 5C and 5D, membrane 222 optionally overcoats only active area 218a (e.g., ketone responsive active area) and does not overcoat active area 218b (e.g., a glucose-responsive). Membrane 220 optionally overcoats at least analyte-responsive active areas 218a and 218b and overcoats some or all of working electrodes 214a and/or 214b and/or reference electrode 216 and/or counter electrode 217, or the entirety of analyte sensor 202 according to some embodiments. Membrane 220 may comprise one or more polymeric membrane materials having capabilities of limiting analyte flux to active area 218 (i.e., membrane 220 is a mass transport limiting membrane having some permeability for the analyte(s) being measured). The composition and thickness of membrane 220 may vary to promote a desired analyte flux to analyte-responsive active areas 218a, 218b, thereby providing a desired signal intensity and stability. As seen in FIG. 5D, the distal region 221 of sensor 242 may be thicker or bulbous in shape as compared to a proximal region of the sensor tail (compare thickness w to w'). The distal region 221 of sensor 242 may have a thickness of between about 0.008" and about 0.014", alternatively between about 0.009" and about 0.013", alternatively between about 0.010" and about 0.013", alternatively between about 0.010" and about 0.012", alternatively between about 0.15 mm and about 0.4 mm, alternatively between about 0.2 mm and about 0.4 mm, alternatively between about 0.25 mm and about 0.4 mm, alternatively between about 0.25 mm and about 0.35 mm. Analyte sensors may be operable for assaying the analyte(s) by any of coulometric, amperometric, voltammetric, or potentiometric electrochemical detection techniques.

Membrane 222 may be dip coated onto active area 218a (e.g., ketone responsive active area). For example, sensor 232 may be partially dipped into a membrane solution such that only an end region near end A, which includes active area 218a and does not include active area 218b, is submerged into the membrane solution. The application of membrane 222 may be accomplished in a single dip procedure or may require multiple dips into the membrane solution to obtain a dense membrane. A larger portion of sensor 232, 242, which includes both active areas 218a and 218b, may then be submerged into a different membrane solution. Thus, active area 218a, which is located closer to a distal end A, may have a bilayer membrane, while active area 218b, which is proximal relative to active area 218a, would have a single layer membrane. Dip coating in this manner has numerous advantages. First, dispensing both sensing layers on one side of substrate 212 without needing to flip the substrate 212 simplifies the manufacturing process and improves efficiency. Second, this dipping method allows for use of the same membrane dipping equipment to be used for both membranes 222, 220, by simply exchanging out the membrane solutions and adjusting dipping depth.

FIG. 5E shows a sensor with a ketone active site 218a (with two spots) on a front side closer to the distal end A of the sensor, and a glucose active site 218b (with two spots) on a back side of the sensor located a farther distance from the distal end A than ketone active site 218a. The sensor in FIG. 5E has not yet been overcoated with a membrane. As seen in FIG. 5F (see dotted line), in the first dip, the sensor is dipped to a position between the ketone active site 218a and the glucose active site 218b, such that the ketone active site 218a is dipped into the membrane solution but not the glucose active site 218b. After optional multiple dips into the first membrane solution and curing, the sensor is then dipped into the second solution such that the sensor is dipped to a location proximal or above the glucose active site 218b such that both the ketone active site 218a and glucose active site 218b are submerged. As seen in the side view of FIG. 5F, the distal region 221 which has a bilayer membrane has the shape of a bulbous or widened tip having a thickness w, which is larger than a proximal region of the sensor tail having a thickness w', where only a single membrane overcoats the sensor. The thickness w may be between about 0.008" and about 0.014", alternatively between about 0.009" and about 0.013", alternatively between about 0.010" and about 0.013", alternatively between about 0.010" and about 0.012", alternatively between about 0.15 mm and about 0.4 mm, alternatively between about 0.2 mm and about 0.4 mm, alternatively between about 0.3 mm and about 0.4 mm, alternatively between about 0.25 mm and about 0.35 mm. In comparison, thickness w' may be between about 0.005" and about 0.01", alternatively between about 0.005" and about 0.009", alternatively between about 0.006" and about 0.009", alternatively between about 0.006" and about 0.008," alternatively between about 0.007" and about 0.008", alternatively between about 0.1 mm and about 0.3 mm, alternatively between about 0.1 mm and about 0.25 mm, alternatively between about 0.15 mm and about 0.25 mm. The difference between w and w' may be between about 0.003" to about 0.005", alternatively between about 0.003" to about 0.004", alternatively between about 0.05 mm to about 0.15 mm, alternatively between about 0.07 mm to about 0.1 mm, alternatively between about 0.075 mm to about 0.125 mm.

Figure 5G:
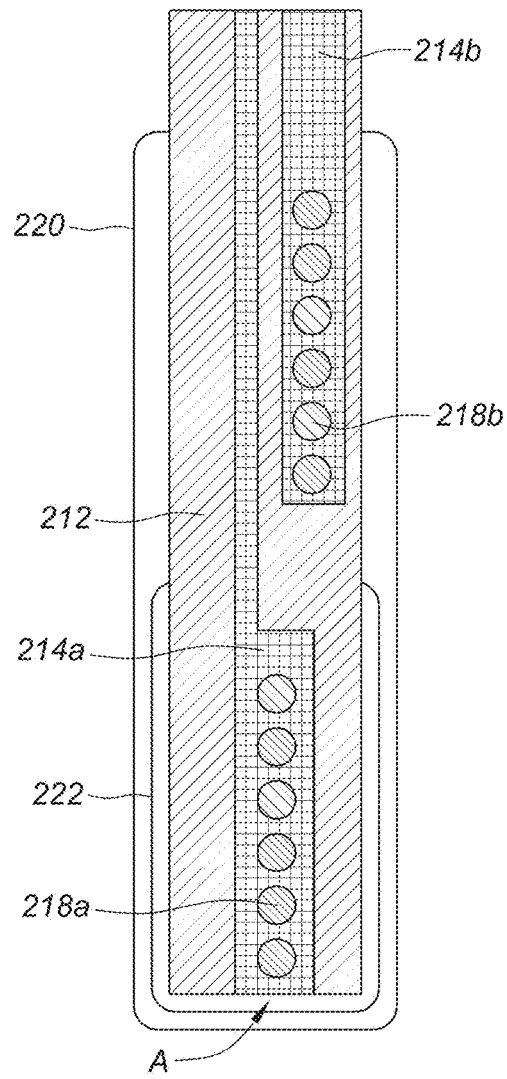
FIG. 5G shows a top view diagram of an analyte sensor having first and second working electrodes located on and in contact with the same surface of a substrate.
Figure 5H:
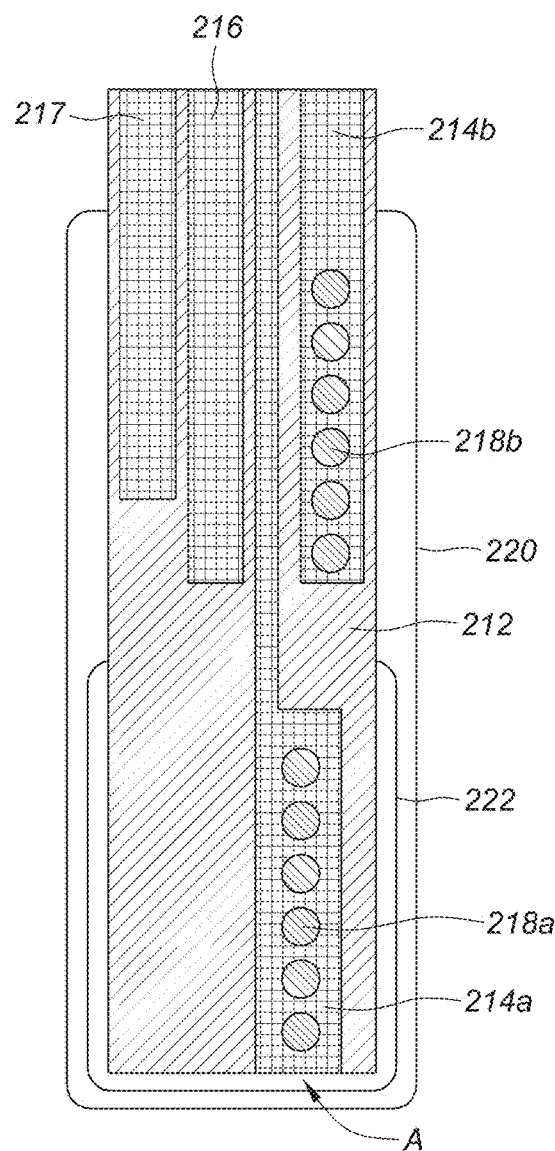
FIG. 5H shows a top view diagram of an analyte sensor having first and second working electrodes, a counter electrode, and a reference electrode located on and in contact with the same surface of a substrate.

In another embodiment, as seen in FIGS. 5G and 5H, the first 214a and second 214b working electrodes may be located on the same side of the substrate 212 and may be placed directly on the surface of the substrate 212 such that a dielectric layer(s) or insulating layer does not separate the first 214a and second 214b electrodes from the same substrate surface. Moreover, the first 214a and second 214b working electrodes are not stacked on top of each other, separated by a dielectric layer. Rather, the first 214a and second 214b working electrodes are spatially separated on the same surface of the substrate. Such an arrangement may simplify manufacturing as the first 214a and second 214b working electrodes can be printed on the substrate 212 in the same layer. As seen in FIG. 5H, the counter 216 and reference 217 electrodes may also be spatially separated and printed directly on the same side of the substrate (i.e., not stacked), where no dielectric layers are separating the counter 216 and reference 217 electrodes from the substrate 212 surface or each other.

The analyte sensors disclosed herein may include multiple active areas, either on the same or different working electrodes. The analyte sensors disclosed herein may feature active areas of the same type (e.g., two glucose-responsive active areas) upon a single working electrode or upon two or more separate working electrodes. The analyte sensors disclosed herein may feature active areas of different types (e.g., a glucose-responsive active area and a ketones-responsive active area or a lactate-responsive active area) upon a single working electrode or upon two or more separate working electrodes. Single working electrode sensor configurations may employ two-electrode or three-electrode detection motifs, according to various embodiments of the present disclosure and as described further herein. Sensor configurations may suitably incorporate a first analyte-responsive active area (e.g., for monitoring glucose) and a second analyte-responsive active area (e.g., for monitoring ketones) according to various embodiments of the present disclosure. Sensor configurations featuring multiple working electrodes are described thereafter in reference to multiple figures.

Figure 6A:
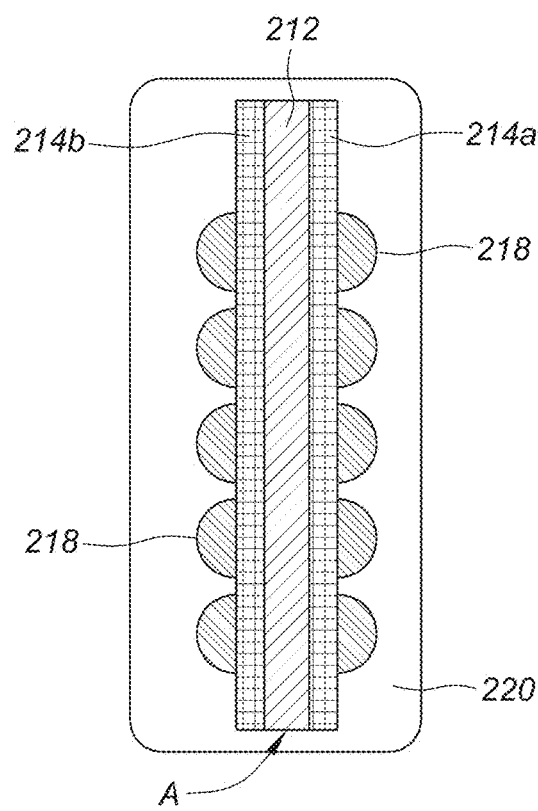
FIG. 6A shows a cross-sectional diagram of an analyte sensor having responsive active areas located on separate working electrodes.

In an alternative embodiment, both working electrodes 214a and 214b may have responsive active areas for the same analyte, e.g., glucose. As seen in FIG. 6A, when multiple working electrodes 214a and 214b are present, responsive active areas specific for a single analyte may be disposed upon both working electrodes 214a and 214b. Membrane 220 may then be dip coated onto the responsive active areas 218

Figure 6B:
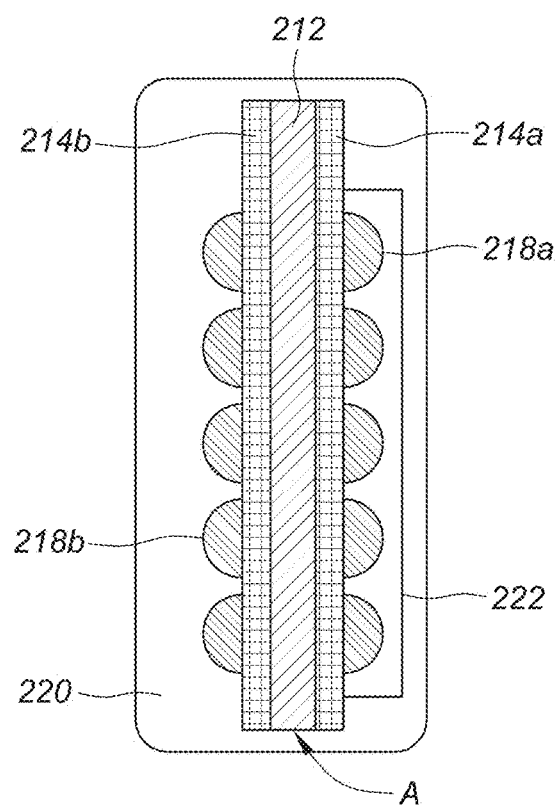
FIG. 6B shows a cross-sectional diagram of an analyte sensor having different responsive active areas and membranes located on separate working electrodes.
Figure 6C:
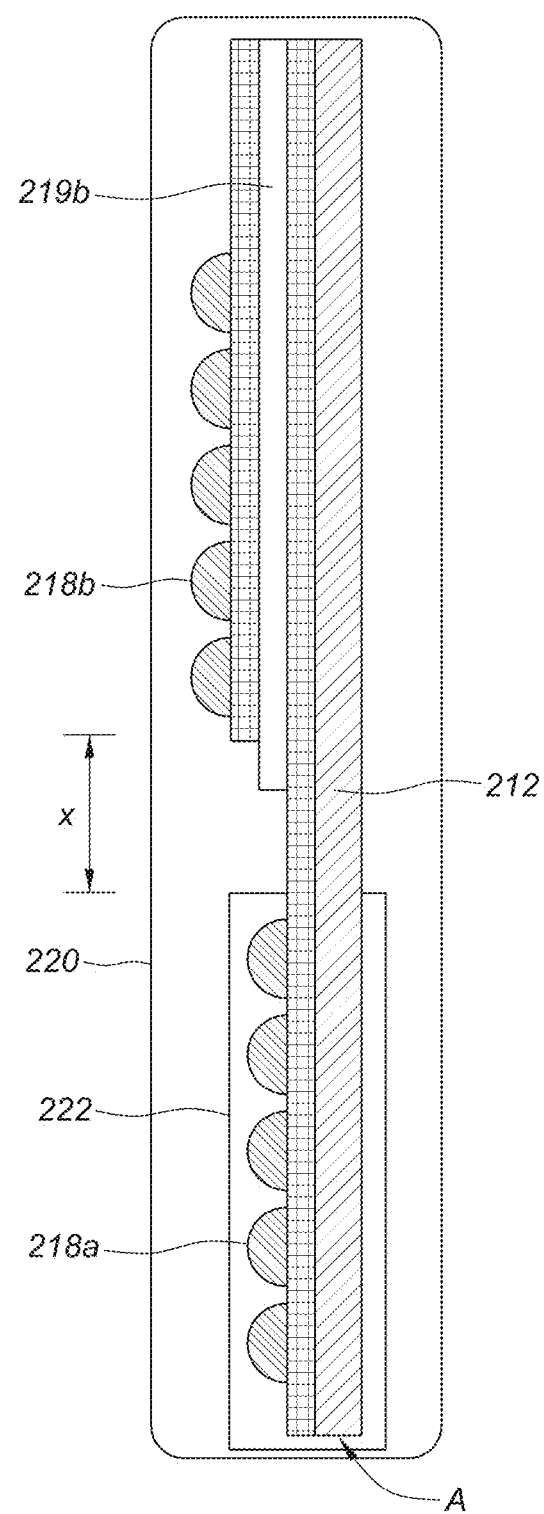
FIG. 6C shows a cross-sectional diagram of an analyte sensor having different responsive active areas and membranes located on separate working electrodes on the same side of a substrate.

In an alternative embodiment, different analytes are being analyzed at the different working electrodes. Although not readily apparent in FIGS. 5 and 6, the composition of membrane 220 may vary at active areas 218a and 218b in order to differentially regulate the analyte flux at each location, as described further herein. For example, membrane 220 may be sprayed and/or printed onto active areas 218a and 218b, such that the composition of membrane 220 differs at each location. Alternatively, when multiple analytes are being analyzed and multiple working electrodes 214a and 214b are present, a responsive active area specific 218a for a first analyte, such as a ketone, may be disposed upon a first working electrode and a responsive active area specific for a second analyte 218b, such as glucose, may be disposed upon a second working electrode.

Sensor configurations employing multiple working electrodes may be particularly advantageous for incorporating both different responsive active areas according to the disclosure herein, since mass transport limiting membranes having differing compositions and/or different permeability values may be deposited more readily during manufacturing when the active areas are separated and/or spaced apart in this manner. Suitable techniques for depositing the mass transport limiting membranes disclosed herein include, for example, spray coating, painting, striping, inkjet printing, stenciling, roller coating, slot die coating, dip coating, or the like, and any combination thereof. For example, with reference to FIG. 6B, membrane 222 may be deposited via stripe coating and membrane 220 may be deposited by dip coating starting from end A of analyte sensor 200. Specifically, membrane 222 may be striped onto active area 218a using a first coating formulation. Alternatively, membrane 222 can be coated on working electrode 214a by, e.g., spray coating or painting. The sensor can then be laser cut for the second membrane 220 dipping that covers the whole sensor tip. After partially curing the first coating formulation upon active area 218a to form membrane 222, end A of analyte sensor 200 may be dipped in a second coating formulation to overcoat both active areas 218a and 218b with the second coating formulation to form membrane 220. As such, membrane 220 may be continuous and feature a bilayer at active area 218a and be homogeneous at active area 218b. For example, with reference to FIG. 6C, where active areas 218a and 218b are located on the same side of the substrate 212 and are separated by a distance x, membranes 220 and 222 may be deposited by dip coating starting from end A of analyte sensor 200. Specifically, end A of analyte sensor 200 may be dipped (one or multiple times) in a first coating formulation to overcoat only active area 218a, and not active area 218b. After partially curing the first coating formulation upon active area 218a to form membrane 222, end A of analyte sensor 200 may be dipped in a second coating formulation to overcoat both active areas 218a and 218b with the second coating formulation to form membrane 220. As such, membrane 220 may be continuous and feature a bilayer at active area 218a and be homogeneous at active area 218b. If membrane 222 is denser than membrane 200, membrane 222 will mainly determine that diffusion properties around responsive active areas 218a. Although active areas 218a and 218b are depicted on the same side of the substrate in FIGS. 5D and 6C, active areas 218a and 218b may also be on opposite sides of substrate 212, where they are separated by a distance x, e.g., measured along an axis parallel to the substrate 212.

Membrane 222 may comprise polyvinylpyridine and a crosslinker, such as polyethylene glycol diglycidyl ether (PEGDGE), e.g., PEGDGE 400. Membrane 220 may comprise polyvinylpyridine-co-styrene and a crosslinker, such as polyethylene glycol diglycidyl ether (PEGDGE), e.g., PEGDGE 400.

Sensor configurations employing multiple working electrodes may be particularly advantageous for incorporating both different responsive active areas according to the disclosure herein, since mass transport limiting membranes having differing compositions and/or different permeability values may be deposited more readily during manufacturing when the active areas are separated and/or spaced apart in this manner. Suitable techniques for depositing the mass transport limiting membranes disclosed herein include, for example, spray coating, painting, inkjet printing, stenciling, roller coating, dip coating, or the like, and any combination thereof.

Figure 7A:
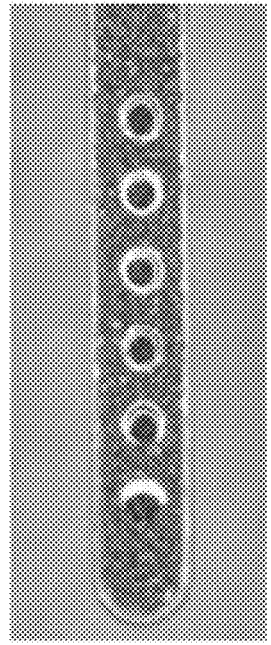
FIGS. 7A-C are pictures of electrodes coated with different membranes.
Figure 7B:
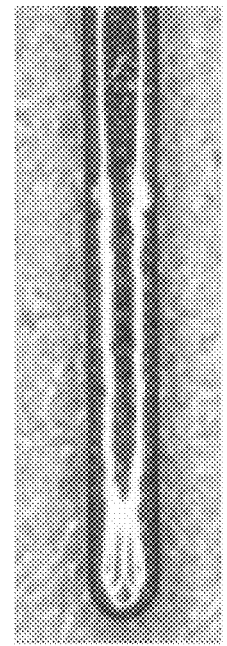
Figure 7C:
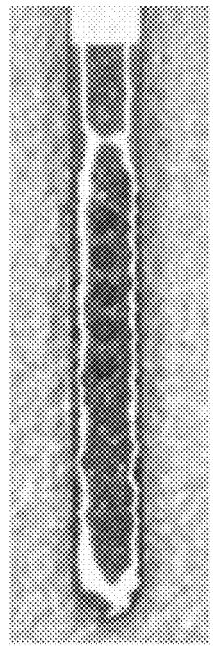
Figure 7D:
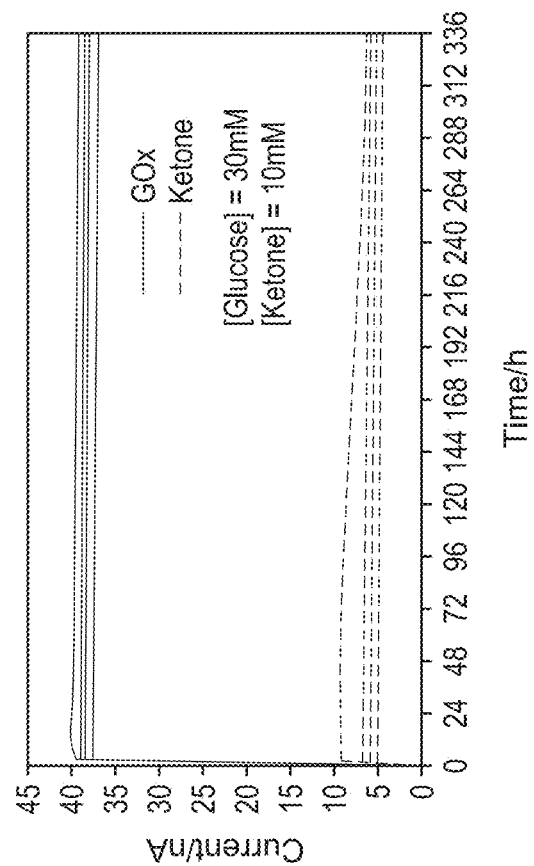
FIG. 7D is an illustrative plot of current response for eight analyte sensors, each containing a glucose-responsive active area and a ketones responsive active area disposed on separate working electrodes following exposure to 30 mM glucose and 10 mM ketones for 2 weeks at 37° C.

FIGS. 7A-7C are photographs of various electrodes coated with different membranes. FIGS. 7A-7C contain responsive active areas specific for ketone and glucose. FIG. 7A shows an electrode with ketone-responsive active areas that has been coated first with a PVP membrane, followed by a polyvinylpyridine-co-styrene membrane. FIG. 7B shows an electrode with glucose responsive active areas that has only been coated with a polyvinylpyridine-co-styrene membrane. The electrodes shown in FIGS. 7A and 7B are the opposite sides of the same sensor tail. FIG. 7C shows an electrode with ketone responsive active areas that was stripe coated with a PVP membrane. FIG. 7C is an example of what the electrode in FIG. 7A looks like after it is coated in PVP but before it is coated in 10Q5. Exemplary membrane compositions for these electrodes can be found in U.S. application Ser. No. 16/774,835 (U.S. Publication No. 2020/0237275), which is herein incorporated by reference in its entirety for all purposes. FIG. 7D is a graph of current response for eight analyte sensors, each containing a glucose-responsive active area and a ketones responsive active area disposed on separate working electrodes on opposite sides of the sensor tail, following exposure to 30 mM glucose and 10 mM ketones for 2 weeks, which shows that the different membrane requirements for the glucose and ketone sensors were achieved with the dual membranes described above. Similarly, exemplary membrane compositions for lactate sensors can be found in U.S. application Ser. No. 16/259,157 (U.S. Publication No. 2019/0320947), which is herein incorporated by reference in its entirety for all purposes. Exemplary membrane compositions for ethanol sensors can be found in U.S. application Ser. No. 16/774,909 (U.S. Publication No. 2020/0237277), which is herein incorporated by reference in its entirety for all purposes. Exemplary membrane compositions for creatinine sensors can be found in U.S. application Ser. No. 16/582,583 (U.S. Publication No. 2020/0241015), which is herein incorporated by reference in its entirety for all purposes. Additional exemplary membrane compositions can be found in U.S. application Ser. No. 16/774,841 (U.S. Publication No. 2020/0237276), which is herein incorporated by reference in its entirety for all purposes.

FIGS. 8A-8D and 9A-9D (see further description in Examples) are calibration graphs form dual glucose/ketone and glucose/lactate sensors, respectively. The calibration graphs show that these dual sensors containing multiple working electrodes with glucose and ketone/lactate responsive areas works as expected.

Example Embodiments of on Body Devices

In vivo monitoring systems can include a sensor that, while positioned in vivo, makes contact with the bodily fluid of the user and senses the analyte levels contained therein. The sensor can be part of an on-body device ("OBD") that resides on the body of the user and contains the electronics and power supply that enable and control the analyte sensing. The on body device, and variations thereof, can also be referred to as a "sensor device," an "on-body electronics device," a "sensor control device," or a "sensor communication device," to name a few. As used herein, these terms are not limited to devices with in vivo analyte sensors, and encompass devices that have ex vivo sensors of other types, whether biometric (e.g., photonic analyte sensors, heart rate sensors, temperature sensors, etc.) or non-biometric. The term "on body" encompasses devices that reside directly on the body (e.g., attached to the skin), are wholly within the body (e.g., a fully implanted device), or are in close proximity to the body, such as a wearable device (e.g., glasses, watch, wristband or bracelet, neckband or necklace, etc.) or a device in a pocket, etc.

In vivo monitoring systems can also include one or more reader devices that read information about a sensed level from the on body device. These reader devices can process and/or display the sensed analyte information, in any number of forms, to the user. These devices, and variations thereof, can be referred to as "handheld reader devices," "readers," "handheld electronics" (or handhelds), "portable data processing" devices or units, "information receivers," "receiver" devices or units (or simply receivers), "relay" devices or units, or "remote" devices or units, to name a few.

In vivo analyte monitoring systems can be differentiated from "in vitro" systems that contact a biological sample outside of the body, and "ex vivo" systems that gain information about the body or a substance within the body but that do so while remaining wholly outside the body without extracting a biological sample from inside the body. In vitro systems can include a meter device that has a port for receiving an analyte test strip carrying a bodily fluid of the user, which can be analyzed to determine the user's analyte level. As mentioned, the embodiments described herein can be used with in vivo systems, ex vivo systems, in vitro systems, and combinations thereof.

Figure 10A:
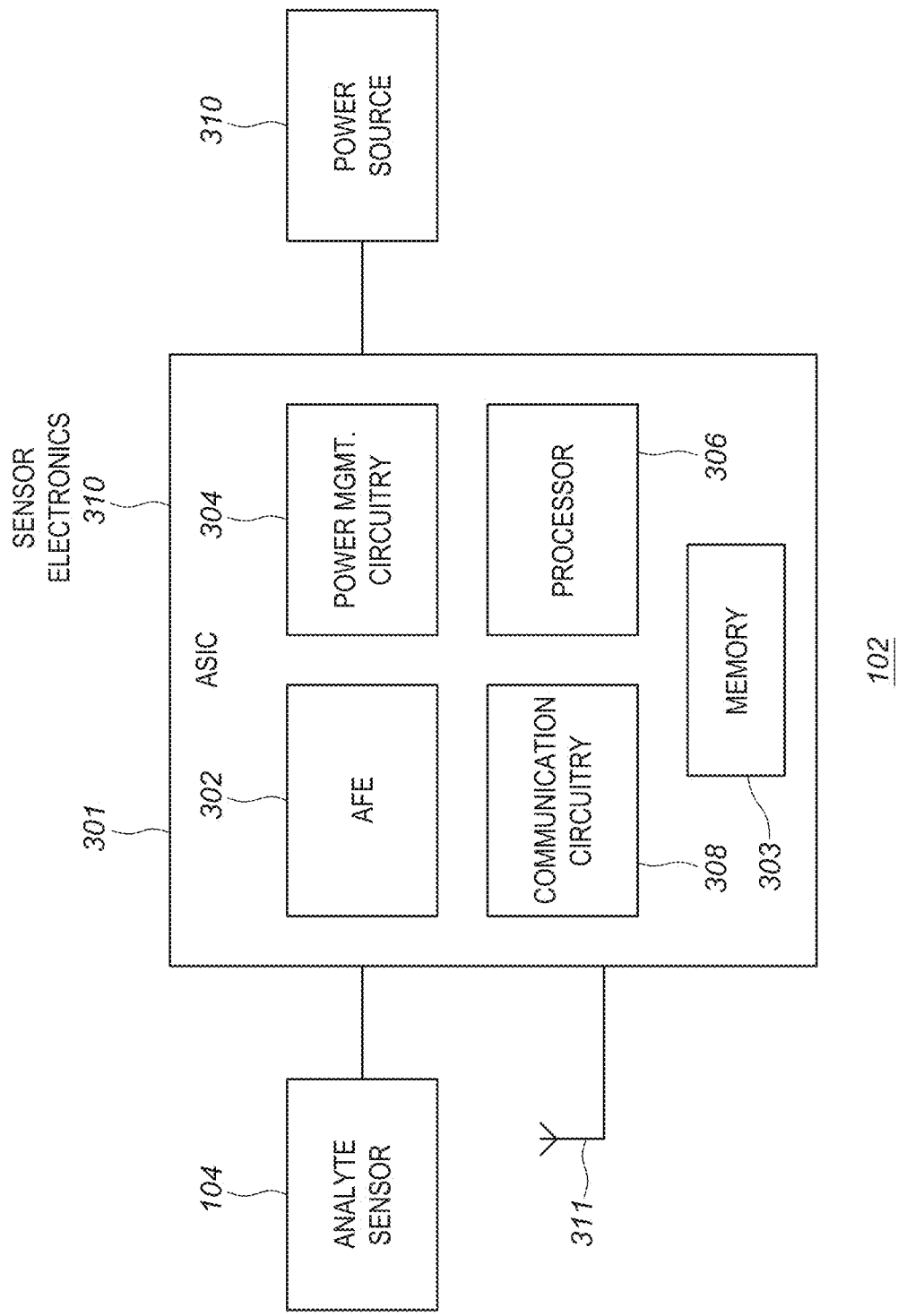
FIGS. 10A-D are block diagrams depicting example embodiments of a sensor control device.

FIGS. 10A-D are block schematic diagrams depicting example embodiments of sensor control device or OBD 102 having analyte sensor 104 and sensor electronics 310 (including analyte monitoring circuitry) that can have the majority of the processing capability for rendering end-result data suitable for display to the user. In FIG. 10A, a single semiconductor chip 301 is depicted that can be a custom application specific integrated circuit (ASIC). Shown within ASIC 301 are certain high-level functional units, including an analog front end (AFE) 302, power management (or control) circuitry 304, processor 306, and communication circuitry 308 (which can be implemented as a transmitter, receiver, transceiver, passive circuit, or otherwise according to the communication protocol). In this embodiment, both AFE 302 and processor 306 are used as analyte monitoring circuitry, but in other embodiments either circuit can perform the analyte monitoring function. Processor 306 can include one or more processors, microprocessors, controllers, and/or microcontrollers, each of which can be a discrete chip or distributed amongst (and a portion of) a number of different chips.

A memory 303 is also included within ASIC 301 and can be shared by the various functional units present within ASIC 301, or can be distributed amongst two or more of them. Memory 303 can also be a separate chip. Memory 303 can be volatile and/or non-volatile memory. In this embodiment, ASIC 301 is coupled with power source 310, which can be a coin cell battery, or the like. AFE 302 interfaces with in vivo analyte sensor 104 and receives measurement data therefrom and outputs the data to processor 306 in digital form, which in turn processes the data to arrive at the end-result glucose discrete and trend values, etc. This data can then be provided to communication circuitry 208 for sending, by way of antenna 311, to reader device 120 (not shown) where minimal further processing is needed by the resident software application to display the data.

Figure 10B:
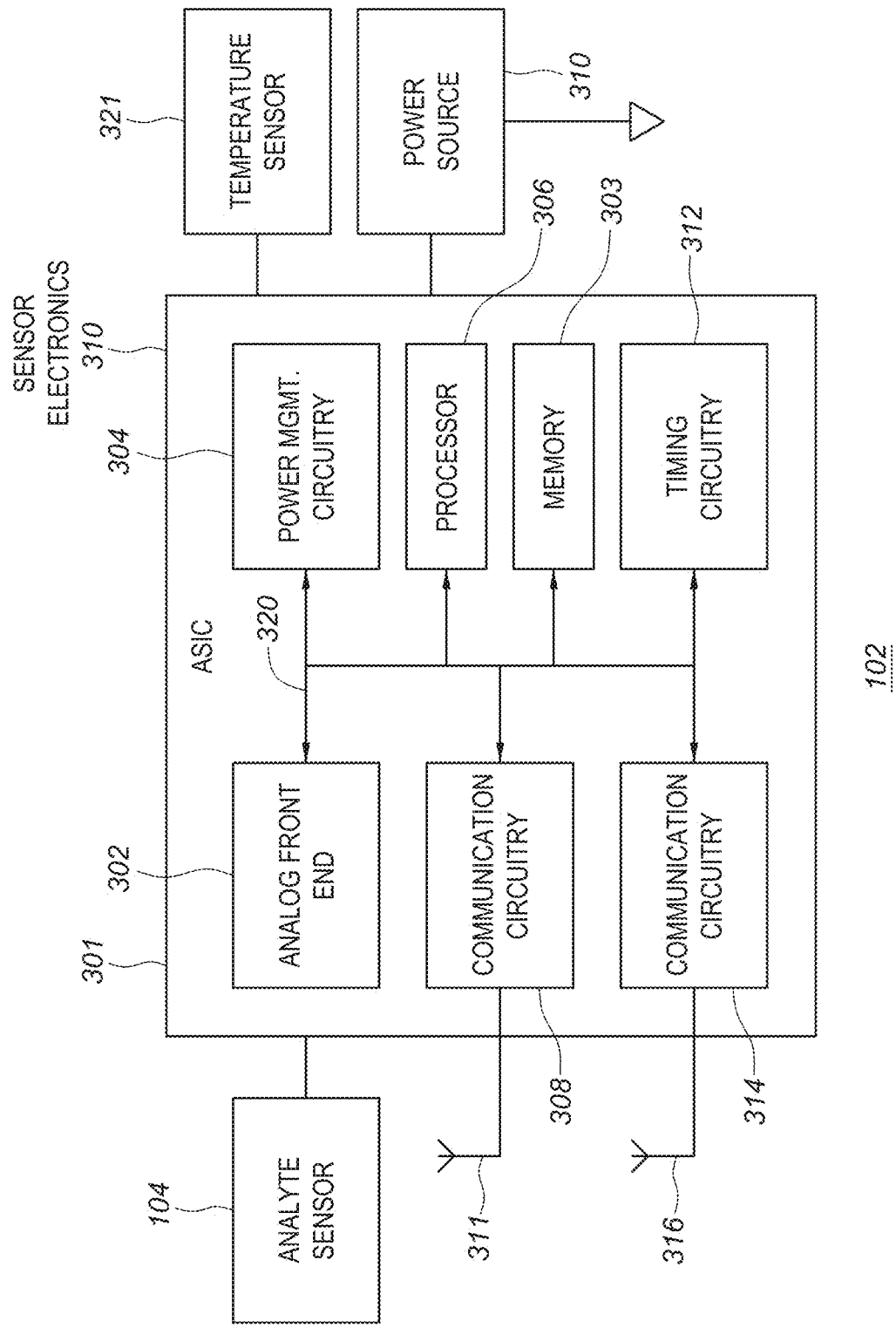

FIG. 10B is a block diagram depicting an alternative example embodiment of a sensor control device or on-body device ("OBD") 102 having analyte sensor 104 and sensor electronics 310 (including analyte monitoring circuitry). Sensor electronics can be implemented in one or more semiconductor chips. In the embodiment of FIG. 10B, sensor electronics 310 are in a single semiconductor chip 301 that can be a custom application specific integrated circuit (ASIC). Shown within ASIC 301 are certain high-level functional units, including an analog front end (AFE) 302, power management (or control) circuitry 304, processor or processing circuitry 306, memory 303, timing circuitry 312, first communication circuitry 302 and second communication circuitry 314. In this embodiment, both AFE 302 and processor 306 are used as analyte monitoring circuitry, but in other embodiments either circuit (or others) can perform the analyte monitoring function.

OBD 102 can be implemented in a highly interconnected fashion, where power supply 312 is coupled with each component shown in FIG. 10B and where those components that communicate or receive data, information, or commands (e.g., AFE 302, power management circuitry 304, processor 306, memory 303, timing circuitry 312, first communication circuitry 308, and second communication circuitry 314), can be communicatively coupled with every other such component over, for example, one or more communication connections or buses 320. FIG. 10B is an abbreviated representation of the typical hardware and functionality that resides within a dedicated reader and those of ordinary skill in the art will readily recognize that other hardware and functionality (e.g., codecs, drivers, glue logic) can also be included.

Figure 10C:
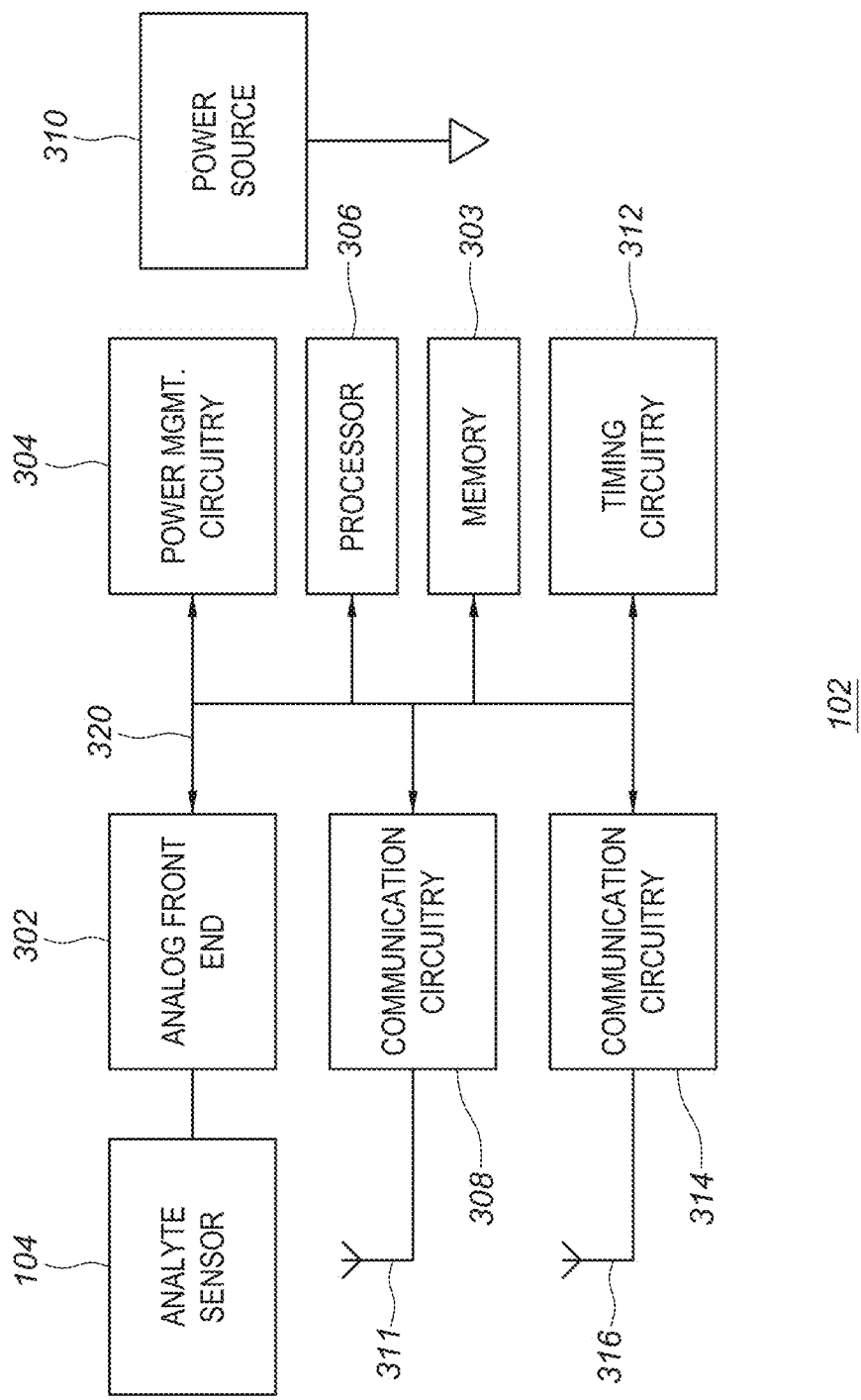

FIG. 10C is a block diagram depicting an alternative example embodiment of OBD 102 having analyte sensor 104 and sensor electronics (including analyte monitoring circuitry). The sensor electronics can be implemented in one or more semiconductor chips, such as application specific integrated circuits (ASICs), off-the-shelf (OTS) chips, programmable devices (e.g., a PGA or FPGA, etc.), or others. OBD 102 includes certain high-level functional units, including an analog front end (AFE) 302, power management (or control) circuitry 304, processor or processing circuitry 306, memory 303, first communication circuitry 308, and second communication circuitry 314. In this embodiment, both AFE 302 and processor 306 are used as analyte monitoring circuitry, but in other embodiments either circuit (or others) can perform the analyte monitoring function.

OBD 102 can be implemented in a highly interconnected fashion, where power supply 310 is coupled with each component shown in FIG. 10C and where those components that communicate or receive data, information, or commands (e.g., AFE 302, power management circuitry 304, processor 306, memory 303, first communication circuitry 308, and second communication circuitry 314), can be communicatively coupled with every other such component over, for example, one or more communication connections or buses 320. FIG. 10C is an abbreviated representation of the typical hardware and functionality that resides within an OBD 102 and those of ordinary skill in the art will readily recognize that other hardware and functionality (e.g., codecs, drivers, glue logic, crystal oscillator, phase-locked loop (PLL)) can also be included.

Figure 10D:
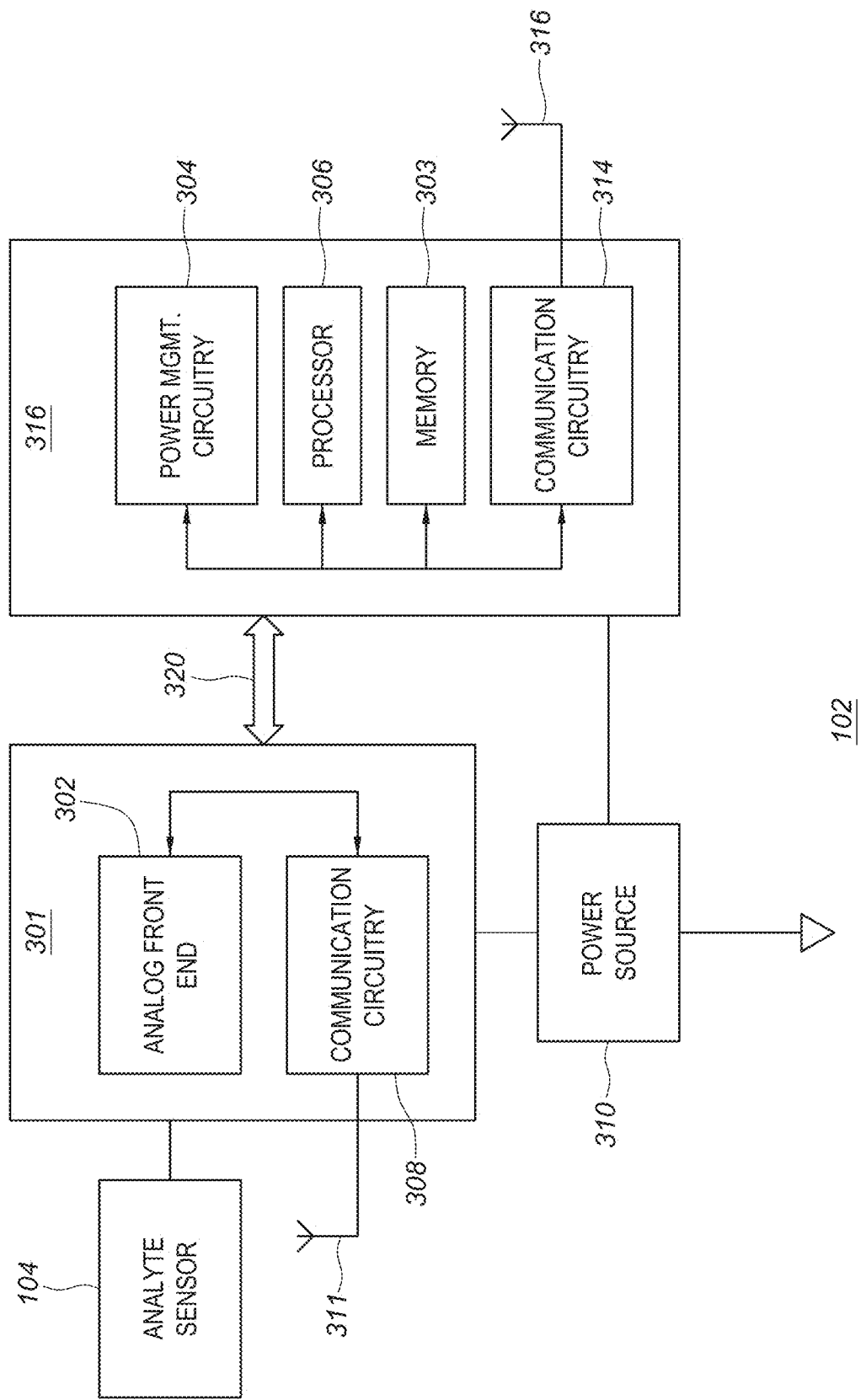

FIG. 10D is a block diagram depicting another example embodiment of OBD 102. Here, OBD 102 includes two semiconductor chips 301 and 361. Chip 301 is an ASIC including AFE 302 and communication circuitry 308 for an NFC link. Chip 361 is a chip including processor 306, memory 303, communication circuitry 314 for a BT link, and power management circuitry 304. A communication interface can be configured in any manner desired. In one embodiment chip 361 is a Bluetooth or BLE radio chip and the communication interface is a serial interface, such as a serial peripheral interface (SPI).

Communications received by OBD 102 over an NFC link can include a command for OBD 102 to take some action, such as to connect a power source to the internal circuitry of one or both chips 301 and/or 361, to activate sensor 104, to read out data stored in memory 303 (e.g., measured analyte data, data identifying OBD 102 (e.g., software version, serial number, etc.)), to perform a diagnostic, to set up a Bluetooth pairing, or others. The command can be specified in the applicable NFC standard, or can be a custom command that requires a custom response. The received communication often requires transmission of a response back to reader 120.

In the embodiment of FIG. 10D, some NFC communications received by communication circuitry 308 can be processed and responded to directly by ASIC 301, without interaction of chip 361. Some commands, however, may require a response generated by a more robust entity such as processor 306. In those instances, ASIC 301 can transfer the relevant portion of the received communication to chip 361 for generation of a response. Chip 361 can then generate the response and, once it is available, output the response back to ASIC 301 for transmission from OBD 102 over the NFC link.

Certain timing constraints can be present for communications transmitted over the NFC link. To comply with the ISO15693 standard, for example, a majority of the NFC commands, including the Read Multiple Block command, Reade Single Block command, custom commands and proprietary commands, must be responded to within a set time limit. In one example ISO 15693 specifies the command be responded to by the tag within 323 microseconds (us) from the time that the tag has received the command. Scenarios may exist where chip 361 takes longer than the set time limit to generate a response. This processing delay can result in violation of the set time limit, and noncompliance with the NFC standard. This may present particular problems when reader 120 is a commercial smart phone, as the smart phone may treat this violation as an error or failure preventing communication from being completed.

Example embodiments disclosed here can compensate for this processing delay and maintain compliance by transmitting one or more responses including a predetermined payload, referred to herein as dummy data. Reader 120 can be programmed or configured to recognize responses where the payload contains byte values (e.g., ABCD, FFFF) matching this predetermined payload as dummy data, and subsequently ignore those responses (e.g., not store in memory) and continue monitoring NFC link 141 for a response transmission including payload data other than the dummy data.

For all the above-described embodiments, communication circuitry 308 and 314 can be coupled to antennas 311 and 316, respectively, which can be on chip or off chip. First communication circuitry 308 and antenna 311 are configured for communication (transmission and/or reception) over a communication link, and second communication circuitry 314 and antenna 316 are configured for communication over a different communication link. In some embodiments, antenna 311 and antenna 316 can be a single shared antenna (e.g., capable of transmission and reception over NFC and UHF frequencies). Communication circuitry 308 and 314 can be implemented as one or more components (e.g., transmitter, receiver, transceiver, passive circuit, encoder, decoder, and/or other communication circuitry) that perform the functions for communications over the respective communications links. Communication circuitry 308 and 314 can receive timing information from timing circuitry 312. Timing circuitry 312 can include a crystal oscillator, phase-locked loop (PLL), and/or other circuitry for generating a stable frequency for timing purposes.

Although not limited to such, in some embodiments, communication circuitry 308 is passive and only uses power harvested from a transmission received from a second device (e.g., reader 120) to generate and propagate a response transmission back to the second device (such as when the communication link is an NFC link). In these and other embodiments, communication circuitry 314 can be active and can use power from OBD power source 312 to generate and propagate a transmission to a second device. The active communication circuitry 314 permits OBD 102 to generate a transmission spontaneously and with prompting from another device (e.g., without first receiving a request, polling signal, timing signal, and the like from the second device).

Processor 306 can include one or more processors, microprocessors, controllers, and/or microcontrollers, each of which can be a discrete chip or distributed amongst (and a portion of) a number of different chips. Processor 306 can interface with communication circuitry 308 and 314 and perform analog-to-digital conversions, encoding and decoding, digital signal processing and other functions that facilitate the conversion of data signals into a format (e.g., in-phase and quadrature) suitable for provision to communication circuitry 308 and 314, which can then transmit the signals wirelessly. Processor 306 can also interface with communication circuitry 308 and 314 to perform the reverse functions necessary to receive a wireless transmission and convert it into digital data or information.

Processor 306 can execute software instructions stored in memory 308. These instructions can cause processor 306 to cause communication circuitry 308 and 314 to transmit a communication generated by processor 306, can cause processor 306 to read and act on received transmissions, to adjust the timing of timing circuitry 312, to collect temperature information from a temperature sensor, to record and/or process a measurement from analyte sensor 314, to monitor collected analyte data for actual or potential alarm conditions, to generate and cause the transmission of an alarm indication using communication circuitry 314, to process data or information received from other devices (e.g., reader 120), to perform tasks to maintain synchronization with reader 120, and others.

Memory 308 is also included within ASIC 301 and can be shared by the various components present within ASIC 301, or can be distributed amongst two or more of them. Memory 308 can also be a separate chip. Memory 308 is non-transitory and can be volatile and/or non-volatile memory. ASIC 301 may be coupled with an optional temperature (or other environmental factor) sensor 321 and power source 310, which can be a coin cell battery, or the like. AFE 302 interfaces with in vivo analyte sensor 104 and receives measurement data therefrom, converts to digital form and outputs to processor 306 which in turn can, in some embodiments, process in any of the manners described elsewhere herein. This data can then be provided to communication circuitry 308 and 314 for sending, by way of antennas 311 and 316, to reader device 120 (not shown), for example, where minimal further processing is needed by the resident software application to display the data. Antennas 311 and 316 can be configured according to the needs of the application and communication protocol. Antennas 311 and 316 can have the same or different configuration and can be, for example, a printed circuit board (PCB) trace antenna, a ceramic antenna, or a discrete metallic antenna. Antennas 311 and 316 can be configured as a monopole antenna, a dipole antenna, an F-type antenna, a loop antenna, and others.

Multiple Sensors in a Single Housing

Figure 11:
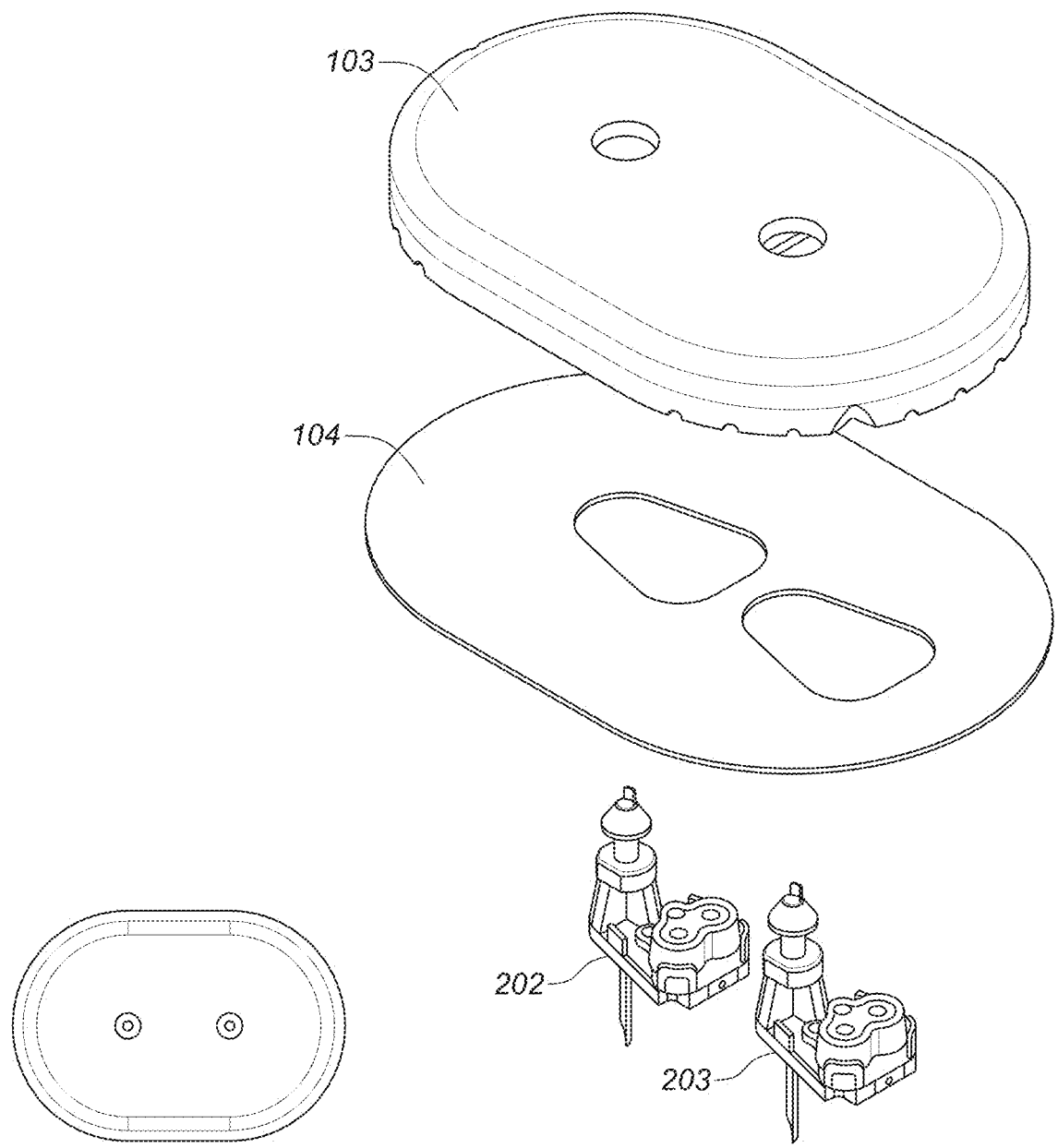
FIG. 11 shows an exploded view of a sensor housing containing two sensors.
Figure 12:
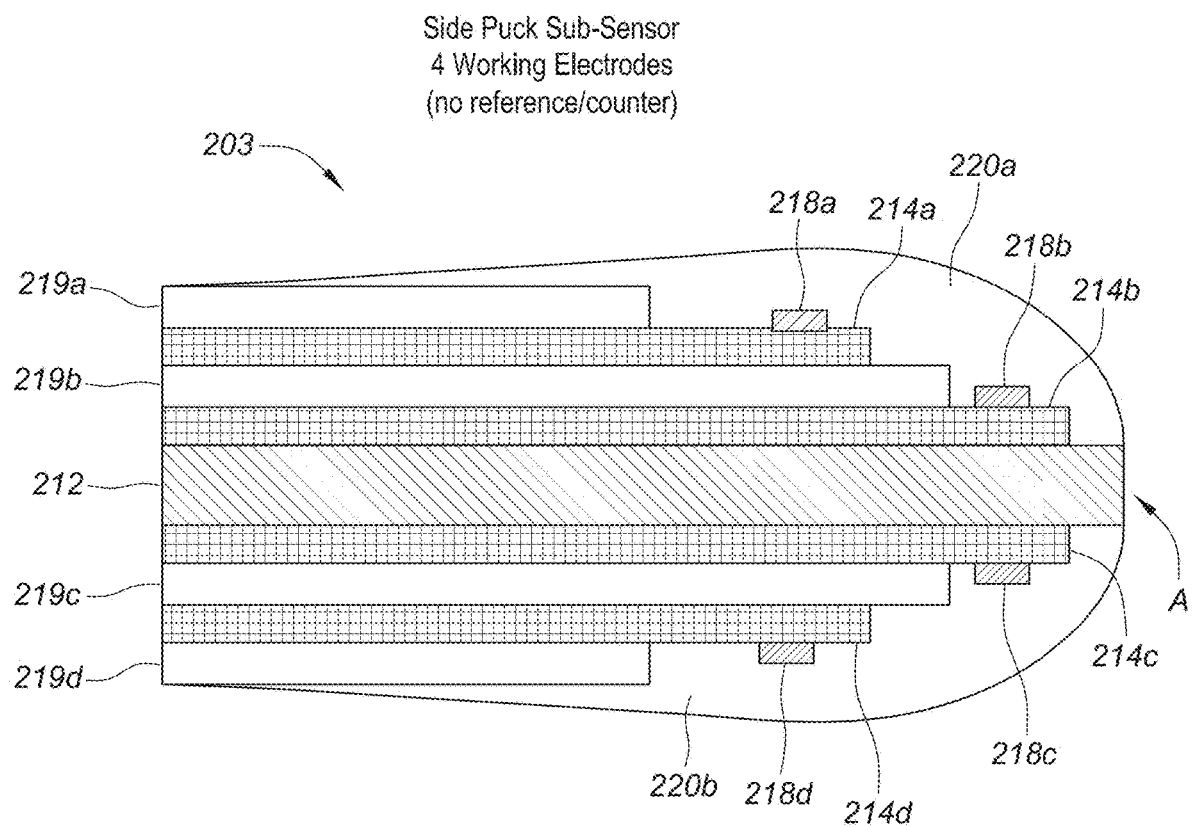
FIG. 12 shows a cross-sectional diagram of an illustrative analyte sensor configuration having four working electrodes.

In an alternative embodiment, additional analytes could be monitored by adding a second sensor, or sub-sensor, containing one or more working electrodes, and no reference or counter electrodes. As seen in FIG. 11, placing sub-sensor 203 in close proximity with primary sensor 202 that contains reference and counter electrodes, such as depicted in FIGS. 3-5, enables sub-sensor 203 to share the counter and reference electrodes in the primary sensor. As seen in FIG. 12, sub-sensor 203 contains four working electrodes 214a, 214b, 214c. and 214d, two on each side of substrate 212. Working electrodes on the same side of substrate 212 are separated with a dielectric material 219b and 219c interposed in between them. Outer dielectric layers 219a and 219d are positioned on working electrodes 214a and 214d. Analyte-specific responsive active area 218a-218d, e.g., a glucose-responsive, creatine-response, or lactate-responsive active area), may be disposed as at least one layer upon at least a portion of working electrodes 214a-214d. The analyte-responsive active area(s) may comprise multiple spots/area or a single spot/area configured for detection of the analyte, as discussed further herein. Both primary sensor 202 and sub-sensor 203 are contained in the same sensor housing 103, which is attached to the skin of a patient with adhesive layer 104. Additional sub-sensors, e.g., 2, 3, 4 or more, can be added into the same sensor housing unit in order to increase the number of analytes being monitored.

With reference to the multiple sensor embodiments described in a single housing, as depicted in FIG. 11, the OBD 102 could include any of the sensor electronics described in FIGS. 10A-10D. Housing 103 contains an AFE 302 that receives analyte data from the working electrodes in the primary sensor and the working electrodes in the sub-sensor. The AFE uses the shared counter and reference electrodes in the primary sensor to output one or more signals related to analyte levels detected by each of the working electrodes in the primary sensor and sub-sensor.

Multiple Sensors in Multiple Housings

Figure 13A:
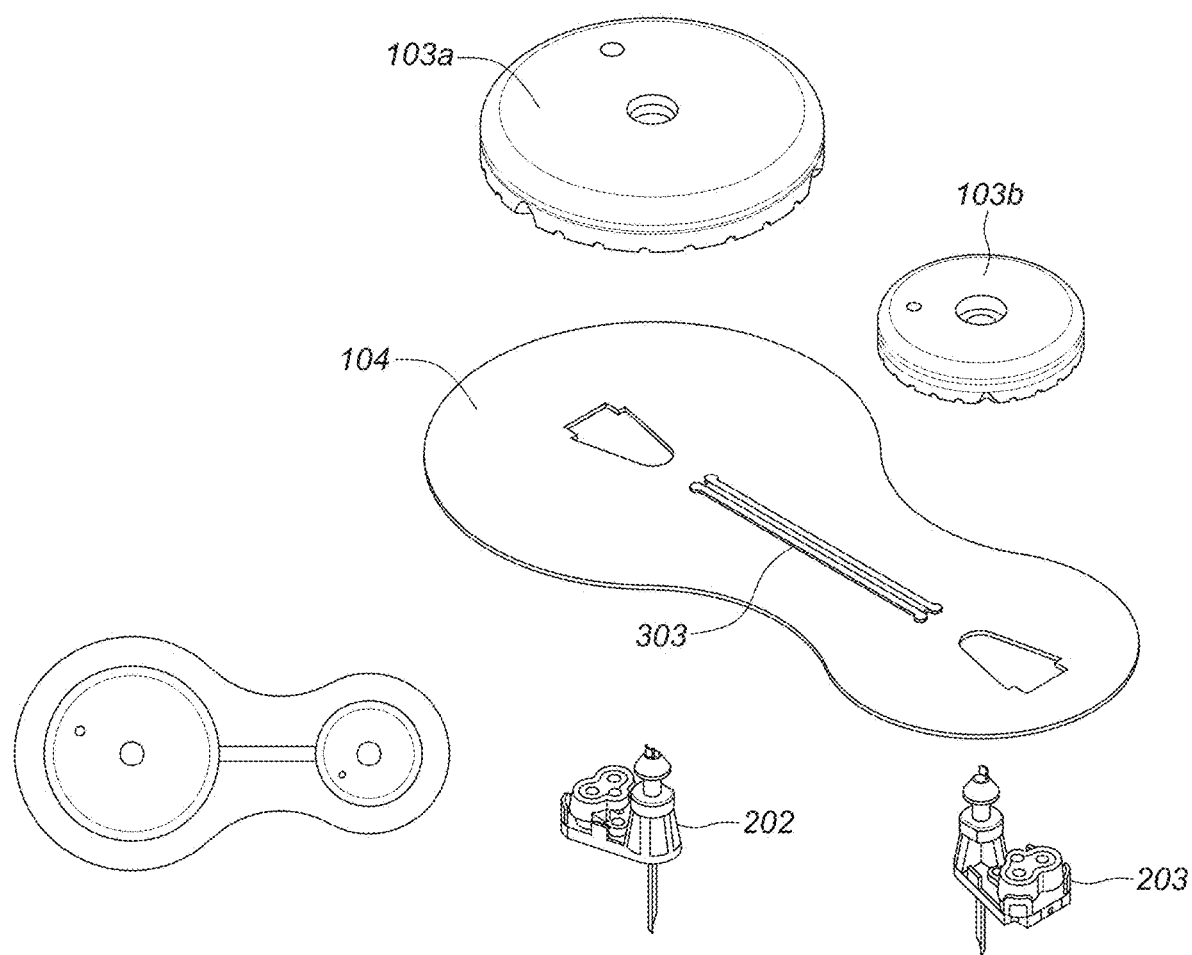
FIG. 13A shows an exploded view of an on-body unit having two sensor housings connected by a printed circuit trace.
Figure 13B:
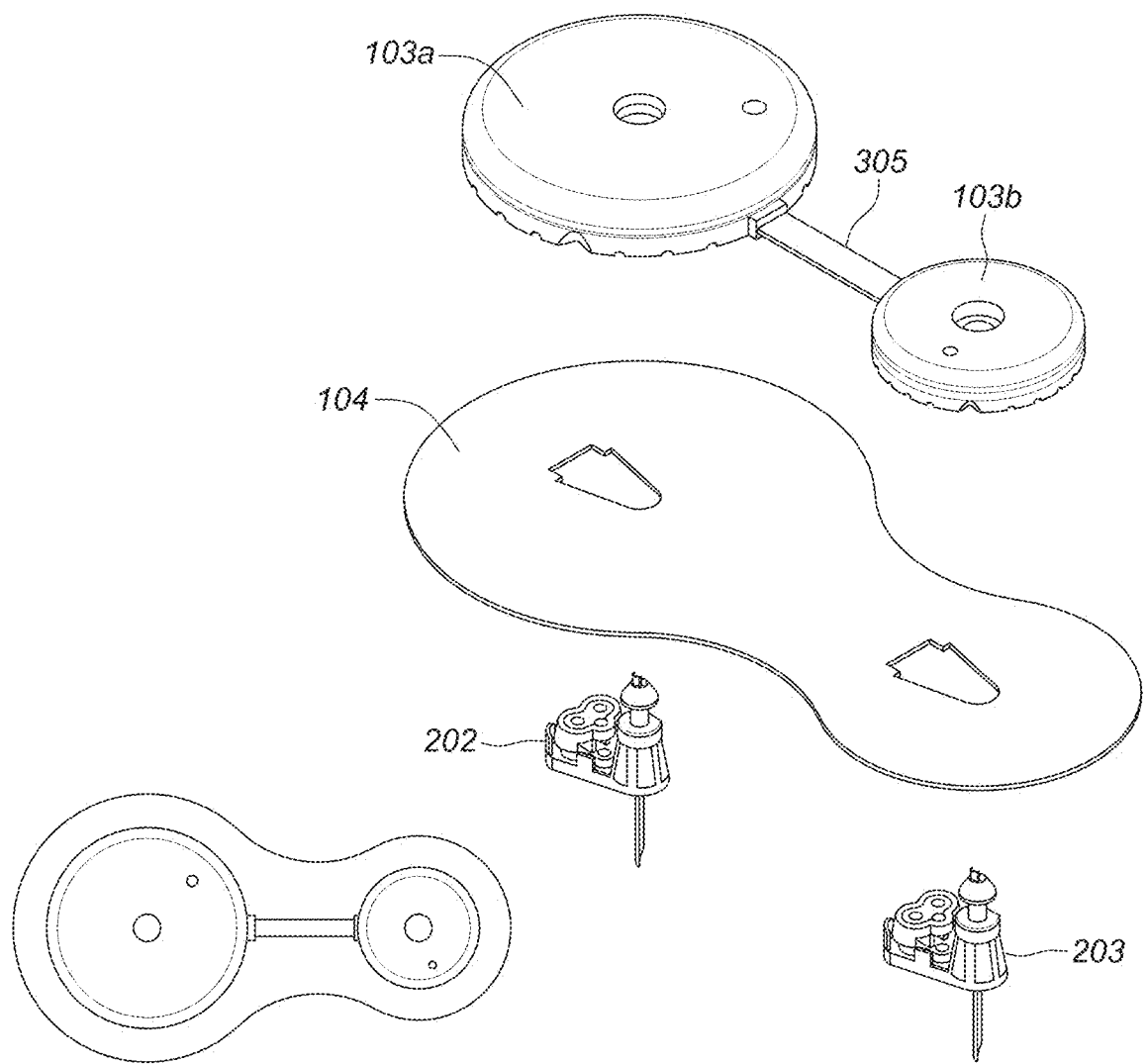
FIG. 13B shows an exploded view of an on-body unit having two sensor housings connected by a flex circuit connection.

In an alternative embodiment, additional analytes could be monitored by adding sub-sensors located in additional sensor housings that are connected or coupled to the sensor housing containing the primary sensor. Similar to the embodiment described above with reference to FIG. 11, as seen in FIGS. 13A-13B, placing sub-sensor 203 in close proximity with primary sensor 202 that contains reference and counter electrodes, such as depicted in FIGS. 3-5, enables sub-sensor 203 to share the counter and reference electrodes in the primary sensor. As seen in FIG. 12, sub-sensor 203 contains four working electrodes 214a, 214b, 214c. and 214d, two on each side of substrate 212. Working electrodes on the same side of substrate 212 are separated with a dielectric material 219b and 219c interposed in between them. Outer dielectric layers 219a and 219d are positioned on working electrodes 214a and 214d. Analyte-specific responsive active area 218a-218d, e.g., a glucose-responsive, creatine-response, or lactate-responsive active area), may be disposed as at least one layer upon at least a portion of working electrodes 214a-214d. The analyte-responsive active area(s) may comprise multiple spots/area or a single spot/area configured for detection of the analyte, as discussed further herein. In the alternative embodiment depicted in FIG. 13A, primary sensor 202 is contained in primary sensor housing 103a and sub-sensor 203 is contained in a different sensor housing 103b, both of which are attached to the skin of a patient with adhesive layer 104. Similar to FIG. 11, sensor housing 103b is in close proximity to primary sensor housing 103a, such that sub-sensor 203 is connected to AFE 302 located in primary sensor housing 103a, thereby enabling sub-sensor 203 to share the counter and reference electrodes in the primary sensor. Thus, sub-sensor housing 103b may not contain any electronics. Alternatively, AFE 302 may be located in sub-sensor housing 103b. As seen in FIG. 13A, conductive traces 303 may be printed on the back of adhesive layer 104 to connect sub-sensor 203 to AFE 302 located in the primary sensor housing 103a. Both sensor housings 103a and 103b may have connector pins (not shown) on the bottom of the housing to press onto the printed conductive trace terminal pads 303 when the sensor housings are laminated on the back of the skin adhesive patch 104. The printed conductive traces 303 should be flexible to accommodate the skin movement. The connection (conductive traces) 303 between the primary sensor housing 103a and sub-sensor housing 103b should also be well insulated and sealed from any moisture, including the contacts, to avoid any moisture leakage that can interfere the sensor signal. Additional sub-sensors, e.g., 2, 3, 4 or more, can be added into additional individual sensor housing units that are in close proximity to primary sensor housing 103a in order to increase the number of analytes being monitored.

In an alternative embodiment, as seen in FIG. 13B, sub-sensor 203 can be coupled to AFE 302 in primary sensor housing 103a through a flex circuit connection 305. The connection (conductive traces) 303 between the primary sensor housing 103a and sub-sensor housing 103b should be well insulated and sealed from any moisture, including the contacts, to avoid any moisture leakage that can interfere the sensor signal. Additional sub-sensors, e.g., 2, 3, 4 or more, can be added into additional individual sensor housing units, and additional sub-sensors can be coupled to AFE 302 located in primary sensor housing 103a in order to increase the number of analytes being monitored.

Figure 13C:
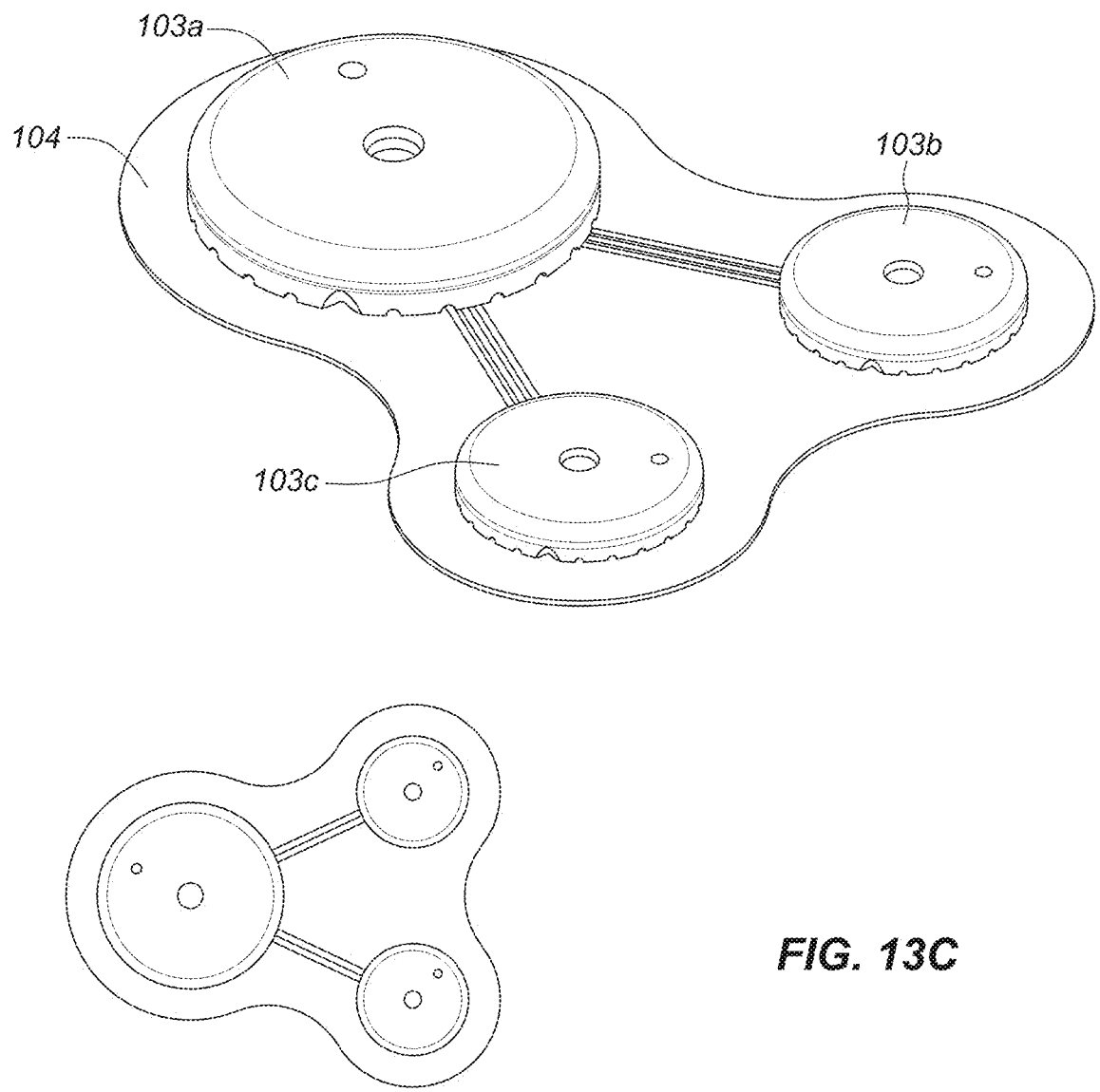
FIG. 13C shows a perspective view of an on-body unit having three connected sensor housings.

As seen in FIG. 13C, additional sub-sensor housings 103b and 103c, each containing a sub-sensor, which is coupled to AFE 302 in primary sensor housing 103a. The sub-sensor and AFE located in primary sensor housing 103a may be coupled or connected via a printed circuit trace, small flex circuit, or another system known in the industry. If the primary sensor contains two working electrodes, e.g., sensor 202, and sub-sensors contained in 103b and 103c each contain a sensor with four working electrodes, then ten analytes could be monitored. Similarly, if there is only a primary sensor housing connected as described above connected to a single sub-sensor housing as described above, then six analytes could be monitored.

In an alternative embodiment, AFE 302 is located in a sub-sensor housing 103b, 103c. In this alternative embodiment, the electrodes (working, counter, reference) in primary sensor 202 can be connected or coupled to AFE 302 as described above for the sub-sensor (e.g., through a via a printed circuit trace, small flex circuit, or another system known in the industry) such that AFE 302 uses the shared counter and reference electrodes in the primary sensor to output one or more signals related to analyte levels detected by each of the working electrodes in the primary sensor and sub-sensor.

Responsive Active Areas

Different detection chemistries must be immobilized on the different responsive active areas that are specific for the various analytes. The enzymes involved in detecting the analytes may be covalently bonded to a polymer at or near the responsive areas. Suitable polymers include, but are not limited to, polyvinylpyridine. The covalently bound polymer may aid in immobilizing the enzyme in a desired position with respect to a responsive active area.

The analyte-responsive active areas each contain an electron transfer agent in any of the illustrative sensor configurations disclosed herein. When a first analyte-responsive active area and a second analyte-responsive active area are both present on the same sensor and/or on the same working electrode, the electron transfer agents may be the same or different depending upon the particular sensor configuration employed. Suitable electron transfer agents may facilitate conveyance of electrons to the working electrode after an enzymatic oxidation or reduction reaction takes place, thereby generating a current that is indicative of the presence of a particular analyte and proportional to the quantity of analyte present. For example, when the first analyte-responsive active area and the second analyte-responsive active area are disposed upon the same working electrode, the electron transfer agent within each active area may be different (e.g., chemically different such that the electron transfer agents exhibit different oxidation-reduction potentials). When multiple working electrodes are present, the electron transfer agent within each active area may be the same or different, since each working electrode may be interrogated separately when obtaining a signal. The electron-transfer agent may be covalently bonded to a polymer in any of the active areas disclosed herein.

According to various embodiments of the present disclosure, suitable electron transfer agents may include electroreducible and electrooxidizable ions, complexes or molecules (e.g., quinones) having oxidation-reduction potentials that are a few hundred millivolts above or below the oxidation-reduction potential of the standard calomel electrode (SCE). According to some embodiments, suitable electron transfer agents may include low-potential osmium complexes, such as those described in U.S. Pat. Nos. 6,134,461 and 6,605,200, which are incorporated herein by reference in their entirety. Additional examples of suitable electron transfer agents include those described in U.S. Pat. Nos. 6,736,957, 7,501,053 and 7,754,093, the disclosures of each of which are incorporated herein by reference in their entirety. Other suitable electron transfer agents may comprise metal compounds or complexes of ruthenium, osmium, iron (e.g., polyvinylferrocene or hexacyanoferrate), or cobalt, including metallocene compounds thereof, for example. Suitable ligands for the metal complexes may also include, for example, bidentate or higher denticity ligands such as, for example, bipyridine, biimidazole, phenanthroline, or pyridyl (imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere.

Active areas suitable for detecting multiple analytes may also comprise a polymer to which the electron transfer agents are covalently bonded. Any of the electron transfer agents disclosed herein may comprise suitable functionality to promote covalent bonding to the polymer within the active areas. Suitable examples of polymer-bound electron transfer agents may include those described in U.S. Pat. Nos. 8,444,834, 8,268,143 and 6,605,201, the disclosures of which are incorporated herein by reference in their entirety. Suitable polymers for inclusion in the active areas may include, but are not limited to, polyvinylpyridines (e.g., poly(4-vinylpyridine)), polyvinylimidazoles (e.g., poly(1-vinylimidazole)), or any copolymer thereof. Illustrative copolymers that may be suitable for inclusion in the active areas include those containing monomer units such as styrene, acrylamide, methacrylamide, or acrylonitrile, for example. The polymer within each active area may be the same or different.

The manner of covalent bonding between the electron transfer agent and the polymer in each active area is not considered to be particularly limited. Covalent bonding of the electron transfer agent to the polymer may take place by polymerizing a monomer unit bearing a covalently bonded electron transfer agent, or the electron transfer agent may be reacted with the polymer separately after the polymer has already been synthesized. According to some embodiments, a bifunctional spacer may covalently bond the electron transfer agent to the polymer within the active area, with a first functional group being reactive with the polymer (e.g., a functional group capable of quaternizing a pyridine nitrogen atom or an imidazole nitrogen atom) and a second functional group being reactive with the electron transfer agent (e.g., a functional group that is reactive with a ligand coordinating a metal ion).

Similarly, one or more of the enzymes within the active areas may be covalently bonded to the polymer. When an enzyme system comprising multiple enzymes is present in a given active area, all of the multiple enzymes may be covalently bonded to the polymer in some embodiments, and in other embodiments, only a portion of the multiple enzymes may be covalently bonded to the polymer. For example, one or more enzymes comprising an enzyme system may be covalently bonded to the polymer and at least one enzyme may be non-covalently associated with the polymer, such that the non-covalently bonded enzyme is physically entrained within the polymer. According to more specific embodiments, covalent bonding of the enzyme(s) to the polymer in a given active area may take place via a crosslinker introduced with a suitable crosslinking agent. Suitable crosslinking agents for reaction with free amino groups in the enzyme (e.g., with the free side chain amine in lysine) may include crosslinking agents such as, for example, polyethylene glycol diglycidyl ether (PEGDGE) or other polyepoxides, cyanuric chloride, N-hydroxysuccinimide, imidoesters, epichlorohydrin, or derivatized variants thereof. Suitable crosslinking agents for reaction with free carboxylic acid groups in the enzyme may include, for example, carbodiimides. The crosslinking of the enzyme to the polymer is generally intermolecular, but can be intramolecular in some embodiments. In particular embodiments, all of the enzymes herein may be covalently bonded to a polymer.

The electron transfer agent and/or the enzyme(s) may be associated with the polymer in the active area through means other than covalent bonding as well. In some embodiments, the electron transfer agent and/or the enzyme(s) may be ionically or coordinatively associated with the polymer. For example, a charged polymer may be ionically associated with an oppositely charged electron transfer agent or enzyme(s). In still other embodiments, the electron transfer agent and/or the enzyme(s) may be physically entrained within the polymer without being bonded thereto. Physically entrained electron transfer agents and/or enzyme(s) may still suitably interact with a fluid to promote analyte detection without being substantially leached from the active areas.

Creatinine

The creatinine-responsive active area may comprise an enzyme system comprising multiple enzymes that are capable of acting in concert to facilitate detection of creatinine, as described below in reference to FIGS. 2A and 2B of U.S. application Ser. No. 16/582,583 (U.S. Publication No. 2020/0241015), which was previously incorporated by reference in its entirety for all purposes. Creatinine may react reversibly and hydrolytically in the presence of creatinine amidohydrolase (CNH) to form creatine. Creatine, in turn, may undergo catalytic hydrolysis in the presence of creatine amidohydrolase (CRH) to form sarcosine. The sarcosine produced via hydrolysis of creatine may undergo oxidation in the presence of the oxidized form of sarcosine oxidase (SOX-ox) to form glycine and formaldehyde, thereby generating the reduced form of sarcosine oxidase (SOX-red) in the process. Hydrogen peroxide also may be generated in the presence of oxygen The reduced form of sarcosine oxidase, in turn, may then undergo re-oxidation in the presence of the oxidized form of an electron transfer agent (e.g., Os(III)), thereby producing the corresponding reduced form of the electron transfer agent (e.g., Os(II)) and delivering a flow of electrons to the working electrode.

Ethanol

The ethanol-responsive active area may comprise an enzyme system comprising multiple enzymes that are capable of acting in concert to facilitate detection of ethanol, as described below in reference to FIGS. 5A-5B of U.S. application Ser. No. 16/774,909, which was previously incorporated by reference in its entirety for all purposes. For example, a concerted enzymatic reaction of alcohol oxidase and xanthine oxidase can be used to detect ethanol. Xanthine oxidase may be covalently bonded to a polymer in the active area of the analyte sensor, and alcohol oxidase is non-covalently associated with the polymer in the active area. In addition to xanthine oxidase, an osmium complex or other transition metal complex capable of exchanging electrons with this enzyme is also covalently bonded to the polymer. Ethanol reacts with oxidized (active) alcohol oxidase in the presence of a flavin co-factor (FAD-already bonded with the alcohol oxidase), thereby forming reduced alcohol oxidase, acetaldehyde, and hydrogen peroxide. The reduced alcohol oxidase may be re-oxidized with molecular oxygen as shown to return the alcohol oxidase to its catalytically active oxidized form. The acetaldehyde enzymatically formed from ethanol then undergoes a subsequent reaction with the oxidized form of xanthine oxidase in the presence of the flavin co-factor that is present natively with the enzyme. Acetic acid is formed in this process and the xanthine oxidase is transformed into a reduced state. The reduced xanthine oxidase may then react with the transition metal electron transfer agent associated with the polymer to transfer electrons to the working electrode, thereby producing a current and regenerating the oxidized form of xanthine oxidase. Hydrogen peroxide may be separately cleared from the sensor environment by catalase that is present in the active area. The amount of enzymatically formed acetaldehyde is proportional to the amount of ethanol originally present. As such, the current produced at the working electrode during the xanthine oxidase oxidation of the acetaldehyde may be proportional to the amount of acetaldehyde present, and, by extension, the amount of ethanol. Correlation of the working electrode current to the ethanol concentration may take place by referring to a lookup table of currents at known ethanol concentrations or by utilizing a calibration curve.

Ketones

The ketones-responsive active area may comprise an enzyme system comprising multiple enzymes that are capable of acting in concert to facilitate detection of ketones, as described below in reference to FIGS. 2A-2C of U.S. application Ser. No. 16/774,835 (U.S. Publication No. 2020/0237275), which was previously incorporated by reference in its entirety for all purposes. For example, β-hydroxybutyrate dehydrogenase (HBDH) and diaphorase, which may be deposited within a ketones-responsive active area upon the surface of at least one working electrode, as described further herein. When a ketones-responsive active area contains this pair of concerted enzymes, β-hydroxybutyrate dehydrogenase may convert β-hydroxybutyrate and oxidized nicotinamide adenine dinucleotide ($NAD^+$) into acetoacetate and reduced nicotinamide adenine dinucleotide (NADH), respectively. The enzyme cofactors $NAD^+$ and NADH aid in promoting the concerted enzymatic reactions disclosed herein. The NADH may then undergo reduction under diaphorase mediation, with the electrons transferred during this process providing the basis for ketone detection at the working electrode. Thus, there is a 1:1 molar correspondence between the amount of electrons transferred to the working electrode and the amount of β-hydroxybutyrate converted, thereby providing the basis for ketones detection and quantification based upon the measured amount of current at the working electrode. Transfer of the electrons resulting from NADH reduction to the working electrode may take place through an electron transfer agent, such as an osmium (Os) compound, as described further below. Albumin may be present as a stabilizer with this pair of concerted enzymes. According to particular embodiments, the β-hydroxybutyrate dehydrogenase and the diaphorase may be covalently bonded to a polymer within the ketones-responsive active area of the analyte sensors. The $NAD^+$ may or may not be covalently bonded to the polymer, but if the $NAD^+$ is not covalently bonded, it may be physically retained within the ketones-responsive active area. A membrane overcoating the ketones-responsive active area may aid in retaining the $NAD^+$ within the ketones-responsive active area while still permitting sufficient inward diffusion of ketones to permit detection thereof. Suitable membrane polymers for overcoating the ketones-responsive active area are discussed further herein.

In an alternative system, β-hydroxybutyrate dehydrogenase (HBDH) may again convert β-hydroxybutyrate and $NAD^+$ into acetoacetate and NADH, respectively. Instead of electron transfer to the working electrode being completed by diaphorase and a transition metal electron transfer agent, the reduced form of NADH oxidase (NADHOx (Red)) undergoes a reaction to form the corresponding oxidized form (NADHOx (Ox)). NADHOx (Red) may then reform through a reaction with molecular oxygen to produce superoxide, which may undergo subsequent conversion to hydrogen peroxide under superoxide dismutase (SOD) mediation. The hydrogen peroxide may then undergo reduction at the working electrode to provide a signal that may be correlated to the amount of ketones that were initially present. The SOD may be covalently bonded to a polymer in the ketones-responsive active area, according to various embodiments. Like the enzyme system described previously, the β-hydroxybutyrate dehydrogenase and the NADH oxidase may be covalently bonded to a polymer in the ketones-responsive active area, and the NAD may or may not be covalently bonded to a polymer in the ketones-responsive active area. If the $NAD^+$ is not covalently bonded, it may be physically retained within the ketones-responsive active area, with a membrane polymer promoting retention of the $NAD^+$ within the ketones-responsive active area.

Another enzymatic detection chemistry for ketones may utilize β-hydroxybutyrate dehydrogenase (HBDH) to convert β-hydroxybutyrate and $NAD^+$ into acetoacetate and NADH, respectively. The electron transfer cycle in this case is completed by oxidation of poly-1,10-phenanthroline-5,6-dione at the working electrode to reform NAD. The poly-1,10-phenanthroline-5,6-dione may or may not be covalently bonded to a polymer within the ketones-responsive active area. Like the enzyme systems described previously, the β-hydroxybutyrate dehydrogenase may be covalently bonded to a polymer in the ketones-responsive active area, and the NAD may or may not be covalently bonded to a polymer in the ketones-responsive active area. Inclusion of an albumin in the active area may provide a surprising improvement in response stability. A suitable membrane polymer may promote retention of the $NAD^+$ within the ketones-responsive active area.

Lactate

The lactate-responsive active area may comprise an enzyme system comprising multiple enzymes that are capable of acting in concert to facilitate detection of lactate, as described below in U.S. application Ser. No. 16/259,157 (U.S. Publication No. 2019/0320947), which was previously incorporated by reference in its entirety for all purposes. Lactate-responsive analyte sensors may replace glucose oxidase with lactate oxidase to facilitate lactate detection. Such lactate-responsive analyte sensors based upon modified glucose-responsive sensor chemistry are described in commonly owned U.S. Pat. No. 9,914,952, which is incorporated herein by reference in its entirety. As described therein, enhancement of the analytical sensitivity toward lactate and some response stabilization may be realized by modifying the glucose-responsive sensor chemistry to include catalase in the active area when lactate oxidase is instead present. Although the incorporation of catalase helps to some degree, it does not completely stabilize the long-term response of the analyte sensor. Instead, the lactate signal in catalase-containing analyte sensors falls up to about 10% over 48 hours of monitoring. Since catalases are known to be reactive toward hydrogen peroxide, the stabilization effect of catalase in lactate-responsive analyte sensors is believed to involve scrubbing of transient hydrogen peroxide that may otherwise impact the activity of the lactate oxidase. Although catalase may improve the performance of lactate-responsive analyte sensors, additional performance improvement may still be needed for such analyte sensors to realize their true potential.

The performance of lactate-responsive analyte sensors may be improved by substituting a different stabilizer for catalase, such as albumin, and by changing the mass transport limiting membrane disposed upon the active area. Several different membrane chemistries or configurations may promote improved analyte sensor performance for lactate analyses, as discussed in U.S. application Ser. No. 16/259,157 (U.S. Publication No. 2019/0320947), which was previously incorporated by reference.

According to the present disclosure, the analytes may be monitored in any biological fluid of interest such as dermal fluid, interstitial fluid, plasma, blood, lymph, synovial fluid, cerebrospinal fluid, saliva, bronchoalveolar lavage, amniotic fluid, or the like. In particular embodiments, analyte sensors of the present disclosure may be adapted for assaying dermal fluid or interstitial fluid to determine concentrations of analytes in vivo.

Responsive active areas for different analytes can be located on the same or different working electrodes of the same sensor. For example, creatinine-responsive analyte sensors may further incorporate a glucose-responsive active area for sensing both creatinine and glucose, in some embodiments of the present disclosure.

When a first analyte-responsive active area and the second analyte-responsive active area are arranged upon a single working electrode, one of the active areas may be configured such that it can be interrogated separately to facilitate detection of each analyte, as described hereinafter. In particular, the first analyte-responsive active area and the second analyte-responsive active area may comprise different electron transfer agents to allow one of the active areas to produce a signal independently of the other. Either of the first analyte-responsive active area or the second analyte-responsive active area may be configured to produce a signal independently of the other active area.

In embodiments wherein the first analyte-responsive active area and the second analyte-responsive active area are arranged upon a single working electrode, the oxidation-reduction potential associated with the second analyte-responsive active area may be separated from the oxidation-reduction potential of the first analyte-responsive active area by at least about 100 mV, or by at least about 150 mV, or by at least about 200 mV. The upper limit of the separation between the oxidation-reduction potentials is dictated by the working electrochemical window in vivo. By having the oxidation-reduction potentials of the two active areas sufficiently separated in magnitude from one another, an electrochemical reaction may take place within one of the two active areas without substantially inducing an electrochemical reaction within the other active area. Thus, a signal from one of the first analyte-responsive active area or the second analyte-responsive active area may be independently produced at or above its corresponding oxidation-reduction potential (the lower oxidation-reduction potential) but below the oxidation-reduction potential of the other of the responsive active areas (the higher oxidation-reduction potential). At or above the oxidation-reduction potential (the higher oxidation-reduction potential) of the other active area that was not previously interrogated, in contrast, electrochemical reactions may occur within both of the responsive active areas. As such, the resulting signal at or above the higher oxidation-reduction potential may include a signal contribution from both the first analyte-responsive active area and the second analyte-responsive active area, and the observed signal is a composite signal. The signal contribution from one active area (either the first analyte-responsive active area or the second analyte-responsive active area) at or above its oxidation-reduction potential may then be determined by subtracting from the composite signal the signal obtained solely from either the first analyte-responsive active area or the second analyte-responsive active area at or above its corresponding oxidation-reduction potential.

In more specific embodiments, the first analyte-responsive active area and the second analyte-responsive active area may contain different electron transfer agents when the active areas are located upon the same working electrode, so as to afford oxidation-reduction potentials that are sufficiently separated in magnitude from one another. More specifically, the first analyte-responsive active area may comprise a first electron transfer agent and the second analyte-responsive active area may comprise a second electron transfer agent, with the first and second electron transfer agents being different. The metal center and/or the ligands present in a given electron transfer agent may be varied to provide sufficient separation of the oxidation-reduction potentials within the two active areas, according to various embodiments of the present disclosure.

Ideally, a first analyte-responsive active area and a second analyte-responsive active area located upon a single working electrode may be configured to attain a steady state current rapidly upon operating the analyte sensor at a given potential. Rapid attainment of a steady state current may be promoted by choosing an electron transfer agent for each active area that changes its oxidation state quickly upon being exposed to a potential at or above its oxidation-reduction potential. Making the active areas as thin as possible may also facilitate rapid attainment of a steady state current. For example, suitable thicknesses for the responsive active areas may range from about 0.1 microns to about 10 microns. In some or other embodiments, combining a conductive material such as, for example, carbon nanotubes, graphene, or metal nanoparticles within one or more of the active areas may promote rapid attainment of a steady state current. Suitable amounts of conductive particles may range from about 0.1% to about 50% by weight of the active area, or from about 1% to about 50% by weight, or from about 0.1% to about 10% by weight, or from about 1% to about 10% by weight. Stabilizers may also be employed to promote response stability.

It is also to be appreciated that the sensitivity (output current) of the analyte sensors toward each analyte may be varied by changing the coverage (area or size) of the active areas, the areal ratio of the active areas with respect to one another, the identity, thickness and/or composition of a mass transport limiting membrane overcoating the active areas. Variation of these parameters may be conducted readily by one having ordinary skill in the art once granted the benefit of the disclosure herein.

Other embodiments of analyte sensors disclosed herein may feature the first analyte-responsive active area and the second analyte-responsive active area upon the surface of different working electrodes. Such analyte sensors may further comprise a second working electrode, a second analyte-responsive active area disposed upon a surface of the second working electrode, and a second membrane that is permeable to the second analyte overcoating the second analyte-responsive active area. The second analyte-responsive active area may comprise a second electron transfer agent, a third polymer, and an enzyme that is covalently bonded to the third polymer. When the first analyte-responsive active area and the second analyte-responsive active area are disposed upon separate working electrodes, the electron transfer agent associated with each active area may be the same or different.

Membranes

Even with suitable detection chemistries in hand, incorporating two different types of active areas upon a single analyte sensor (either on the same working electrode or on different working electrodes) is sometimes not a straightforward matter. Analyte sensors oftentimes employ a membrane overcoating the active area(s) to function as a mass transport limiting membrane and/or to improve biocompatibility. Limiting analyte access to the active area(s) with a mass transport limiting membrane can aid in avoiding sensor overload (saturation), thereby improving detection performance and accuracy. When assaying multiple analytes using a single analyte sensor, different permeability values may be exhibited by the various analytes across a given mass transport limiting membrane, potentially resulting in widely disparate sensitivities for each analyte. Incorporating different mass transport limiting membranes upon each active area may be problematic in some instances. Surprisingly and advantageously, certain analytes, such as glucose and creatinine, may be successfully analyzed using a mass transport limiting membrane that is compositionally the same at each location, thereby simplifying fabrication of analyte sensors having detection capabilities for both analytes.

At least one mass transport limiting membrane may overcoat the first analyte-responsive active area and the optional second analyte-responsive active area, when present, as also described in further detail below. For example, the glucose-responsive active area, when present, may comprise a glucose-responsive enzyme. The mass transport limiting membrane may also overcoat the oxygen scavenger (e.g., glucose oxidase), in which case the oxygen scavenger may be interposed between separate membrane layers.

In vivo analyte sensors may also include a membrane disposed over at least the implanted portion of the analyte sensor. In one aspect, the membrane may improve biocompatibility of the analyte sensor. In another aspect, the membrane may be permeable or semi-permeable to an analyte of interest and limit the overall analyte flux to the active area of the analyte sensor. That is, the membrane may function as a mass transport limiting membrane. Limiting analyte access to the active area of the sensor with a mass transport limiting membrane can aid in avoiding sensor overload (saturation), thereby improving detection performance and accuracy. Such membranes may be highly specific toward limiting mass transport of a particular analyte, with other substances permeating through the membrane at significantly different rates. The differing membrane permeability of various potential analytes represents a significant hurdle for developing analyte sensors configured for assaying multiple analytes. Namely, the differing membrane permeability values may lead to significantly different sensitivities for the multiple analytes, thereby complicating analyses. The differing sensitivities for multiple analytes may sometimes be partially compensated for by using active areas of different sizes (e.g., smaller active areas for analytes having high sensitivity/permeability and larger active areas for analytes having lower sensitivity/permeability), but this approach may present significant manufacturing challenges and may not be applicable in all cases.

In particular embodiments of the present disclosure, the mass transport limiting membrane overcoating the analyte-responsive active area may comprise at least a crosslinked polyvinylpyridine homopolymer or copolymer, including polyvinylpyridine-co-styrene polymers. A mass transport limiting membrane having a similar composition may overcoat an oxygen scavenger, such as glucose oxidase, as well. The composition of the mass transport limiting membrane may be the same or different where the mass transport limiting membrane overcoats each active area. Suitable techniques for depositing a mass transport limiting membrane upon the active area(s) may include, for example, spray coating, painting, inkjet printing, stenciling, roller coating, striping, slot die coating, dip coating, the like, and any combination thereof.

Accordingly, certain analyte sensors of the present disclosure that are capable of detecting multiple analytes may comprise: an implantable sensor tail comprising a first working electrode; a second working electrode, wherein the first and second working electrodes are separated by a substrate; a reference electrode; a counter electrode; a reference material layer; a first analyte-responsive active area disposed upon a surface of the first working electrode; and a second analyte-responsive active area disposed upon a surface of the second working electrode.

Detection methods for assaying multiple analytes may comprise: exposing an analyte sensor to a fluid comprising at least a first analyte and a second analyte, wherein the analyte sensor comprises an implantable sensor tail comprising a first working electrode, a second working electrode, a reference electrode, a counter electrode, a reference material layer, a first analyte-responsive active area disposed upon a surface of the first working electrode, and a second analyte-responsive active area disposed upon a surface of the second working electrode, wherein the first and second working electrodes are separated by a substrate; applying a potential (or different potentials) to the first working electrode and the second working electrode; obtaining a first signal at or above an oxidation-reduction potential of the first analyte-responsive active area, the signal being proportional to a concentration of the first analyte in the fluid; obtaining a second signal at or above an oxidation-reduction potential of the second analyte-responsive active area, the second signal being proportional to a concentration of the second analyte in the fluid; and correlating the first signal to the concentration of the first analyte in the fluid and the second signal to the concentration of the second analyte in the fluid. The signals may be measured at the same or different times.

In an alternative embodiment, the analyte sensor (or sub-sensor) comprises a first working electrode; a second working electrode, wherein second working electrode is electrically isolated from the first working electrode; a first analyte-responsive active area disposed upon a surface of the first working electrode; and a second analyte-responsive active area disposed upon a surface of the second working electrode, Where the sensor tail does not include a counter and/or reference electrode, the sub-sensor may share the counter and/or reference electrodes from another sensor. The sensor may further comprise additional (e.g., third and fourth working electrodes). The third working electrode may further comprise a third analyte-responsive active area comprising a third electron transfer agent, a third polymer, and an enzyme system comprising multiple enzymes that are capable of acting in concert to facilitate detection of the third analyte. The fourth working electrode may further comprise a fourth analyte-responsive active area comprising a fourth electron transfer agent, a fourth polymer, and an enzyme system comprising multiple enzymes that are capable of acting in concert to facilitate detection of the third analyte.

Detection methods for assaying multiple analytes may comprise: exposing an analyte sensor to a fluid comprising at least a first and a second, analyte, wherein the analyte sensor comprises an implantable sensor tail comprising a first working electrode, a second working electrode, a first analyte-responsive active area disposed upon a surface of the first working electrode, and a second analyte-responsive active area disposed upon a surface of the second working electrode, wherein the analyte sensor does not include a counter electrode and a reference electrode; applying a potential to the first working electrode and the second working electrode; obtaining a first signal at or above an oxidation-reduction potential of the first analyte-responsive active area, the signal being proportional to a concentration of the first analyte in the fluid; obtaining a second signal at or above an oxidation-reduction potential of the second analyte-responsive active area, the second signal being proportional to a concentration of the second analyte in the fluid; and correlating the first signal to the concentration of the first analyte in the fluid and the second signal to the concentration of the second analyte in the fluid. If additional working electrodes are present, the method may further comprise applying a potential to the third working electrode and the fourth working electrode; obtaining a third signal at or above an oxidation-reduction potential of the third analyte-responsive active area, the third signal being proportional to a concentration of the third analyte in the fluid; obtaining a fourth signal at or above an oxidation-reduction potential of the fourth analyte-responsive active area, the fourth signal being proportional to a concentration of the fourth analyte in the fluid; and correlating the third signal to the concentration of the third analyte in the fluid and the fourth signal to the concentration of the fourth analyte in the fluid.

In another embodiment, certain on body devices of the present disclosure may comprise: a housing; and a first sensor and a second sensor disposed within the housing, wherein the first sensor comprises an implantable sensor tail comprising a first working electrode, a second working electrode, a shared reference electrode, and a shared counter electrode, and wherein the second sensor comprises an implantable sensor tail comprising first working electrode and a second working electrode, wherein the second sensor does not include a counter electrode and a reference electrode. In some embodiments, the second sensor may include a third working electrode and a fourth working electrode. The third working electrode and a fourth working electrodes may comprise a fifth analyte-responsive active area disposed upon a surface of the third working electrode of the second sensor and a sixth analyte-responsive active area disposed upon a surface of the fourth working electrode of the second sensor.

In another embodiment, certain on body devices of the present disclosure may comprise: a first housing; a first sensor disposed within the first housing, wherein the first sensor comprises an implantable sensor tail comprising a first working electrode, a second working electrode, a reference electrode, and a counter electrode; a second housing; a second sensor disposed within the second housing, wherein the second sensor comprises an implantable sensor tail comprising first working electrode and a second working electrode, wherein the second sensor does not include a counter electrode and a reference electrode. In some embodiments, the second sensor may include a third working electrode and a fourth working electrode. The third working electrode and a fourth working electrodes may comprise a fifth analyte-responsive active area disposed upon a surface of the third working electrode of the second sensor and a sixth analyte-responsive active area disposed upon a surface of the fourth working electrode of the second sensor.

Detection methods for assaying multiple analytes may comprise: exposing an analyte sensor system to a fluid comprising at least a first, second, third, and fourth analyte, wherein the analyte sensor system comprises a first sensor and a second sensor, wherein the first sensor comprises an implantable sensor tail comprising a first working electrode, a second working electrode, a shared reference electrode, and a shared counter electrode, and the second sensor comprises an implantable sensor tail comprising a first working electrode and a second working electrode, wherein the second sensor does not include a counter electrode and a reference electrode, wherein each of the first and second working electrodes of the first sensor comprises first and second analyte-responsive active areas, respectively, and wherein the first and second working electrodes of the second sensor each comprises third and fourth analyte-responsive active areas, respectively; applying a potential to the first and second working electrodes of the first and second sensors; obtaining a first signal at or above an oxidation-reduction potential of the first analyte-responsive active area, the signal being proportional to a concentration of the first analyte in the fluid; obtaining a second signal at or above an oxidation-reduction potential of the second analyte-responsive active area, the second signal being proportional to a concentration of the second analyte in the fluid; obtaining a third signal at or above an oxidation-reduction potential of the third analyte-responsive active area, the third signal being proportional to a concentration of the third analyte in the fluid; obtaining a fourth signal at or above an oxidation-reduction potential of the third analyte-responsive active area, the third signal being proportional to a concentration of the fourth analyte in the fluid; and correlating the first, second, third, and fourth signals to the concentrations of the first, second, third, and fourth analytes in the fluid, respectively. With regard to the potentials applied to the first, second, third, and fourth electrodes, the same potential could be applied to all of the electrodes, alternatively different potentials could be applied to different electrodes, alternatively the same potential could be applied to some of the electrodes and a different potential could be applied to the other electrodes.

In some embodiments, the analytes being detected include, but are not limited to, glucose, β-hydroxybutyrate, uric acid, ketone, creatinine, ethanol, and lactate.

In some embodiments, the analyte sensors may further comprise a first membrane that is permeable to the first analyte and overcoats the first analyte-responsive active area and a second membrane that is permeable to the second analyte and overcoats the second analyte-responsive active area. The membranes may have the same or different compositions. For sensor devices having multiple response active areas, the sensors may include as many different membranes as there are different responsive active areas.

In some embodiments, the reference material layer in the sensor tail may comprise Ag and AgCl. The reference material layer may be disposed on the counter electrode or the reference electrode.

In some embodiments, the first analyte-responsive active area and second analyte-responsive active area each comprise an electron-transfer agent that is covalently bonded to a polymer in each of the first analyte-responsive active area and second analyte-responsive active area. Alternatively, the first analyte-responsive active area further comprises a first electron transfer agent, a first polymer, and an enzyme system comprising multiple enzymes that are capable of acting in concert to facilitate detection of the first analyte and the second analyte-responsive active area further comprises a second electron transfer agent, a second polymer, and an enzyme system comprising multiple enzymes that are capable of acting in concert to facilitate detection of the second analyte.

For the embodiments that include a sub-sensor that does not include counter and reference electrodes on the implantable sensor tail, but rather shares the counter and reference electrodes on another sensor, the sensor system may include analog front end circuitry that receives analyte data from all of the working electrodes of the sub-sensor, in addition to the working electrodes of the sensor that the counter and reference electrodes are disposed on. For instance, where the primary sensor has two working electrodes and counter and reference electrodes and the sub-sensor has four working electrodes (and no counter and reference electrodes), analog front end circuitry may receive analyte data from the first and second working electrodes of the first (primary) sensor and the first, second, third, and fourth working electrodes of the second (sub) sensor. The analog front end circuitry could be located in the housing of the primary sensor or the housing of a sub-sensor.

In some embodiments, the signal may be correlated to a corresponding concentration of an analyte by consulting a lookup table or calibration curve. A lookup table for the analyte may be populated by assaying multiple samples having known analyte concentrations and recording the sensor response at each concentration. Similarly, a calibration curve for the analyte may be determined by plotting the analyte sensor response as a function of the analyte concentration and determining a suitable calibration function over the calibration range (e.g., by regression, particularly linear regression).

A processor may determine which sensor response value in a lookup table is closest to that measured for a sample having an unknown analyte concentration and then report the analyte concentration accordingly. In some or other embodiments, if the sensor response value for a sample having an unknown analyte concentration is between the recorded values in the lookup table, the processor may interpolate between two lookup table values to estimate the analyte concentration. Interpolation may assume a linear concentration variation between the two values reported in the lookup table. Interpolation may be employed when the sensor response differs a sufficient amount from a given value in the lookup table, such as variation of about 10% or greater.

Likewise, according to some or other various embodiments, a processor may input the sensor response value for a sample having an unknown analyte concentration into a corresponding calibration function. The processor may then report the analyte concentration accordingly.

The sensor tail may further comprise additional working electrodes having analyte-responsive active area disposed thereon, and in which the analyte-responsive active area may comprise a second electron transfer agent, a third polymer, and an enzyme that is covalently bonded to the third polymer. As such, the methods may further comprise: applying a potential(s) to the additional working electrodes, obtaining additional signals at or above an oxidation-reduction potential of the respective analyte-responsive active area that is proportional to a concentration of analyte in the fluid, and correlating the additional signals to the concentration of the analytes in the fluid.

In more specific embodiments, the oxidation-reduction potential associated with the first analyte-responsive active area may be separated from the oxidation-reduction potential of the second analyte-responsive active area by at least about 100 mV, or by at least about 150 mV, or by at least about 200 mV in order to provide sufficient separation for independent production of a signal from the first active area. The differing oxidation-reduction potentials may result from incorporating different electron transfer agents in the active areas. Similarly, the oxidation-reduction potentials associated with each of the third, fourth, fifth, sixth, seventh, eighth, ninth, or tenth analyte-responsive active areas may be separated any of the other oxidation-reduction potentials by at least about 100 mV, or by at least about 150 mV, or by at least about 200 mV in order to provide sufficient separation for independent production of a signal from the first active area.

The methods may additionally comprise applying a potential to the first working electrode and a potential to the second working electrode, obtaining a first signal at or above an oxidation-reduction potential of the first analyte-responsive active area, in which the first signal is proportional to a concentration of first analyte in the fluid, obtaining a second signal at or above an oxidation-reduction potential of the glucose-responsive active area, in which the second signal is proportional to a concentration of second analyte in the fluid, and correlating the first signal to the concentration of the first analyte in the fluid and the second signal to the concentration of second analyte in the fluid.

According to more specific embodiments, the signals from the different working electrodes can be measured at different times. For example, where there are two working electrodes, a potential may be alternately applied to the first working electrode and the second working electrode. In other specific embodiments, the first signal and the second signal may be measured simultaneously via a first channel and a second channel, in which case a potential may be applied to both electrodes at the same time. In either case, the signal associated with each active area may then be correlated to the concentration of respective analytes using a lookup table or a calibration function in a similar manner to that discussed above.

Figure 8C:
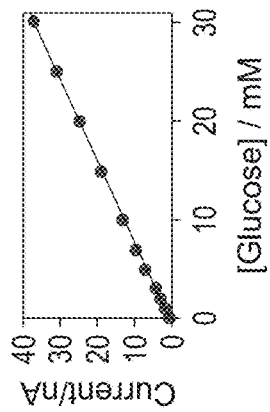
FIG. 8C shows an illustrative plot of average current response versus glucose concentrations.
Figure 8D:
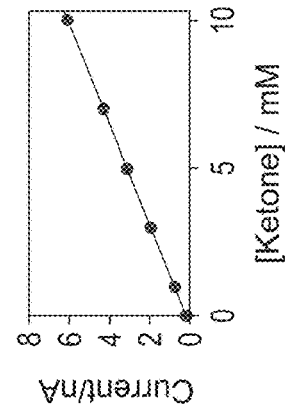
FIG. 8D shows an illustrative plot of average current response versus ketone concentrations.
Figure 8A:
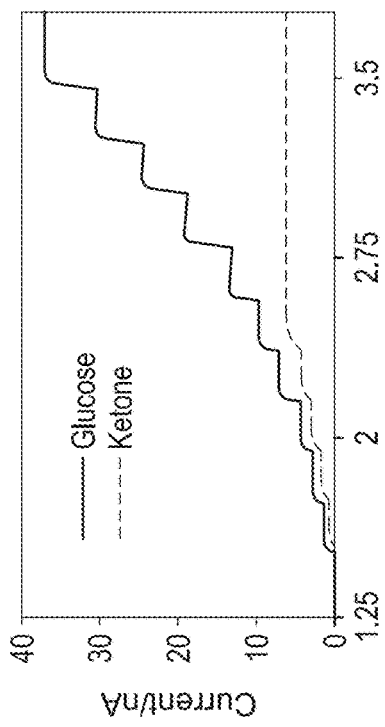
FIG. 8A shows the response for an electrode containing glucose- and ketone-responsive areas when exposed to varying glucose and ketone concentrations.
Figure 8B:
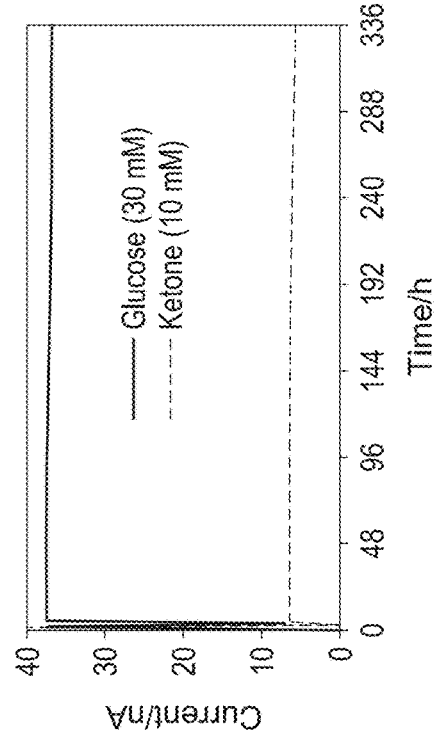
FIG. 8B is an illustrative plot of current response for the electrode of FIGS. 7A and 7B when exposed to 30 mM glucose and 10 mM ketones for 2 weeks at 37° C.
Figure 9C:
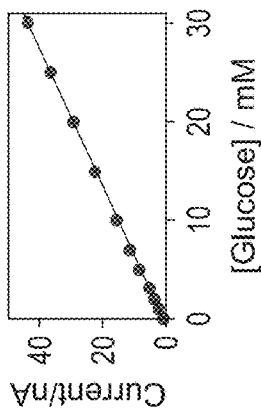
FIG. 9C shows an illustrative plot of average current response versus glucose concentrations.
Figure 9D:
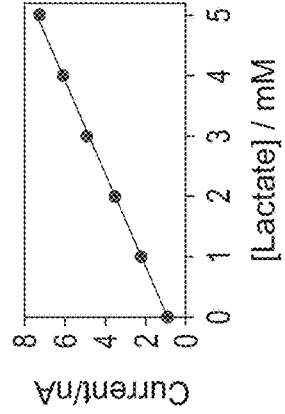
FIG. 9D shows an illustrative plot of average current response versus lactate concentrations.
Figure 9A:
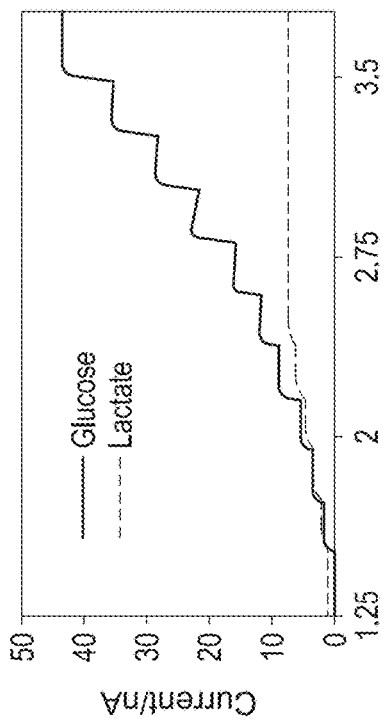
FIG. 9A shows the response for an electrode containing glucose- and lactate-responsive areas when exposed to varying glucose and lactate concentrations.
Figure 9B:
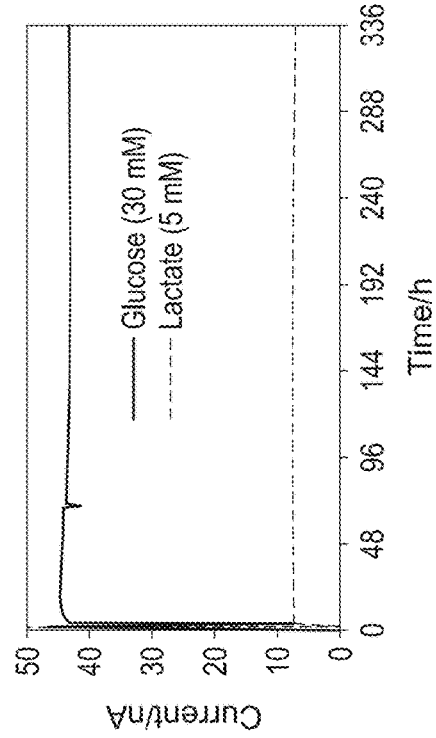
FIG. 9B shows the response for an electrode containing glucose- and lactate-responsive areas when exposed to 30 mM glucose and 5 mM lactate for 2 weeks at 37° C.

FIGS. 8A-D show illustrative plots of an analyte sensor response to varying concentrations of glucose and ketone. As shown in FIGS. 8C and 8D, the analyte sensor afforded a linear response toward both analytes over the tested concentration ranges. As shown in FIG. 8A, the sensor response was rapid for both analytes and remained stable at a given analyte concentration. FIGS. 9A-D show illustrative plots of an analyte sensor response to varying concentrations of glucose and lactate. As shown in FIGS. 9C and 9D, the analyte sensor afforded a linear response toward both analytes over the tested concentration ranges. As shown in FIG. 9A, the sensor response was rapid for both analytes and remained stable at a given analyte concentration. Exemplary compositions of active sites and membranes for glucose, ketone, and lactate can be found in U.S. application Ser. No. 16/774,835 (U.S. Publication No. 2020/0237275) and U.S. application Ser. No. 16/259,157 (U.S. Publication No. 2019/0320947), which were previously incorporated by reference in their entirety for all purposes.

The embodiments described herein are restated and expanded upon in the following paragraphs without explicit reference to the figures.

In many embodiments, an analyte sensor is described. The analyte sensor includes a first working electrode; a second working electrode, wherein the first and second working electrodes are separated by a substrate; a reference electrode; a counter electrode; a reference material layer; a first analyte-responsive active area disposed upon a surface of the first working electrode; and a second analyte-responsive active area disposed upon a surface of the second working electrode.

In some embodiments, the analyte sensor also includes a first membrane that is permeable to the first analyte and overcoats the first analyte-responsive active area; and a second membrane that is permeable to the second analyte and overcoats the second analyte-responsive active area. In some embodiments, the first membrane overcoats the first and second analyte-responsive active areas.

In some embodiments, the first analyte-responsive active area and the second analyte-responsive active area each comprise an electron-transfer agent that is covalently bonded to a polymer in each of the first analyte-responsive active area and second analyte-responsive active area.

In some embodiments, the first analyte-responsive active area further comprises a first electron transfer agent, a first polymer, and an enzyme system comprising multiple enzymes that are capable of acting in concert to facilitate detection of the first analyte.

In some embodiments, the second analyte-responsive active area further comprises a second electron transfer agent, a second polymer, and an enzyme system comprising multiple enzymes that are capable of acting in concert to facilitate detection of the second analyte.

In some embodiments, the reference material layer comprises Ag and AgCl.

In some embodiments, the reference material layer is disposed on the counter electrode or reference electrode.

In some embodiments, the first analyte is selected from the group consisting of glucose, β-hydroxybutyrate, uric acid, ketone, creatinine, ethanol, and lactate.

In some embodiments, the second analyte is selected from the group consisting of glucose, β-hydroxybutyrate, uric acid, ketone, creatinine, ethanol, and lactate.

In some embodiments, the implantable sensor tail is configured for insertion into a tissue.

In some embodiments, the first membrane and the second membrane have different compositions.

In some embodiments, the first membrane and the second membrane have the same compositions.

In some embodiments, the first working electrode is separated from the counter electrode or reference electrode by a dielectric layer.

In some embodiments, the second working electrode is separated from the counter electrode or reference electrode by a dielectric layer.

In some embodiments, the analyte sensor further includes first and second dielectric layers disposed on the reference electrode and the counter electrode.

In many embodiments, a method is described. The method includes the steps of exposing an analyte sensor to a fluid comprising at least a first analyte and a second analyte, wherein the analyte sensor comprises an implantable sensor tail comprising a first working electrode, a second working electrode, a reference electrode, a counter electrode, a reference material layer, a first analyte-responsive active area disposed upon a surface of the first working electrode, and a second analyte-responsive active area disposed upon a surface of the second working electrode, wherein the first and second working electrodes are separated by a substrate; applying a potential to the first working electrode and the second working electrode; obtaining a first signal at or above an oxidation-reduction potential of the first analyte-responsive active area, the signal being proportional to a concentration of the first analyte in the fluid; obtaining a second signal at or above an oxidation-reduction potential of the second analyte-responsive active area, the second signal being proportional to a concentration of the second analyte in the fluid; and correlating the first signal to the concentration of the first analyte in the fluid and the second signal to the concentration of the second analyte in the fluid.

In some embodiments, the implantable sensor tail further comprises a first membrane that is permeable to the first analyte and overcoats the first analyte-responsive active area and a second membrane that is permeable to the second analyte and overcoats the second analyte-responsive active area.

In some embodiments, the first analyte-responsive active area and second analyte-responsive active area each comprise an electron-transfer agent that is covalently bonded to a polymer in each of the first analyte-responsive active area and second analyte-responsive active area.

In some embodiments, the first analyte-responsive active area further comprises a first electron transfer agent, a first polymer, and an enzyme system comprising multiple enzymes that are capable of acting in concert to facilitate detection of the first analyte.

In some embodiments, the second analyte-responsive active area further comprises a second electron transfer agent, a second polymer, and an enzyme system comprising multiple enzymes that are capable of acting in concert to facilitate detection of the second analyte.

In some embodiments, the reference material layer comprises Ag and AgCl.

In some embodiments, the reference material layer is disposed on the counter electrode or reference electrode.

In some embodiments, the first analyte is selected from the group consisting of glucose, β-hydroxybutyrate, uric acid, ketone, creatinine, ethanol, and lactate.

In some embodiments, the second analyte is selected from the group consisting of glucose, β-hydroxybutyrate, uric acid, ketone, creatinine, ethanol, and lactate.

In some embodiments, the implantable sensor tail is configured for insertion into a tissue. In some embodiments, the first membrane and the second membrane have different compositions. In some embodiments, the first membrane and the second membrane have the same compositions.

In some embodiments, the first working electrode is separated from the counter electrode or reference electrode by a dielectric layer.

In some embodiments, the second working electrode is separated from the counter electrode or reference electrode by a dielectric layer.

In some embodiments, the analyte sensor further includes first and second dielectric layers disposed on the reference electrode and the counter electrode.

In some embodiments, the fluid is a biological fluid and the analyte sensor is exposed to the biological fluid in vivo.

In some embodiments, the first signal and the second signal are measured at different times.

In some embodiments, the first signal and the second signal are measured at the same time.

In some embodiments, the first signal and the second signal are obtained simultaneously via a first channel and a second channel.

In many embodiments, an analyte sensor is described. The analyte sensor includes an implantable sensor tail comprising: a first working electrode; a second working electrode, wherein second working electrode is electrically isolated from the first working electrode; a first analyte-responsive active area disposed upon a surface of the first working electrode; and a second analyte-responsive active area disposed upon a surface of the second working electrode.

In some embodiments, the analyte sensor further includes a first membrane that is permeable to the first analyte and overcoats the first analyte-responsive active area.

In some embodiments, the analyte sensor further includes a second membrane that is permeable to the second analyte and overcoats the second analyte-responsive active area.

In some embodiments, the first working electrode and the second working electrode are separated by a substrate.

In some embodiments, the first working electrode and the second working electrode are separated by a dielectric layer.

In some embodiments, a third working electrode and a third analyte-responsive active area disposed upon a surface of the third working electrode.

In some embodiments, the analyte sensor further includes a third working electrode and a third analyte-responsive active area disposed upon a surface of the third working electrode. In some embodiments, the analyte sensor further includes a fourth working electrode and a fourth analyte-responsive active area disposed upon a surface of the fourth working electrode.

In some embodiments, the first analyte-responsive active area and second analyte-responsive active area each comprise an electron-transfer agent that is covalently bonded to a polymer in each of the first analyte-responsive active area and second analyte-responsive active area, respectively.

In some embodiments, the analyte sensor further includes a first analyte-responsive active area comprising a first electron transfer agent, a first polymer, and an enzyme system comprising multiple enzymes that are capable of acting in concert to facilitate detection of the first analyte.

In some embodiments, the analyte sensor further includes a second analyte-responsive active area comprising a second electron transfer agent, a second polymer, and an enzyme system comprising multiple enzymes that are capable of acting in concert to facilitate detection of the second analyte.

In some embodiments, the first analyte is selected from the group consisting of glucose, β-hydroxybutyrate, uric acid, ketone, creatinine, ethanol, and lactate.

In some embodiments, the second analyte is selected from the group consisting of glucose, β-hydroxybutyrate, uric acid, ketone, creatinine, ethanol, and lactate.

In some embodiments, the implantable sensor tail is configured for insertion into a tissue.

In some embodiments, the analyte sensor does not include a counter or reference electrode.

In some embodiments, the analyte sensor is configured to be electrically coupled to an additional analyte sensor comprising a counter electrode and a reference electrode.

In many embodiments, a method is described. The method includes the steps of exposing an analyte sensor system to a fluid comprising at least a first and a second analyte, wherein the analyte sensor system comprises first and second analyte sensors, wherein the first analyte sensor comprises an implantable sensor tail comprising a reference electrode and a counter electrode, and wherein the second analyte sensor comprises an implantable sensor tail comprising a first working electrode, a second working electrode, a first analyte-responsive active area disposed upon a surface of the first working electrode, and a second analyte-responsive active area disposed upon a surface of the second working electrode, wherein the second analyte sensor does not include a counter electrode and a reference electrode; applying a potential to the first and second analyte sensors; obtaining a first signal at or above an oxidation-reduction potential of the first analyte-responsive active area, the first signal being proportional to a concentration of the first analyte in the fluid; obtaining a second signal at or above an oxidation-reduction potential of the second analyte-responsive active area, the second signal being proportional to a concentration of the second analyte in the fluid; and correlating the first signal to the concentration of the first analyte in the fluid and the second signal to the concentration of the second analyte in the fluid.

In some embodiments, the first analyte sensor further comprises at least one working electrode and an analyte-responsive area disposed upon a surface of the at least one working electrode.

In some embodiments, the first analyte-responsive active area and second analyte-responsive active area each comprise an electron-transfer agent that is covalently bonded to a polymer in each of the first analyte-responsive active area and second analyte-responsive active area.

In some embodiments, the second analyte sensor further includes a first analyte-responsive active area comprising a first electron transfer agent, a first polymer, and an enzyme system comprising multiple enzymes that are capable of acting in concert to facilitate detection of the first analyte.

In some embodiments, the second analyte sensor further includes a second analyte-responsive active area comprising a second electron transfer agent, a second polymer, and an enzyme system comprising multiple enzymes that are capable of acting in concert to facilitate detection of the second analyte.

In some embodiments, the first analyte is selected from the group consisting of glucose, β-hydroxybutyrate, uric acid, ketone, creatinine, ethanol, and lactate.

In some embodiments, the second analyte is selected from the group consisting of glucose, β-hydroxybutyrate, uric acid, ketone, creatinine, ethanol, and lactate.

In some embodiments, the implantable sensor tails of the first and second sensors are configured for insertion into a tissue.

In some embodiments, the fluid is a biological fluid and the analyte sensor is exposed to the biological fluid in vivo.

In some embodiments, the first signal and the second signal are measured at different times.

In some embodiments, the first signal and the second signal are measured at the same time.

In some embodiments, the first signal and the second signal are obtained simultaneously via a first channel and a second channel.

In some embodiments, the second analyte sensor further comprises a third working electrode, wherein the third working electrode further comprises a third analyte-responsive active area comprising a third electron transfer agent, a third polymer, and an enzyme system comprising multiple enzymes that are capable of acting in concert to facilitate detection of the third analyte. In some embodiments, the second analyte sensor further comprises a fourth working electrode, wherein the fourth working electrode further comprises a fourth analyte-responsive active area comprising a fourth electron transfer agent, a fourth polymer, and an enzyme system comprising multiple enzymes that are capable of acting in concert to facilitate detection of the third analyte.

In some embodiments, the method further including the steps of applying a potential to the third working electrode and the fourth working electrode and the first sensor; obtaining a third signal at or above an oxidation-reduction potential of the third analyte-responsive active area, the third signal being proportional to a concentration of the third analyte in the fluid; obtaining a fourth signal at or above an oxidation-reduction potential of the fourth analyte-responsive active area, the fourth signal being proportional to a concentration of the fourth analyte in the fluid; and correlating the third signal to the concentration of the third analyte in the fluid and the fourth signal to the concentration of the fourth analyte in the fluid.

In many embodiments, an on body device for use in an analyte monitoring system is described. The on body device includes a housing; and a first sensor and a second sensor disposed within the housing, wherein the first sensor comprises an implantable sensor tail comprising a first working electrode, a second working electrode, a shared reference electrode, and a shared counter electrode, and wherein the second sensor comprises an implantable sensor tail comprising first working electrode and a second working electrode, wherein the second sensor does not include a counter electrode and a reference electrode.

In some embodiments, the first sensor further comprises a first analyte-responsive active area disposed upon a surface of the first working electrode of the first sensor and a second analyte-responsive active area disposed upon a surface of the second working electrode of the first sensor. In some embodiments, the first analyte-responsive active area and second analyte-responsive active area each further comprise an electron-transfer agent that is covalently bonded to a polymer in each of the first analyte-responsive active area and second analyte-responsive active areas. In some embodiments, the first analyte is selected from the group consisting of glucose, β-hydroxybutyrate, uric acid, ketone, creatinine, ethanol, and lactate. In some embodiments, the second analyte is selected from the group consisting of glucose, β-hydroxybutyrate, uric acid, ketone, creatinine, ethanol, and lactate. In some embodiments, the first sensor further comprises a first membrane that is permeable to the first analyte and overcoats the first analyte-responsive active area and a second membrane that is permeable to the second analyte and overcoats the second analyte-responsive active area.

In some embodiments, the second sensor further comprises a third analyte-responsive active area disposed upon a surface of the first working electrode of the second sensor and a fourth analyte-responsive active area disposed upon a surface of the second working electrode of the second sensor. In some embodiments, the third analyte-responsive active area and fourth analyte-responsive active area each further comprise an electron-transfer agent that is covalently bonded to a polymer in each of the third analyte-responsive active area and fourth analyte-responsive active area. In some embodiments, the third analyte is selected from the group consisting of glucose, β-hydroxybutyrate, uric acid, ketone, creatinine, ethanol, and lactate. In some embodiments, the fourth analyte is selected from the group consisting of glucose, β-hydroxybutyrate, uric acid, ketone, creatinine, ethanol, and lactate. In some embodiments, the second sensor further comprises a third membrane that is permeable to the third analyte and overcoats the third analyte-responsive active area and a fourth membrane that is permeable to the fourth analyte and overcoats the fourth analyte-responsive active area.

In some embodiments, the implantable sensor tails of the first and second sensors are configured for insertion into a tissue.

In some embodiments, the second sensor further comprises a third working electrode and a fourth working electrode. In some embodiments, the second sensor further comprises a fifth analyte-responsive active area disposed upon a surface of the third working electrode of the second sensor and a sixth analyte-responsive active area disposed upon a surface of the fourth working electrode of the second sensor. In some embodiments, the fifth analyte-responsive active area and sixth analyte-responsive active area each further comprise an electron-transfer agent that is covalently bonded to a polymer in each of the fifth analyte-responsive active area and sixth analyte-responsive active areas. In some embodiments, the fifth analyte is selected from the group consisting of glucose, β-hydroxybutyrate, uric acid, ketone, creatinine, ethanol, and lactate. In some embodiments, the sixth analyte is selected from the group consisting of glucose, β-hydroxybutyrate, uric acid, ketone, creatinine, ethanol, and lactate.

In some embodiments, the device further includes analog front end circuitry disposed within the housing, wherein the analog front end circuitry receives analyte data from the first and second working electrodes of the first sensor and the first and second working electrodes of the second sensor. In some embodiments, the first and second working electrodes of the second sensor are connected to the analog front end circuitry through a circuit trace. In some embodiments, the first and second working electrodes of the second sensor are connected to the analog front end circuitry through a flexible circuit connection.

In some embodiments, the device further includes analog front end circuitry disposed within the housing, wherein the analog front end circuitry receives analyte data from the first and second working electrodes of the first sensor and the first, second, third, and fourth working electrodes of the second sensor. In some embodiments, the first, second, third, and fourth working electrodes of the second sensor are connected to the analog front end circuitry through a circuit trace. In some embodiments, the first, second, third, and fourth working electrodes of the second sensor are connected to the analog front end circuitry through a flexible circuit connection.

In many embodiments, a method is described. The method includes the steps of exposing an analyte sensor system to a fluid comprising at least a first, second, third, and fourth analyte, wherein the analyte sensor system comprises a first sensor and a second sensor, wherein the first sensor comprises an implantable sensor tail comprising a first working electrode, a second working electrode, a shared reference electrode, and a shared counter electrode, and the second sensor comprises an implantable sensor tail comprising a first working electrode and a second working electrode, wherein the second sensor does not include a counter electrode and a reference electrode, wherein each of the first and second working electrodes of the first sensor comprises first and second analyte-responsive active areas, respectively, and wherein the first and second working electrodes of the second sensor each comprises third and fourth analyte-responsive active areas, respectively; applying a potential to the first and second working electrodes of the first and second sensors; obtaining a first signal at or above an oxidation-reduction potential of the first analyte-responsive active area, the signal being proportional to a concentration of the first analyte in the fluid; obtaining a second signal at or above an oxidation-reduction potential of the second analyte-responsive active area, the second signal being proportional to a concentration of the second analyte in the fluid; obtaining a third signal at or above an oxidation-reduction potential of the third analyte-responsive active area, the third signal being proportional to a concentration of the third analyte in the fluid; obtaining a fourth signal at or above an oxidation-reduction potential of the third analyte-responsive active area, the third signal being proportional to a concentration of the fourth analyte in the fluid; and correlating the first, second, third, and fourth signals to the concentrations of the first, second, third, and fourth analytes in the fluid, respectively.

In some embodiments, the first, second, third, and fourth analyte-responsive active areas each comprise an electron-transfer agent that is covalently bonded to a polymer in each of the first, second, third, and fourth analyte-responsive active areas, respectively.

In some embodiments, the first analyte is selected from the group consisting of glucose, β-hydroxybutyrate, uric acid, ketone, creatinine, ethanol, and lactate.

In some embodiments, the second analyte is selected from the group consisting of glucose, β-hydroxybutyrate, uric acid, ketone, creatinine, ethanol, and lactate.

In some embodiments, the third analyte is selected from the group consisting of glucose, β-hydroxybutyrate, uric acid, ketone, creatinine, ethanol, and lactate.

In some embodiments, the fourth analyte is selected from the group consisting of glucose, β-hydroxybutyrate, uric acid, ketone, creatinine, ethanol, and lactate.

In some embodiments, the implantable sensor tails of the first and second sensors are configured for insertion into a tissue.

In some embodiments, at least a portion of the implantable sensor tail of the first sensor further comprises a first membrane disposed over the first analyte-responsive active area and a second membrane disposed over the second analyte-responsive active area.

In some embodiments, at least a portion of the implantable sensor tail of the second sensor further comprises a third membrane disposed over the third analyte-responsive active area and a fourth membrane disposed over the fourth analyte-responsive active area.

In some embodiments, the first working electrode of the first sensor is separated from the counter electrode or reference electrode by a dielectric layer.

In some embodiments, the second working electrode of the first sensor is separated from the counter electrode or reference electrode by a dielectric layer.

In some embodiments, wherein the analyte sensor system further includes first and second dielectric layers disposed on the reference electrode and the counter electrode.

In some embodiments, the fluid is a biological fluid and the analyte sensor is exposed to the biological fluid in vivo.

In some embodiments, the first, second, third, and fourth signals are measured at different times.

In some embodiments, the first, second, third, and fourth signals are measured at the same time.

In some embodiments, the first, second, third, and fourth signals are obtained simultaneously via different channels.

In some embodiments, the fluid comprises a fifth analyte and a sixth analyte, and wherein the implantable sensor tail of the second sensor further comprises third and fourth working electrodes, wherein the third and fourth working electrodes of the second sensor each comprises fifth and sixth analyte-responsive active areas, respectively.

In some embodiments, the method further includes the steps of applying a potential to the third and fourth working electrodes of the second sensor; obtaining a fifth signal at or above an oxidation-reduction potential of the fifth analyte-responsive active area, the signal being proportional to a concentration of the fifth analyte in the fluid; obtaining a sixth signal at or above an oxidation-reduction potential of the sixth analyte-responsive active area, the second signal being proportional to a concentration of the sixth analyte in the fluid; and correlating the fifth and sixth signals to the concentrations of the fifth and sixth analytes in the fluid, respectively.

In some embodiments, the first sensor and the second sensor are disposed within the same housing.

In some embodiments, the first sensor is disposed within a first housing and wherein the second sensor is disposed within a second housing. In some embodiments, the analyte sensor system further comprises analog front end circuitry disposed within the first housing, wherein the analog front end circuitry receives analyte data from the first and second working electrodes of the first sensor and the first and second working electrodes of the second sensor.

In some embodiments, the analyte sensor system further comprises analog front end circuitry disposed within the first housing, wherein the analog front end circuitry receives analyte data from the first and second working electrodes of the first sensor and the first, second, third, and fourth working electrodes of the second sensor.

In some embodiments, the analyte sensor system further comprises a third sensor, wherein the third sensor comprises an implantable sensor tail comprising a first working electrode and a second working electrode, wherein the third sensor does not include a counter electrode and a reference electrode. In some embodiments, the third sensor is disposed within a third housing. In some embodiments, the fluid comprises a seventh analyte and an eighth analyte, and wherein the implantable sensor tail of the third sensor further comprises first and second working electrodes, wherein the first and second working electrodes of the third sensor each comprises seventh and eighth analyte-responsive active areas, respectively. In some embodiments, the method further includes the steps of applying a potential to the first and second working electrodes of the third sensor; obtaining a seventh signal at or above an oxidation-reduction potential of the seventh analyte-responsive active area, the seventh signal being proportional to a concentration of the seventh analyte in the fluid; obtaining a eighth signal at or above an oxidation-reduction potential of the eighth analyte-responsive active area, the eighth signal being proportional to a concentration of the eighth analyte in the fluid; and correlating the seventh and eighth signals to the concentrations of the seventh and eighth analytes in the fluid, respectively.

In some embodiments, the fluid comprises a ninth analyte and a tenth analyte, and wherein the implantable sensor tail of the third sensor further comprises third and fourth working electrodes, wherein the third and fourth working electrodes of the third sensor each comprises ninth and tenth analyte-responsive active areas, respectively. In some embodiments, the method further includes the steps of applying a potential to the third and fourth working electrodes of the third sensor; obtaining a ninth signal at or above an oxidation-reduction potential of the ninth analyte-responsive active area, the ninth signal being proportional to a concentration of the ninth analyte in the fluid; obtaining a tenth signal at or above an oxidation-reduction potential of the tenth analyte-responsive active area, the tenth signal being proportional to a concentration of the eighth analyte in the fluid; and correlating the ninth and tenth signals to the concentrations of the ninth and tenth analytes in the fluid, respectively.

In some embodiments, an on body device for use in an analyte monitoring system is described. The device includes a first housing; a first sensor disposed within the first housing, wherein the first sensor comprises an implantable sensor tail comprising a first working electrode, a second working electrode, a reference electrode, and a counter electrode; a second housing; and a second sensor disposed within the second housing, wherein the second sensor comprises an implantable sensor tail comprising first working electrode and a second working electrode, wherein the second sensor does not include a counter electrode and a reference electrode.

In some embodiments, the device also includes an adhesive layer, wherein the first and second housings are disposed on the adhesive layer.

In some embodiments, the first sensor further comprises a first analyte-responsive active area disposed upon a surface of the first working electrode of the first sensor and a second analyte-responsive active area disposed upon a surface of the second working electrode of the first sensor. In some embodiments, the first analyte-responsive active area and second analyte-responsive active area each further comprise an electron-transfer agent that is covalently bonded to a polymer in each of the first analyte-responsive active area and second analyte-responsive active areas. In some embodiments, the first analyte is selected from the group consisting of glucose, β-hydroxybutyrate, uric acid, ketone, creatinine, ethanol, and lactate. In some embodiments, the second analyte is selected from the group consisting of glucose, β-hydroxybutyrate, uric acid, ketone, creatinine, ethanol, and lactate. In some embodiments, the second sensor further comprises a third analyte-responsive active area disposed upon a surface of the first working electrode of the second sensor and a fourth analyte-responsive active area disposed upon a surface of the second working electrode of the second sensor. In some embodiments, the third analyte-responsive active area and fourth analyte-responsive active area each further comprise an electron-transfer agent that is covalently bonded to a polymer in each of the third analyte-responsive active area and fourth analyte-responsive active area. In some embodiments, the third analyte is selected from the group consisting of glucose, β-hydroxybutyrate, uric acid, ketone, creatinine, ethanol, and lactate. In some embodiments, the fourth analyte is selected from the group consisting of glucose, β-hydroxybutyrate, uric acid, ketone, creatinine, ethanol, and lactate.

In some embodiments, the implantable sensor tails of the first and second sensors are configured for insertion into a tissue.

In some embodiments, the second sensor further comprises a third working electrode and a fourth working electrode. In some embodiments, the second sensor further comprises a fifth analyte-responsive active area disposed upon a surface of the third working electrode of the second sensor and a sixth analyte-responsive active area disposed upon a surface of the fourth working electrode of the second sensor. In some embodiments, the fifth analyte-responsive active area and sixth analyte-responsive active area each further comprise an electron-transfer agent that is covalently bonded to a polymer in each of the fifth analyte-responsive active area and sixth analyte-responsive active areas. In some embodiments, the fifth analyte is selected from the group consisting of glucose, β-hydroxybutyrate, uric acid, ketone, creatinine, ethanol, and lactate. In some embodiments, the sixth analyte is selected from the group consisting of glucose, β-hydroxybutyrate, uric acid, ketone, creatinine, ethanol, and lactate.

In some embodiments, the analyte system further includes analog front end circuitry disposed within the first housing, wherein the analog front end circuitry receives analyte data from the first and second working electrodes of the first sensor and the first and second working electrodes of the second sensor. In some embodiments, the first and second working electrodes of the second sensor are connected to the analog front end circuitry through a circuit trace. In some embodiments, the first and second working electrodes of the second sensor are connected to the analog front end circuitry through a flexible circuit connection.

In some embodiments, the analyte system further includes analog front end circuitry disposed within the housing, wherein the analog front end circuitry receives analyte data from the first and second working electrodes of the first sensor and the first, second, third, and fourth working electrodes of the second sensor. In some embodiments, the first, second, third, and fourth working electrodes of the second sensor are connected to the analog front end circuitry through a circuit trace. In some embodiments, the first, second, third, and fourth working electrodes of the second sensor are connected to the analog front end circuitry through a flexible circuit connection.

In some embodiments, the analyte system further includes a third housing disposed on the adhesive layer; and a third sensor disposed within the second housing, wherein the third sensor comprises an implantable sensor tail comprising a first working electrode and a second working electrode, wherein the third sensor does not include a counter electrode and a reference electrode. In some embodiments, the third sensor further comprises a seventh analyte-responsive active area disposed upon a surface of the first working electrode of the third sensor and an eighth analyte-responsive active area disposed upon a surface of the second working electrode of the third sensor. In some embodiments, the seventh analyte-responsive active area and eighth analyte-responsive active area each further comprise an electron-transfer agent that is covalently bonded to a polymer in each of the seventh analyte-responsive active area and eighth analyte-responsive active areas. In some embodiments, the seventh analyte is selected from the group consisting of glucose, β-hydroxybutyrate, uric acid, ketone, creatinine, ethanol, and lactate. In some embodiments, the eighth analyte is selected from the group consisting of glucose, β-hydroxybutyrate, uric acid, ketone, creatinine, ethanol, and lactate.

In some embodiments, the analyte system further includes analog front end circuitry disposed within the first housing, wherein the analog front end circuitry receives analyte data from the first and second working electrodes of the third sensor. In some embodiments, the first and second working electrodes of the third sensor are connected to the analog front end circuitry through a circuit trace. In some embodiments, the first and second working electrodes of the third sensor are connected to the analog front end circuitry through a flexible circuit connection.

In some embodiments, the implantable sensor tail of the third sensor further comprises a third working electrode and a fourth working electrode, and a ninth analyte-responsive active area disposed upon a surface of the third working electrode of the third sensor and a tenth analyte-responsive active area disposed upon a surface of the fourth working electrode of the third sensor. In some embodiments, the ninth analyte-responsive active area and tenth analyte-responsive active area each further comprise an electron-transfer agent that is covalently bonded to a polymer in each of the ninth analyte-responsive active area and tenth analyte-responsive active areas. In some embodiments, the ninth analyte is selected from the group consisting of glucose, β-hydroxybutyrate, uric acid, ketone, creatinine, ethanol, and lactate. In some embodiments, the tenth analyte is selected from the group consisting of glucose, β-hydroxybutyrate, uric acid, ketone, creatinine, ethanol, and lactate. In some embodiments, the analyte system also includes analog front end circuitry disposed within the first housing, wherein the analog front end circuitry receives analyte data from the third and fourth working electrodes of the third sensor. In some embodiments, the third and fourth working electrodes of the third sensor are connected to the analog front end circuitry through a circuit trace. In some embodiments, the third and fourth working electrodes of the third sensor are connected to the analog front end circuitry through a flexible circuit connection.

In many embodiments, an analyte sensor is described. The analyte sensor includes an implantable sensor tail comprising: a substrate having a first side and a second side; a first working electrode located on a substrate; a second working electrode is located on the substrate; a first analyte-responsive active area disposed upon a surface of the first working electrode; and a second analyte-responsive active area disposed upon a surface of the second working electrode, wherein the first analyte-responsive active area is located closer to a distal end of the substrate than the second analyte-responsive active area, and wherein a distance between a proximal end of the first analyte-responsive active area and a distal end of the second analyte-responsive active area is at least about 0.2 mm.

In some embodiments, the first and second working electrodes are separated by an insulating or dielectric layer.

In some embodiments, the first working electrode is located on a first side of the substrate and the second working electrode is located on a second side of the substrate.

In some embodiments, the first working electrode and the second working electrode are located on a first side of the substrate.

In some embodiments, the distance between a proximal end of the first analyte-responsive active area and the distal end of the second analyte-responsive active area is between about 0.4 to about 1.1 mm.

In some embodiments, the analyte sensor further includes a first membrane that is permeable to the first analyte and overcoats the first analyte-responsive active area; and a second membrane that is permeable to the second analyte and overcoats the first and the second analyte-responsive active areas. In some embodiments, the first membrane and the second membrane have different compositions. In some embodiments, the first membrane and the second membrane have the same compositions.

In some embodiments, the first analyte-responsive active area and the second analyte-responsive active area each comprise an electron-transfer agent that is covalently bonded to a polymer in each of the first analyte-responsive active area and second analyte-responsive active area.

In some embodiments, the first analyte-responsive active area further comprises a first electron transfer agent, a first polymer, and an enzyme system comprising multiple enzymes that are capable of acting in concert to facilitate detection of the first analyte.

In some embodiments, the second analyte-responsive active area further comprises a second electron transfer agent, a second polymer, and an enzyme system comprising multiple enzymes that are capable of acting in concert to facilitate detection of the second analyte.

In some embodiments, the analyte sensor further includes a reference electrode and a counter electrode. In some embodiments, the analyte sensor further includes a reference material layer on a surface of the reference electrode. In some embodiments, the reference materials comprises Ag and AgCl.

In some embodiments, the first analyte is selected from the group consisting of glucose, β-hydroxybutyrate, uric acid, ketone, creatinine, ethanol, and lactate. In some embodiments, the first analyte is ketone or β-hydroxybutyrate.

In some embodiments, the second analyte is selected from the group consisting of glucose, β-hydroxybutyrate, uric acid, ketone, creatinine, ethanol, and lactate. In some embodiments, the second analyte is glucose.

In some embodiments, the implantable sensor tail is configured for insertion into a tissue.

In some embodiments, a distal region of the implantable sensor tail has a maximum thickness of between about 0.25 mm to about 0.4 mm.

In many embodiments, a method is described. The method includes the steps of exposing an analyte sensor to a fluid comprising at least a first analyte and a second analyte, wherein the analyte sensor comprises an implantable sensor tail comprising a substrate having a first side and a second side, a first working electrode located on a first side of a substrate; a second working electrode located on the first side of the substrate, a first analyte-responsive active area disposed upon a surface of the first working electrode, and a second analyte-responsive active area disposed upon a surface of the second working electrode, wherein the first analyte-responsive active area is located closer to a distal end of the substrate than the second analyte-responsive active area, and wherein a distance between a proximal end of the first analyte-responsive active area and a distal end of the second analyte-responsive active area is at least about 0.2 mm; applying a potential to the first working electrode and the second working electrode; obtaining a first signal at or above an oxidation-reduction potential of the first analyte-responsive active area, the signal being proportional to a concentration of the first analyte in the fluid; obtaining a second signal at or above an oxidation-reduction potential of the second analyte-responsive active area, the second signal being proportional to a concentration of the second analyte in the fluid; and correlating the first signal to the concentration of the first analyte in the fluid and the second signal to the concentration of the second analyte in the fluid.

In some embodiments, the first and second working electrodes are separated by an insulating layer.

In some embodiments, the implantable sensor tail further comprises a first membrane that is permeable to the first analyte and overcoats the first analyte-responsive active area and a second membrane that is permeable to the second analyte and overcoats the first and second analyte-responsive active areas.

In some embodiments, the first analyte-responsive active area and second analyte-responsive active area each comprise an electron-transfer agent that is covalently bonded to a polymer in each of the first analyte-responsive active area and second analyte-responsive active area.

In some embodiments, the first analyte-responsive active area further comprises a first electron transfer agent, a first polymer, and an enzyme system comprising multiple enzymes that are capable of acting in concert to facilitate detection of the first analyte.

In some embodiments, the second analyte-responsive active area further comprises a second electron transfer agent, a second polymer, and an enzyme system comprising multiple enzymes that are capable of acting in concert to facilitate detection of the second analyte.

In some embodiments, the first analyte is selected from the group consisting of glucose, β-hydroxybutyrate, uric acid, ketone, creatinine, ethanol, and lactate. In some embodiments, the first analyte is ketone or β-hydroxybutyrate.

In some embodiments, the second analyte is selected from the group consisting of glucose, β-hydroxybutyrate, uric acid, ketone, creatinine, ethanol, and lactate. In some embodiments, the second analyte is glucose.

In some embodiments, the first membrane and the second membrane have different compositions.

In some embodiments, the first working electrode is separated from the second working electrode by a dielectric layer.

In some embodiments, the fluid is a biological fluid and the analyte sensor is exposed to the biological fluid in vivo.

In some embodiments, the first signal and the second signal are measured at different times.

In some embodiments, the first signal and the second signal are measured at the same time.

In some embodiments, the first signal and the second signal are obtained simultaneously via a first channel and a second channel.

In some embodiments, a distal region of the implantable sensor tail has a maximum thickness of between about 0.25 mm to about 0.4 mm.

In many embodiments, an analyte sensor is described. The analyte sensor includes an implantable sensor tail comprising: a substrate having a first side and a second side; a first working electrode located on and in contact with a first side of a substrate; a first analyte-responsive active area disposed upon a surface of the first working electrode; a second working electrode located on and in contact with the first side of the substrate; a second analyte-responsive active area disposed upon a surface of the second working electrode, wherein the first analyte-responsive active area is located closer to a distal end of the substrate than the second analyte-responsive active area; a counter electrode; and a reference electrode.

In some embodiments, a distance between a proximal end of the first analyte-responsive active area and a distal end of the second analyte-responsive active area is between about 0.4 to about 1.1 mm.

In some embodiments, the first and second working electrodes are not separated from the first side of the substrate by a dielectric layer.

In some embodiments, the counter and reference electrodes are located on and in contact with the first side of the substrate. In some embodiments, the counter and reference electrodes are not separated from the first side of the substrate by a dielectric layer.

In some embodiments, the counter and reference electrodes are located on and in contact with the second side of the substrate.

In some embodiments, the analyte sensor further includes a first membrane that is permeable to the first analyte and overcoats the first analyte-responsive active area; and a second membrane that is permeable to the second analyte and overcoats the first and the second analyte-responsive active areas.

In some embodiments, the first analyte-responsive active area and the second analyte-responsive active area each comprise an electron-transfer agent that is covalently bonded to a polymer in each of the first analyte-responsive active area and second analyte-responsive active area.

In some embodiments, the first analyte-responsive active area further comprises a first electron transfer agent, a first polymer, and an enzyme system comprising multiple enzymes that are capable of acting in concert to facilitate detection of the first analyte.

In some embodiments, the second analyte-responsive active area further comprises a second electron transfer agent, a second polymer, and an enzyme system comprising multiple enzymes that are capable of acting in concert to facilitate detection of the second analyte.

In some embodiments, a distal region of the implantable sensor tail has a maximum thickness of between about 0.25 mm to about 0.4 mm.

In many embodiments, a method is described. The method includes the steps of exposing an analyte sensor to a fluid comprising at least a first analyte and a second analyte, wherein the analyte sensor comprises an implantable sensor tail comprising a substrate having a first side and a second side; a first working electrode located on and in contact with a first side of a substrate; a first analyte-responsive active area disposed upon a surface of the first working electrode; a second working electrode located on and in contact with the first side of the substrate; a second analyte-responsive active area disposed upon a surface of the second working electrode, wherein the first analyte-responsive active area is located closer to a distal end of the substrate than the second analyte-responsive active area; a counter electrode; and a reference electrode; applying a potential to the first working electrode and the second working electrode; obtaining a first signal at or above an oxidation-reduction potential of the first analyte-responsive active area, the signal being proportional to a concentration of the first analyte in the fluid; obtaining a second signal at or above an oxidation-reduction potential of the second analyte-responsive active area, the second signal being proportional to a concentration of the second analyte in the fluid; and correlating the first signal to the concentration of the first analyte in the fluid and the second signal to the concentration of the second analyte in the fluid.

In some embodiments, a distance between a proximal end of the first analyte-responsive active area and a distal end of the second analyte-responsive active area is between about 0.4 to about 1.1 mm.

In some embodiments, the first and second working electrodes are not separated from the first side of the substrate by a dielectric layer.

In some embodiments, the counter and reference electrodes are located on and in contact with the first side of the substrate. In some embodiments, the counter and reference electrodes are not separated from the first side of the substrate by a dielectric layer.

In some embodiments, the counter and reference electrodes are located on and in contact with the second side of the substrate.

In some embodiments, the analyte system further includes a first membrane that is permeable to the first analyte and overcoats the first analyte-responsive active area; and a second membrane that is permeable to the second analyte and overcoats the first and the second analyte-responsive active areas.

In some embodiments, the first analyte-responsive active area and the second analyte-responsive active area each comprise an electron-transfer agent that is covalently bonded to a polymer in each of the first analyte-responsive active area and second analyte-responsive active area.

In some embodiments, the first analyte-responsive active area further comprises a first electron transfer agent, a first polymer, and an enzyme system comprising multiple enzymes that are capable of acting in concert to facilitate detection of the first analyte.

In some embodiments, the second analyte-responsive active area further comprises a second electron transfer agent, a second polymer, and an enzyme system comprising multiple enzymes that are capable of acting in concert to facilitate detection of the second analyte.

In some embodiments, the fluid is a biological fluid and the analyte sensor is exposed to the biological fluid in vivo.

In some embodiments, the first signal and the second signal are measured at different times.

In some embodiments, the first signal and the second signal are measured at the same time.

In some embodiments, the first signal and the second signal are obtained simultaneously via a first channel and a second channel.

In some embodiments, the first analyte is selected from the group consisting of glucose, β-hydroxybutyrate, uric acid, ketone, creatinine, ethanol, and lactate. In some embodiments, the first analyte is β-hydroxybutyrate or ketone.

In some embodiments, the second analyte is selected from the group consisting of glucose, β-hydroxybutyrate, uric acid, ketone, creatinine, ethanol, and lactate. In some embodiments, the second analyte is glucose.

In some embodiments, a distal region of the implantable sensor tail has a maximum thickness of between about 0.25 mm to about 0.4 mm.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. An electrochemical analyte sensor for continuously detecting glucose and ketones in vivo, the sensor comprising:
    a substrate;
    a first working electrode disposed on the substrate;
    a dielectric layer disposed on the first working electrode;
    a second working electrode disposed on the dielectric layer;
    a ketones-responsive active area disposed upon a surface of the first working electrode;
    a glucose-responsive active area disposed upon a surface of the second working electrode;
    a first membrane that is permeable to ketones and overcoats the ketones-responsive active area; and
    a second membrane that is permeable to glucose and overcoats the ketones-responsive and the glucose-responsive active areas,
    wherein the ketones-responsive active area is located closer to a distal end of the sensor than the glucose-responsive active area, and wherein a distance between the ketones-responsive active area and the glucose-responsive active area is 0.4 mm to 1.1 mm, and
    wherein the sensor is partially insertable into skin such that the distal end of the sensor is in contact with an interstitial fluid to continuously detect glucose and ketones in vivo.

2. The sensor of claim 1, wherein the ketones-responsive active area comprises a first polymer and a first electron transfer agent covalently bonded to the first polymer and the glucose-responsive active area comprises a second polymer and a second electron transfer agent covalently bonded to the second polymer.

3. The sensor of claim 1, wherein the ketones-responsive active area further comprises an enzyme system comprising multiple enzymes that are capable of acting in concert to facilitate detection of ketones.

4. The sensor of claim 1, wherein the glucose-responsive active area further comprises an enzyme to facilitate detection of glucose.

5. The sensor of claim 1, wherein the first membrane and the second membrane have different compositions.

6. The sensor of claim 1, wherein the distal end of the sensor has a maximum thickness of between about 0.2 mm and about 0.4 mm.

7. The sensor of claim 1, further comprising a single reference electrode.

8. The sensor of claim 1, wherein the second membrane is permeable to ketones.

9. The sensor of claim 1, wherein the first membrane comprises polyvinylpyridine.

10. The sensor of claim 1, wherein the second membrane comprises polyvinylpyridine-co-styrene.

11. The sensor of claim 1, wherein the distance between the ketones-responsive active area and the glucose-responsive active area is a distance between a proximal end of the ketones-responsive active area and a distal end of the glucose-responsive active area along a length of the substrate.

* * * * *